US008158582B2

(12) United States Patent
Clark

(10) Patent No.: US 8,158,582 B2
(45) Date of Patent: Apr. 17, 2012

(54) METHODS FOR TREATMENT OF INSULIN-LIKE GROWTH FACTOR-1 DEFICIENCY

(75) Inventor: Ross G. Clark, Auckland (NZ); Gillian Clark, legal representative, Auckland (NZ)

(73) Assignee: Tercica, Inc., South San Francisco, CA (US)

( * ) Notice: Subject to any disclaimer, the term of this patent is extended or adjusted under 35 U.S.C. 154(b) by 405 days.

(21) Appl. No.: 11/915,978

(22) PCT Filed: Jun. 1, 2006

(86) PCT No.: PCT/US2006/021282
§ 371 (c)(1),
(2), (4) Date: Oct. 19, 2009

(87) PCT Pub. No.: WO2006/130769
PCT Pub. Date: Dec. 7, 2006

(65) Prior Publication Data
US 2010/0137200 A1  Jun. 3, 2010

Related U.S. Application Data

(60) Provisional application No. 60/687,617, filed on Jun. 2, 2005.

(51) Int. Cl.
A61K 38/30 (2006.01)
A61K 38/27 (2006.01)
A61K 38/22 (2006.01)
A61K 38/18 (2006.01)
A61K 38/16 (2006.01)
A61K 39/00 (2006.01)

(52) U.S. Cl. .......... 514/8.6; 514/11.4; 514/5.1; 514/5.3; 514/7.6; 514/21.3; 424/198.1

(58) Field of Classification Search ........................ None
See application file for complete search history.

(56) References Cited

U.S. PATENT DOCUMENTS

| 5,126,324 A | 6/1992 | Clark et al. |
| 5,374,620 A | 12/1994 | Clark et al. |
| 5,681,814 A | 10/1997 | Clark et al. |
| 5,741,776 A | 4/1998 | Clark et al. |
| 5,824,642 A | 10/1998 | Attie et al. |
| 6,034,059 A | 3/2000 | Fryklund et al. |
| 6,358,925 B1 | 3/2002 | Guler et al. |
| 7,258,864 B2 | 8/2007 | Clark |

FOREIGN PATENT DOCUMENTS

WO  WO 2011/060922  5/2011

OTHER PUBLICATIONS

Vaccarello, et al. Hormonal and metabolic effects and pharmacokinetics of recombinant insulin-like growth factor-I in growth hormone receptor deficiency/Laron syndrome. J Clin Endocrinol Metab. Jul. 1993;77(1):273-80.

Guevara-Aguirre, J., et al. "A pharmacokinetic study to access doing requirements for recombinant human IGF-1 in patients with primary IGF-1 deficiency." poster No. P1052 presented at 12th International Congress of Endocrinology Meeting of Sep. 2004 in Lisbon, Portugal.

Tercica, Inc. Press Release Sep. 7, 2004.

Liao, S., et al. "Validation of a population pharmocokinetic (POP-PK) model for rhIGF-1 in humans." poster presented at ENDO meeting of 2005 in San Diego, CA.

Tercica, Inc. Form 10-K (Annual Report) filed Mar. 24, 2005 for period ending Dec. 31, 2004.

Klinger B. and Laron, Z. "Three year IGF-1 treatment of children with laron syndrome." J. Ped. Endo. Metab., 1995, 8: 149-158.

Ammann, P., R. Rizzoli, et al. (1996). "Bone density and shape as determinants of bone strength in IGF-I and/or pamidronate-treated ovariectomized rats." Osteoporos Int 6(3): 219-27.

Bikle, A D., T. Sakata, et al. (2002). "Insulin-like growth factor I is required for the anabolic actions of parathyroid hormone on mouse bone." J Bone Miner Res 17(9): 1570-8.

Clemmons DR et al. Evaluation of acromegaly by radioimmunoassay of somatomedin-C. 1979, N Engl J Med 301:1138-42.

Clemmons DR et al. Somatomedin-C/insulin-like growth factor I in acromegaly. 1986, Olin Endocrinol Metal 15:629-51.

Gamero, P., E Sornay-Rendu, et al. (2000). "Low serum IGF-1 and occurrence of osteoporotic fractures in postmenopausal women." Lancet 355(9207): 898-9.

Golden, N. H., E A Iglesias, et al. (2005). "Alendronate for the treatment of osteopenia in anorexia nervosa: a randomized, double-blind, placebo-controlled trial." J Clin Endocrinol Metab 90(6): 3179-85. Golden, N. H., L. Lanzkowsky, et al. (2002). "The effect of estrogen-progestin treatment on bone mineral density in anorexia nervosa." J Pediatr Adolesc Gynecol 15(3): 135-43.

Grinspoon, S., E Thomas, et al. (2000). "Prevalence and predictive factors for regional osteopenia in women with anorexia nervosa." Ann Intern Med 133(10): 790-4.

(Continued)

Primary Examiner — Shulamith H Shafer
(74) Attorney, Agent, or Firm — Paula A. Borden; Bozicevic, Field & Francis LLP.

(57) ABSTRACT

The present invention provides methods and compositions for increasing the growth rates, alleviating the symptoms, or improving the metabolism of human patients having an endocrine disorder characterized by partial endogenous growth hormone activity or signaling. The invention provides a method comprising administering to a patient suffering from an endocrine disorder characterized by partial endogenous growth hormone activity or signaling an amount of insulin-like growth factor-1 (IGF-1) effective to improve metabolism in the patient, where the patient receives IGF-1 in a single daily administration. The invention also provides a method comprising administering to a patient suffering from an endocrine disorder characterized by partial endogenous growth hormone activity or signaling an amount of insulin-like growth factor-1 (IGF-1) and an amount of growth hormone (GH) that in combination are effective to improve growth or metabolism in the patient, where the patient receives IGF-1 in a single daily administration and receives GH in a single daily administration, and where the single IGF-1 administration and the single GH administration are administered to the patient substantially contemporaneously each day.

18 Claims, 21 Drawing Sheets

OTHER PUBLICATIONS

Grinspoon, S., H. Baum, et al. (1996). "Effects of short-term recombinant human insulin-like growth factor I administration on bone turnover in osteopenic women with anorexia nervosa." J Clin Endocrinol Metab 81(11): 3864-70.

Grinspoon, S., L. Thomas, et al. (2002). "Effects of recombinant human IGF-I and oral contraceptive administration on bone density in anorexia nervosa." J Clin Endocrinol Metab 87(6): 2883-91.

Hoek, H. W. and D. van Hoeken (2003). "Review of the prevalence and incidence of eating disorders." Int J Eat Disord 34(4): 383-96.

Juul. Serum levels of insulin-like growth factor I and its binding proteins in health and disease. 2003, GH and IGF Research 13: 113-170.

Kasukawa, Y., D. J. Baylink, et al. (2003). "Lack of insulin-like growth factor I exaggerates the effect of calcium deficiency on bone accretion in mice." Endocrinology 144(11): 4682-9.

Kurland, E. S., C. J. Rosen, et al. (1997). "Insulin-like growth factor-I in men with idiopathic osteoporosis." J Clin Endocrinol Metab 82(9): 2799-805.

Langlois, J. A., C. J. Rosen, et al. (1998). "Association between insulin-like growth factor I and bone mineral density in older women and men: the Framingham Heart Study." J Clin Endocrinol Metab 83(12): 4257-62.

Liu, J-L and LeRoith, D. Insulin-like growth factor I is essential for postnatal growth in response to growth hormone. 1999, Endocrinology 140:5178-84.

Lucas, A. R., L. J. Melton, 3rd, et al. (1999). "Long-term fracture risk among women with anorexia nervosa: a population-based cohort study." Mayo Clin Proc 74(10): 972-7.

Lupu, F et al. Roles of growth hormone and insulin-like growth factor 1 in mouse postnatal growth. 2001, Dev Biol 229:141-62.

Miller, K. K., K. A. Grieco, et al. (2004). "Effects of risedronate on bone density in anorexia nervosa." J Clin Endocrinol Metab 89(8): 3903-6.

Miller, K. K., S. K. Grinspoon, et al. (2005). "Medical findings in outpatients with anorexia nervosa." Arch Intern Med 165(5): 561-6.

Munoz, M. T., G. Morande, et al. (2002). "The effects of estrogen administration on bone mineral density in adolescents with anorexia nervosa." Eur J Endocrinol 146(1): 45-50.

Nakaoka, D., T. Sugimoto, et al. (2001). "Determinants of bone mineral density and spinal fracture risk in postmenopausal Japanese women." Osteoporos Int 12(7): 548-54.

Clemmons DR et al. Factors controlling blood concentration of somatomedin C., 1984, Clin Endocrinol Metab 13:113-43.

Rigotti, N. A., R. M. Neer, et al. (1991). "The clinical course of osteoporosis in anorexia nervosa. A longitudinal study of cortical bone mass." JAMA 265(9): 1133-8.

Rivadeneira, F., J. J. Houwing-Duistermaat, et al. (2004). "The influence of an insulin-like growth factor I gene promoter polymorphism on hip bone geometry and the risk of nonvertebral fracture in the elderly: the Rotterdam Study." J Bone Miner Res 19(8): 1280-90.

Salmon WD Jr. et al. A hormonally controlled serum factor which stimulates sulfate incorporation by cartilage in vitro. 1957, J Lab Olin Med, 49:825-36.

Vahle, J. L., M. Sato, et al. (2002). "Skeletal changes in rats given daily subcutaneous injections of recombinant human parathyroid hormone (1-34) for 2 years and relevance to human safety." Toxicol Pathol 30(3): 312-21.

Van Wyk JJ. The Somatomedins: biological actions and physiological control mechanisms in Hormonal Proteins and Peptides, ed CH Li, 12:81-175, 1984.

Yager, J. and A. E. Andersen (2005). "Clinical practice. Anorexia nervosa." N. Engl J Med 353(14): 1481-8.

Yakar, S., C. J. Rosen, et al. (2002). "Circulating levels of IGF-1 directly regulate bone growth and density." J Clin Invest 110(6): 771-81.

Zhang, M., S. Xuan, et al. (2002). "Osteoblast-specific knockout of the insulin-like growth factor (IGF) receptor gene reveals an essential role of IGF signaling in bone matrix mineralization." J Biol Chem 277(46): 44005-12.

Zhou, Y et al. A mammalian model for laron syndrom produced by targeted disruption of the mouse growth hormone receptor/binding protein gene (the laron mouse). 1997, Proc Natl Acad Sci USA 94:13215-20.

Serum GH concentrations

Log of IGFBP-3, mcg/mL

METHODS FOR TREATMENT OF INSULIN-LIKE GROWTH FACTOR-1 DEFICIENCY

CROSS-REFERENCE TO RELATED APPLICATION

This application claims the benefit of U.S. Provisional Application No. 60/687,617, filed Jun. 2, 2005, which application is incorporated herein by reference in its entirety.

FIELD OF THE INVENTION

The present invention relates to methods and compositions for increasing the growth rates, alleviating the symptoms, or improving the metabolism of human patients having growth disorders, including non-growth hormone deficient, non-insulin-like growth factor deficient growth disorders (idiopathic short stature or ISS conditions).

BACKGROUND OF THE INVENTION

The American Academy of Pediatrics and the American Academy of Clinical Endocrinology define short stature based on height as more than two standard deviations below the average height of the population. A child with short stature is shorter than approximately 97.5% of children of a similar age and gender and typically attains final adult heights of no more than approximately 5'4" for boys and 4'11" for girls. It is estimated that 380,000 children in the U.S. are referred to pediatric endocrinologists for evaluation for short stature.

Children with short stature who are referred for evaluation and possible treatment continue to pose a dilemma for specialists despite decades of dedicated research. For patients with no demonstrable cause for their growth failure, a workup usually ensues which first seeks to differentiate between normal variation, in which the child should reach an adult height concordant with that of the child's genetic potential based on the average height of the parents, and pathologic conditions. In cases of marked short stature, in which the predicted adult height is also low, it is accepted practice to test the status of the growth hormone (GH)-insulin-like growth factor (IGF) axis.

Patients with abnormalities in the GH-IGF axis have a number of possible etiologies. They can present with GH deficiency (GHD), at times attributable to congenital or acquired central nervous system (CNS) lesions affecting the hypothalamus or pituitary, which is almost invariably accompanied by low IGF-1 levels in children. Alternatively, they can present with "primary IGF-1 deficiency" associated with low IGF-1 levels in the face of normal or elevated GH levels. Because IGF-1 is an essential mediator of GH's statural effects, primary IGF-1 deficiency can have similar clinical outcomes to GH deficiency. Such cases of primary IGF deficiency, in otherwise healthy and well-nourished patients, are likely to be caused by a defect somewhere in the GH-IGF axis downstream from the production or secretion of GH. This type of GH insensitivity or GH resistance is as yet unexplained in most cases, although it has been associated with mutations affecting the extra-cellular domain of the GH receptor in 1-5% of idiopathic short stature (ISS) children and adults, with mutations in Stat5b, with mutations in the acid labile subunit (ALS), or with mutations or polymorphisms in the IGF-1 gene itself.

GH deficiency is well recognized as a disease requiring replacement therapy with GH in children to treat short stature and in adults to correct body composition, bone density, cardiovascular function, and well being. By contrast, low IGF-1 levels, in the presence of normal GH secretion, has been previously usually associated only with a rare disease, recognized as Laron syndrome or growth hormone insensitivity syndrome (GHIS).

Most patients with Laron syndrome or GHIS lack growth hormone receptor binding activity and have absent or very low GH-binding protein (GHBP) activity in blood. Such patients are extremely short and have a mean height standard deviation score (SDS) of about −5 to −6, are resistant to GH treatment, and have increased serum concentrations of GH and low serum concentrations of IGF-1. As children they show a statural growth response to treatment with IGF-1.

The disease of short stature due to partial GH receptor defects was traditionally seen as primarily a disease characterized by a low GHBP level rather than a low IGF-1 level, with IGF-1 levels being only at the low end of the normal range. Specifically, the patient is defined as having a height of at least about 2 standard deviations or more below the normal mean for a corresponding age and gender (at least −2.0 SD below the mean), a serum level of high-affinity growth hormone binding protein that is at least 2 standard deviations below normal mean levels, a serum level of IGF-1 that is below normal mean levels, and a serum level of growth hormone that is at least normal.

The importance of this classification of the various factors affecting short stature is shown in the relative numbers of patients who are: 1) IGF-1 deficient and GH deficient and 2) IGF-1 deficient and GH sufficient. Current literature would predict that many more children and adults would be IGF-1 deficient due to GH deficiency than would be IGF-1 deficient and GH sufficient.

The therapeutic use of IGF-1 is well known and well studied. However, optimal delivery methods for the use of IGF-1 have not been developed. In human therapy, there is debate as to the optimal dose regimen of administration. At present, the accepted mode of delivery is twice daily dosing of IGF-1 in children with complete GH resistance (patients with Laron-type syndrome) or complete GH deficiency (GH gene deletion children). These patient groups have either a complete lack of GH action or a complete lack of the GH protein due to the GH gene being non-functional However, in patients who are not completely GH deficient or completely GH resistant, there is less information on how to dose with IGF-1 to achieve optimal efficacy. In the study reported by Bucuvalas, et al. {Bucuvalas, 2001 #371}, twice daily IGF-1 dosing was administered to patients with intact GH secretion and relatively normal IGFBP-3 levels. Bucuvalas, et al. used a dose of 80 micrograms IGF-1/kg patient bodyweight, the standard therapeutic dose used to treat children suffering from complete GH resistance. Bucuvalas, et al. found no significant increase in the growth rate of treated children. Bucuvalas, et al. reported that the growth velocity in the treated children was 6.0±1.9, and the growth velocity in the control group was 5.0±1.7, cm/year. Since no statistically significant improvement in growth was reported by Bucuvalas, et al., an effective IGF-1 dosing regimen for growth promotion has yet to be established for patients who are not completely GH resistant or GH deficient. In GH and IGF-1 deficient animals it has been shown that the more frequently rhIGF-1 is injected, the greater the growth response. However there appears to be no data in the literature on the efficacy of rhIGF-1 injection regimens on body growth in animals with intact GH secretion.

Osteoporosis, or porous bone, is a disease characterized by low bone mass and structural deterioration of bone tissue, leading to bone fragility and an increased susceptibility to fractures of the hip, spine, and wrist. It is a devastating disease among both postmenopausal women as well as among older men. The direct medical cost of osteoporosis is currently estimated to be over $13.8 billion per year. Unless interventions are begun immediately, the aging U.S. population will drive this cost up to an estimated $60 billion per year by year 2020. (available on the world wide web at nof.org/advocacy/leg_issue_briefs/Dec_99_advocacy.htm). At present, the mainstays of therapy are oral calcium supplements, vitamin D supplements, and a family of medications termed "anti-resorptives" which reduce osteoclastic bone resorption. These include estrogens, such as conjugated estrogens (Premarin™); selective estrogen receptor modulators (SERMs), such as raloxifene (Evista™); calcitonin (Miacalcin™); and bisphosphonates, such as alendronate (Fosamax™), risedronate (Actonel™), etidronate (Didronel™), pamidronate (Aredia™), tiludronate (Skelid™), or zoledronic acid (Zometa™). See, The writing group for the PEPI trial, JAMA 276: 1389-1396 (1996); Delmas et al., N Engl J Med 337: 1641-1647 (1997); Chestnut et al., Osteoporosis hit 8 (suppl 3): 13 (1998); Liberman et al., N Engl J Med 333: 1437-1443 (1995); McClung et al., N Engl J Med 344: 333-40 (2001). These drugs are effective in slowing bone mineral loss and even cause moderate increases in lumbar spine bone mineral density in the range of 2% (calcium, vitamin D, calcitonin), 3% (raloxifene), 6% (estrogens) or 8% (bisphosphonates). In general, two to three years of administration are required to achieve effects of this magnitude. See, The writing group for the PEPI trial, JAMA 276: 1389-1396 (1996); Delmas et al., N Engl J Med 337: 1641-1647 (1997); Chestnut et al., Osteoporosis Int 8 (suppl 3): 13 (1998); Liberman et al., N Engl J Med 333: 1437-1443 (1995); McClung et al., N Engl J Med 344: 333-40 (2001).

Osteoporosis exists, in general, when skeletal mineral losses result in a bone mass that is in the range of 50% below the peak bone mass. Peak bone mass occurs at approximately age 30. Seen from the perspective of correcting the deficit in bone mineral, complete reversal of this 50% loss would require a 100% increase in bone mass. Thus, the 2-8% increases in bone mineral density which result from anti-resorptive therapy, while clinically significant and beneficial, leaves very significant room for improvement. Since the use of anti-resorptives to prevent bone loss does not result in significant new bone production, the ultimate effectiveness of anti-resorptives in quantitative terms is limited. These considerations emphasize the need for the development of pharmaceutical mechanisms to produce new bone.

Osteoporosis is defined operationally by the National Osteoporosis Foundation and World Health Organization as a bone density that falls –2.0 or –2.5 standard deviations (SD) below the mean for lifetime peak bone density achieved in gender-matched and race-matched normal young adults (aged 20-25 years) (also referred to as a T-score of –2.0 or –2.5). Those who fall at the lower end of the gender-matched and race-matched normal young adult range (a T-score of >1 SD below the mean) have low bone density and are considered to be "osteopenic" and be at increased risk of osteoporosis.

IGF-1 is the primary protein hormone mediating the growth promoting effects of GH on bone. IGF-1 is produced in response to GH and then induces subsequent cellular responses, including cellular responses in bone.

IGF-1 plays a central role in bone formation. During mammalian growth GH induces IGF-1 expression in the liver and the skeleton. This endocrine and local IGF-1 causes bone growth via the epiphyseal growth plate chondrocytes and the expansion of the outer cortical envelope via periosteal osteoblasts. GH-induced expression of IGF-1 in the trabecular compartment of the skeleton may also recruit stromal cells into the bone lineage and the terminal differentiation of endosteal osteoblasts. Therefore in response to GH, each of these three skeletal components (the growth plate, the periosteum, and the endosteum) responds to IGF-1. Finally, this newly formed bone matrix becomes fully mineralized which ends skeletal maturation. Thus, IGF-1 plays a pivotal role in processes that include lifelong bone remodeling in the adult. Therefore, if a human or animal is GH resistant or IGF-1 deficient these processes are slowed so that bone length and statural height are reduced and bone structure compromised. The administration of rhIGF-1 in animals has been shown to correct such deficits in cartilage and bone growth and in bone structure.

Significant bone loss occurs in patients suffering from anorexia nervosa. Furthermore, bone loss is permanent in a significant number of anorexia nervosa patients despite weight recovery. The nutritional stress in patients suffering from anorexia nervosa adversely affects the growth hormone/IGF-1 axis and creates an IGF-1 deficiency that can contribute to severe bone loss in this population.

The administration of rhIGF-1 in mouse models of IGF-1 deficiency has been shown to correct such deficits in cartilage and bone growth and in bone structure Yakar, S., C. J. Rosen, et al., *J. Clin. Invest.,* 110(6): 771-81 (2002). In the ovariectomized rat, a model of osteoporosis, the administration of rhIGF-1 has increased cortical and trabecular bone and increased bone strength in the rat (Ammann, P., R. Rizzoli, et al., *Osteoporos. Int.,* 6(3): 219-27 (1996) (Verhaeghe, J., E. Van Herck, et al., *Growth Regul.* 5(4): 210-7 (1995)) (Verhaeghe, J., R. van Bree, et al., *J. Bone Miner. Res.,* 11(11): 1723-35 (1996)) (Mueller, K., R. Cortesi, et al., *Am. J. Physiol.,* 267(1 Pt 1): E1-6 (1994)) (Bagi, C., M. van der Meulen, et al., *Bone,* 16(5): 559-65 (1995)) and in the dog (U.S. Pat. No. 6,358,925).

Grinspoon, et al., "Effects of Recombinant Human IGF-1 and Oral Contraceptive Administration on Bone Density in Anorexia Nervosa," *J. Clin. Endo. Metab.,* 87: 2883-2891 (2002) reported the results of a clinical study of IGF-1 therapy in patients suffering from anorexia nervosa and bone loss characterized by osteopenia and/or osteoporosis. The study results indicated that (i) IGF-1 monotherapy prevented a loss of bone mineral density and (ii) IGF-1/estrogen combination therapy achieved an increase in bone mineral density compared to pre-treatment baseline values in patients suffering from anorexia nervosa and bone loss.

Cachexia is a multi-factorial disease of increased neurohormonal activity and immune abnormalities, resulting in hormonal and metabolic catabolic/anabolic imbalance of the body, leading to the loss of fat and lean mass and ultimately death. The physiological, metabolic, and behavioral changes in cachexia are associated with patient complaints of weakness, fatigue, gastrointestinal distress, sleep/wake disturbances, pain, listlessness, shortness of breath, lethargy, depression, malaise and the fear of being a burden on family and friends. Although cachexia has been classically associated with chronic diseases such as heart failure, termed cardiac cachexia, infections and malignant conditions, it has also been identified in patients after extensive traumatic injury and sepsis, and in aging persons with failure to thrive syndrome.

Muscle cachexia, mainly reflecting degradation of myofibrillar proteins, is an important clinical feature in cachectic patients. A redistribution of the body's protein content occurs, with preferential depletion of skeletal muscle and an increase in the synthesis of proteins involved in the response to tissue injury. Muscle cachexia is associated with increased gene expression and activity of the calcium/calpain and ubiquitin/proteasome-proteolytic pathways. Calcium/calpain-regulated release of myofilaments from the sarcomere is an early, and perhaps rate-limiting, component of the catabolic response in muscle. Understanding the mechanisms regulating muscle protein breakdown is important for the development of therapeutic strategies aimed at preventing and managing muscle cachexia. The catabolic response in skeletal muscle may result in muscle wasting and weakness that has important clinical implications such as difficulty with ambulation, impaired rehabilitation and increased risk for pulmonary complications.

The cachexia-anorexia syndrome involves metabolic pathology and is associated with hypertriacylglycerolemia, lipolysis, and acceleration of protein turnover. These changes result in the loss of fat mass and body protein. Increased resting energy expenditure in weight-losing cachectic patients can occur despite the reduced dietary intake, indicating systemic dysregulation of host metabolism. Cachexia, regardless of the underlying diagnosis, can rarely be explained by the actual energy and substrate demands or by the diagnosis itself. Cachexia involves immune changes, and cytokines have been identified in the development and/or progression of the cachexia-anorexia syndrome. For example, interleukin-1, interleukin-6 (and its subfamily such as ciliary neurotrophic factor and leukemia inhibitory factor), interferon-gamma, tumor necrosis factor-alpha, and brain derived neurotrophic factor have been associated in various cachectic conditions.

It is the object of this invention to show that there are unexpected differences in the responses of various patient groups to various IGF-1 treatment modalities. An optimal dose-regimen is disclosed for stimulating growth using IGF-1.

In addition, from reports of the co-administration of IGF-1 and GH, K-O mouse data and biochemical evidence it appears there are synergistic or greater than additive effects of the combination of GH and IGF-1. It is an object of this invention to demonstrate how with the administration of IGF-1 that this synergism or greater than additive activity can be maintained or enhanced utilizing the GH that is endogenously produced. Another object of the invention is to show that with certain modes and injection schemes of IGF-1 that endogenous GH secretion can be preserved or enhanced and so GH activity can be preserved and synergy or greater than additive activity due to the combination of GH and IGF-1 can be maintained or enhanced.

Literature

Literature of interest includes: U.S. Pat. No. 5,824,642; Salmon W D Jr. et al., 1957, J Lab Olin Med, 49:825-36; Liu, J-L and LeRoith, D, 1999, Endocrinology 140:5178-84; Lupu, F et al., 2001, Dev Biol 229:141-62; Zhou, Y et al., 1997, Proc Natl Acad Sci USA 94:13215-20; and Juul, 2003, GH and IGF Research 13: 113-170. Van Wyk J J. The Somatomedins: biological actions and physiological control mechanisms in Hormonal Proteins and Peptides, ed C H Li, 12:81-175, Orlando, Fla.: Academic Press; Clemmons D R et al., 1984, Clin Endocrinol Metab 13:113-43; Clemmons D R et al., 1979, N Engl J Med 301:1138-42; Clemmons D R et al., 1986, Olin Endocrinol Metal 15:629-51; Liu, J-L and LeRoith, D, 1999, Endocrinology 140:5178-84; Lupu, F et al., 2001, Dev Biol 229:141-62; Zhou, Y et al., 1997, Proc Natl Acad Sci USA 94:13215-20; U.S. Pat. No. 6,358,925; Ammann, P., R. Rizzoli, et al. (1996). "Bone density and shape as determinants of bone strength in IGF-I and/or pamidronate-treated ovariectomized rats." Osteoporos Int 6(3): 219-27; Bikle, D. D., T. Sakata, et al. (2002). "Insulin-like growth factor I is required for the anabolic actions of parathyroid hormone on mouse bone." J Bone Miner Res 17(9): 1570-8; Gamero, P., E. Sornay-Rendu, et al. (2000). "Low serum IGF-1 and occurrence of osteoporotic fractures in postmenopausal women." Lancet 355(9207): 898-9; Golden, N. H., E. A. Iglesias, et al. (2005). "Alendronate for the treatment of osteopenia in anorexia nervosa: a randomized, double-blind, placebo-controlled trial." J Clin Endocrinol Metab 90(6): 3179-85; Golden, N. H., L. Lanzkowsky, et al. (2002). "The effect of estrogen-progestin treatment on bone mineral density in anorexia nervosa." J Pediatr Adolesc Gynecol 15(3): 135-43; Grinspoon, S., H. Baum, et al. (1996). "Effects of short-term recombinant human insulin-like growth factor I administration on bone turnover in osteopenic women with anorexia nervosa." J Clin Endocrinol Metab 81(11): 3864-70; Grinspoon, S., E. Thomas, et al. (2000). "Prevalence and predictive factors for regional osteopenia in women with anorexia nervosa." Ann Intern Med 133(10): 790-4; Grinspoon, S., L. Thomas, et al. (2002). "Effects of recombinant human IGF-I and oral contraceptive administration on bone density in anorexia nervosa." J Clin Endocrinol Metab 87(6): 2883-91; Hoek, H. W. and D. van Hoeken (2003). "Review of the prevalence and incidence of eating disorders." Int J Eat Disord 34(4): 383-96; Kasukawa, Y., D. J. Baylink, et al. (2003). "Lack of insulin-like growth factor I exaggerates the effect of calcium deficiency on bone accretion in mice." Endocrinology 144(11): 4682-9; Kurland, E. S., C. J. Rosen, et al. (1997). "Insulin-like growth factor-I in men with idiopathic osteoporosis." J Clin Endocrinol Metab 82(9): 2799-805; Langlois, J. A., C. J. Rosen, et al. (1998). "Association between insulin-like growth factor I and bone mineral density in older women and men: the Framingham Heart Study." Clin Endocrinol Metab 83(12): 4257-62; Lucas, A. R., L. J. Melton, 3rd, et al. (1999). "Long-term fracture risk among women with anorexia nervosa: a population-based cohort study." Mayo Clin Proc 74(10): 972-7; Miller, K. K., K. A. Grieco, et al. (2004). "Effects of risedronate on bone density in anorexia nervosa." J Clin Endocrinol Metab 89(8): 3903-6; Miller, K. K., S. K. Grinspoon, et al. (2005). "Medical findings in outpatients with anorexia nervosa." Arch Intern Med 165(5): 561-6; Munoz, M. T., G. Morande, et al. (2002). "The effects of estrogen administration on bone mineral density in adolescents with anorexia nervosa." Eur J Endocrinol 146(1): 45-50; Nakaoka, D., T. Sugimoto, et al. (2001). "Determinants of bone mineral density and spinal fracture risk in postmenopausal Japanese women." Osteoporos Int 12(7): 548-54; Rigotti, N. A., R. M. Neer, et al. (1991). "The clinical course of osteoporosis in anorexia nervosa. A longitudinal study of cortical bone mass." Jama 265(9): 1133-8; Rivadeneira, F., J. J. Houwing-Duistermaat, et al. (2004). "The influence of an insulin-like growth factor I gene promoter polymorphism on hip bone geometry and the risk of nonvertebral fracture in the elderly: the Rotterdam Study." J Bone Miner Res 19(8): 1280-90; Vahle, J. L., M. Sato, et al. (2002). "Skeletal changes in rats given daily subcutaneous injections of recombinant human parathyroid hormone (1-34) for 2 years and relevance to human safety." Toxicol Pathol 30(3): 312-21; Yager, J. and A. E. Andersen (2005). "Clinical practice. Anorexia nervosa." N Engl J Med 353(14): 1481-8; Yakar, S., C. J. Rosen, et al. (2002). "Circulating levels of IGF-1 directly regulate bone growth and density." J Clin Invest 110(6): 771-81; Zhang, M., S. Xuan, et al. (2002). "Osteoblast-specific knockout of the insulin-like growth factor (IGF) receptor gene reveals an essential role of IGF signaling in bone matrix mineralization." J Biol Chem 277(46): 44005-12.

SUMMARY OF THE INVENTION

The present invention provides methods and compositions for increasing the growth rates, alleviating the symptoms, or improving the metabolism of human patients having an endocrine disorder characterized by partial endogenous growth hormone activity or signaling. The invention relates to methods for promoting growth in a pediatric patient having a height which, at the time of treatment or prior to initial treatment, is at least about 2 standard deviations (SD) below the normal mean for the corresponding age and gender of the patient. The invention also relates to methods for improving metabolism in an adult patient having an endocrine disorder characterized by partial endogenous growth hormone activity or signaling, wherein the patient is further characterized by having suffered from a growth disorder characterized by partial endogenous growth hormone activity or signaling during childhood.

In one aspect, the invention provides a method comprising administering to a pediatric patient suffering from a growth disorder characterized by partial endogenous growth hormone activity or signaling an amount of insulin-like growth factor-1 (IGF-1) effective to promote growth in the patient, wherein the patient receives the amount of IGF-1 in a single administration per day.

In another aspect, the invention provides a method comprising administering to a pediatric patient suffering from a growth disorder characterized by partial endogenous growth hormone activity or signaling an amount of insulin-like growth factor-1 (IGF-1) and an amount of growth hormone (GH) that are effective in combination therapy to promote growth in the patient, wherein the patient receives the amount of IGF-1 in a single administration per day and receives the amount of GH in a single administration per day, and wherein the patient receives the administrations of IGF-1 and GH contemporaneously or substantially contemporaneously.

In another aspect, the invention provides a method comprising administering to an adult patient suffering from an endocrine disorder characterized by partial endogenous growth hormone activity or signaling an amount of insulin-like growth factor-1 (IGF-1) effective to improve metabolism in the patient, wherein the patient is further characterized by having suffered from a growth disorder characterized by partial endogenous growth hormone activity or signaling during, childhood, and wherein the patient receives the amount of IGF-1 in a single administration per day.

In another aspect, the invention provides a method comprising administering to an adult patient suffering from an endocrine disorder characterized by partial endogenous growth hormone activity or signaling an amount of insulin-like growth factor-1 (IGF-1) and an amount of growth hormone (GH) that are effective in combination therapy to improve metabolism in the patient, wherein the patient is further characterized by having suffered from a growth disorder characterized by partial endogenous growth hormone activity or signaling during childhood, wherein the patient receives the amount of IGF-1 in a single administration per day and receives the amount of GH in a single administration per day, and wherein the patient receives the administrations of IGF-1 and GH contemporaneously or substantially contemporaneously.

In another aspect, the invention provides a method comprising administering to a patient suffering from a physiological stress-induced endocrine disorder characterized by partial endogenous growth hormone activity or signaling, an amount of insulin-like growth factor-1 (IGF-1) effective to improve a metabolic abnormality in the patient, and wherein the patient receives the amount of IGF-1 in a single administration per day.

In another aspect, the invention provides a method comprising administering to a patient suffering from a physiological stress-induced endocrine disorder characterized by partial endogenous growth hormone activity or signaling an amount of insulin-like growth factor-1 (IGF-1) and an amount of growth hormone (GH) that are effective in combination therapy to improve a metabolic abnormality in the patient, wherein the patient receives the amount of IGF-1 in a single administration per day and receives the amount of GH in a single administration per day, and wherein the patient receives the administrations of IGF-1 and GH contemporaneously or substantially contemporaneously.

In another aspect, the invention provides a method comprising administering to a patient suffering from cachexia an amount of insulin-like growth factor-1 (IGF-1) effective to improve nitrogen balance or increase body weight or lean body mass in the patient, and wherein the patient receives the amount of IGF-1 in a single administration per day.

In another aspect, the invention provides a method comprising administering to a patient suffering from cachexia an amount of insulin-like growth factor-1 (IGF-1) and an amount of growth hormone (GH) that are effective in combination therapy to improve nitrogen balance or increase body weight or lean body mass in the patient, wherein the patient receives the amount of IGF-1 in a single administration per day and receives the amount of GH in a single administration per day, and wherein the patient receives the administrations of IGF-1 and GH contemporaneously or substantially contemporaneously.

In another aspect, the invention provides a method comprising administering to a patient suffering from anorexia an amount of insulin-like growth factor-1 (IGF-1) that is effective to improve a metabolic abnormality in the patient, wherein the patient receives the amount of IGF-1 in a single administration per day. In some embodiments, the patient suffering from anorexia is weight recovering but not weight recovered. In any of the foregoing embodiments, the patient's anorexic disorder can be anorexia nervosa. In addition, the invention contemplates a modification of the above-described method of treating anorexia in which the improvement in metabolism is an improvement in the nitrogen balance or an increase in the body weight or lean body mass of the patient. In addition, the invention contemplates a modification of the above-described method of treating anorexia in which the improvement in metabolism is an improvement in bone metabolism and in which the method further comprises administering to the patient an amount of an anti-resorptive agent such as estrogen that, in combination with the amount of IGF-1 administered according to the method, is effective to improve bone metabolism in the patient. In any of these embodiments, the improvement in bone metabolism can be an improvement in the bone mineral density (BMD) of the patient. In any of the foregoing embodiments, the patient can be a human female.

In another aspect, the invention provides a method comprising administering to a patient suffering from anorexia an amount of insulin-like growth factor-1 (IGF-1) and an amount of growth hormone (GH) that are effective in combination therapy to improve a metabolic abnormality in the patient, wherein the patient receives the amount of IGF-1 in a single administration per day and receives the amount of GH in a single administration per day, and wherein the patient receives the administrations of IGF-1 and GH contemporaneously or substantially contemporaneously. In some embodiments, the patient suffering from anorexia is weight recovering but not weight recovered. In any of the foregoing embodiments, the patient's anorexic disorder can be anorexia nervosa. In addition, the invention contemplates a modification of the above-described method of treating anorexia in which the improvement in metabolism is an improvement in the nitrogen balance or an increase in the body weight or lean body mass of the patient. In addition, the invention contemplates a modification of the above-described method of treating anorexia in which the improvement in metabolism is an improvement in bone metabolism and in which the method further comprises administering to the patient an amount of an anti-resorptive agent such as estrogen that, in combination with the amounts of IGF-1 and GH administered according to the method, is effective to improve bone metabolism in the patient. In any of these embodiments, the improvement in bone metabolism can be an improvement in the bone mineral density (BMD) of the patient. In any of the foregoing embodiments, the patient can be a human female.

In addition, the invention contemplates a modification of each of the above-described methods in which whatever IGF-1 administration is specified in the subject method is administered to the patient in a single administration of an immediate release formulation of IGF-1, and whatever IGF-1 and GH administration combination is specified in the subject method is (a) administered to the patient in a single administration of an immediate release co-formulation of IGF-1 and GH, (b) administered to the patient in a single administration of an immediate release formulation of IGF-1 and in a single administration of a separate immediate release formulation of GH, or (c) administered to the patient in a single administration of an immediate release formulation of IGF-1 and a separate immediate release formulation of GH that are admixed prior to such administration.

DEFINITIONS

Before describing the invention in greater detail, the following definitions are set forth to illustrate and define the meaning and scope of the terms used to describe the invention herein.

As used herein, "patient" refers to any mammal, including humans, bovines, ovines, porcines, canines and felines, in need of treatment. In certain embodiments, the patient is a human. In general, the methods of the invention are applicable to pediatric and adult patients.

As used herein, "insulin-like growth factor-1 deficiency", "IGF-1 deficiency", or "IGFD" refer to a condition associated with the following characteristics, a height of at least about 2 standard deviations (SD) below the normal mean level for the corresponding age and gender, a blood level of IGF-1 that is at least below normal mean levels. In general, IGFD can be due to a resistance to GH action or as a result of GH deficiency (GHD). IGFD that is due to resistance to GH action is termed primary IGFD, while IGFD resulting from GHD is termed secondary IGFD. Primary IGFD is distinguished from secondary IGFD in that primary IGFD is associated with at least normal GH blood levels, while secondary IGFD is associated with low blood levels of GH.

Thus, primary IGFD refers to a condition associated with the following characteristics, a height of at least about 2 standard deviations (SD) below the normal mean for the corresponding age and gender, a blood level of IGF-1 that is below normal mean levels, and a basal or stimulated blood level of growth hormone (GH) that is at least normal (e.g., normal GH blood levels or greater than normal GH blood levels). GHBP levels are generally within the normal range.

Pediatric primary IGFD refers to pediatric patients with IGFD, while Adult primary IGFD refers to adult patients with IGFD. Adult primary IGFD, is similar to pediatric primary IGFD, and if untreated in childhood, is associated with a height of at least 2 SD below the normal mean for the corresponding age and gender, a blood level of IGF-1 that is below the normal mean for the corresponding age and gender, and normal growth hormone levels. Adult primary IGFD patients have increased blood pressure, decreased cardiac performance, cardiac disease, renal disease impaired exercise performance, decreased muscle mass, decreased bone density, obesity and abnormalities of carbohydrate and lipid metabolism. Pediatric patients with primary IGFD are capable of having their height or growth rate increased, while adult patients are no longer capable of achieving a greater height unless treated in childhood. In certain embodiments, the subject methods encompass treating pediatric primary IGFD patients who do not have a blood level of high affinity growth hormone binding protein that is at least 2SDs below normal mean levels and do not have Laron syndrome.

The term "concentration in blood", such as in the phrases "IGF-1 concentration in blood" or "IGFBP-3 concentration in blood", refers to a concentration of an agent (e.g., IGF-1 or IGFBP-3) obtained in whole blood or in a fluid obtained from blood, such as plasma or serum.

As used herein, "short stature" means a subject who has a height standard deviation score of below about −2 SD, or in some embodiments below −2.25 SD, that of the normal mean height for an individual of the same age and gender.

As used herein, the term "Laron syndrome" refers to a patient exhibiting complete lack of growth hormone receptor (GHR) function or complete growth hormone insensitivity syndrome (GHIS). Such patients have a mean height standard deviation score (SDS) of on average about −5 to −6 and respond to treatment with IGF-1. In patients with defects in the extracellular domain of the GHR, the lack of functional GHBP in the circulation can serve as a marker for the GH insensitivity. Additional common symptoms of "Laron syndrome" include small face and jaw, depressed nasal bridge, frontal bossing, obesity, high-pitched voice, and hypoglycemia in early childhood. Biochemically, Laron syndrome patients are characterized by having increased blood concentrations of GH and low blood GHBP concentrations, but low blood concentrations of IGF-1.

As used herein, "idiopathic short stature," "ISS," and "non-GHD non-IGFD," all refer to a syndrome in a pediatric patient suffering from a growth disorder characterized by growth hormone sufficiency (i.e., normal GH blood levels or other evidence that GH secretion is normal), IGF-1 sufficiency (i.e., IGF-1 blood levels that are in the normal range for the patient's corresponding age and gender), and a height standard deviation score (SDS) of at least below about −2, or in some embodiments less than −2.25 SD, for the patient's corresponding age and gender.

As used herein, "partial growth hormone insensitivity syndrome", or "partial GHIS" refers to a syndrome wherein the patient responds to the same doses of GH as that given to GH-deficient patients, but does not respond as well. This syndrome is further characterized in that the patient has a height of at least about 2 standard deviations below the normal mean for a corresponding age and gender, preferably in the range of about 2 to about 4 standard deviations or more below the normal mean for a corresponding age and gender (e.g., a height SD score of −2.0 to −4.0), has a blood level of high-affinity GHBP that is at least 2 standard deviations (typically about 2 to about 4 standard deviations) below the normal mean level for humans, has a blood level of IGF-1 that is below the normal mean level for humans, and has a mean or maximum stimulated blood level of GH that is at least normal. Mean blood levels are the mean of measurements in the patient.

As used herein, a growth disorder in a pediatric patient characterized by "partial endogenous growth hormone activity or signaling," "partial endogenous GH activity or signaling," "partial growth hormone activity or signaling," or "partial GH activity or signaling" refers to a syndrome wherein the patient is characterized by (i) a height, prior to therapeutic treatment of the growth disorder, of at least about 2 standard deviations below the normal mean for the corresponding age and gender of the patient, preferably in the range of about 2 to about 4 standard deviations or more below the normal mean for the corresponding age and gender of the patient (e.g., a SD of −2.0 to −4.0) and (ii) an endocrine system that exhibits endogenous GH induction of IGF-1 and IGFBP-3. Generally, blood IGFBP-3 levels can serve as an indicator of endogenous growth hormone activity or signaling in a patient. A patient having partial endogenous growth hormone activity or signaling will exhibit a biphasic curve of IGFBP-3 blood level as a function of time in response to a single administration of exogenous IGF-1, in which the patient's IGFBP-3 blood level immediately rises following IGF-1 dosing, followed by a decay in IGFBP-3 blood levels to baseline or below by 12 to 16 hours post-dosing, in turn followed by a rebound in IGFBP-3 blood levels to above baseline by 24 to 36 hours post-dosing. An exemplary biphasic curve of IGFBP-3 blood levels over time following IGF-1 administration in moderate primary IGFD patients is shown in FIG. 7.

As used herein, an endocrine disorder in an adult patient characterized by "partial endogenous growth hormone activity or signaling," "partial endogenous GH activity signaling," "partial growth hormone activity or signaling," or "partial GH activity or signaling" refers to a syndrome wherein the patient is characterized by (i) having suffered from a growth disorder during childhood (ii) one or more metabolic conditions that is/are adult manifestations of the hormonal disturbance suffered by the patient during childhood and (iii) an endocrine system that exhibits endogenous GH induction of IGF-1 and IGFBP-3. Thus, a pediatric patient suffering from a growth disorder characterized by partial growth hormone activity or signaling can, with age, become an adult patient suffering from an endocrine disorder characterized by partial growth hormone activity or signaling.

As used herein, an endocrine disorder in any patient (including pediatric, adolescent and adult patients) that is described as: (A) "physiological stress-induced," "caused by physiological stress," "induced by physiological stress," "arising from physiological stress," "consequent to physiological stress," or "a sequela of physiological stress"; and (B) "characterized by partial endogenous growth hormone activity or signaling," "characterized by partial endogenous GH activity signaling," "characterized by partial growth hormone activity or signaling," or "characterized by partial GH activity or signaling"; refers to a syndrome wherein the patient is characterized by (i) an endocrine disorder that involves a dysregulation or disturbance of the GH/IGF-1 axis and that is caused by physiological stress, and (ii) an endocrine system that exhibits endogenous GH induction of IGF-1 and IGFBP-3. In addition, the definition applies whenever the term "endocrine disorder" is modified by phrases similar to those of (A) and (B) in the foregoing.

As used herein, a "physiological stress-induced" disorder, a disorder "caused by physiological stress," a disorder "induced by physiological stress," a disorder "arising from physiological stress," a disorder "consequent to physiological stress," a disorder "that is a sequela of physiological stress," and all phrases of similar meaning to any of the foregoing phrases, are used interchangeably herein to refer to any disorder suffered by a patient as: (i) a consequence of the patient's underlying disease state(s), e.g., cancer, infections, chronic inflammatory diseases such as rheumatoid arthritis, inflammatory bowel disease and Crohn's disease, respiratory syndromes such as cystic fibrosis, pulmonary fibrosis and chronic obstructive pulmonary disease (COPD), and cardiovascular diseases such as congestive heart failure, renal failure and the like; and/or (ii) a consequence of the patient's exposure to one or more environmental stresses, e.g., allergens, mutagens, carcinogens, pathogens, drugs, alcohol or other chemical agents, trauma, burns, smoking, systemic shock, surgery, and nutritional stress such as malnutrition and starvation, and the like.

As used herein, "anorexia nervosa" refers to an eating disorder in a patient characterized by determined dieting, often accompanied by compulsive exercise and resulting in dramatic weight loss. A disturbed body image and fear of fatness lead to a continued desire to lose more weight. Most cases of anorexia nervosa occur in women, usually beginning during adolescence (Yager and Anderson, N. Eng. J. Med., 353: 1481-1488 (2005)). The defining characteristics of anorexia nervosa are given in the *Diagnostic and Statistical Manual of Mental Disorders*, revised 4$^{th}$ edition (DSM-IV, REF), published by the American Psychiatric Association (Washington, D.C.: 2000) as follows:

1. Refusal to maintain body weight at or above a minimal normal weight for age and height (e.g., a weight loss resulting in maintenance of body weight less than 85% of ideal weight or failure to make the expected weight gain during the period of growth, resulting in a body weight of less than 85% of the ideal weight).

2. An intense fear of gaining weight or becoming fat, even though underweight.

3. A disturbance in the way in which body weight or shape is experienced (body dysmorphia), undue influence of body weight or shape on self-evaluation, or denial of the seriousness of current low body weight.

4. Among postmenarchal adolescent girls and adult women, amenorrhea (the absence of at least three consecutive menstrual cycles; amenorrhea is considered to be present if menstrual periods occur only after the administration of estrogen therapy).

As used herein, "osteoporosis" refers to a condition in which the patient exhibits a bone mineral density T-score of less than −2.5 at any skeletal site as described by Miller and Grinspoon, Arch. Intern. Med., 165: 561-566 (2005).

As used herein, "osteopenia" refers to a condition in which the patient exhibits a bone mineral density T-score of less than −1.0 at any skeletal site.

As used herein, "cachexia" refers to a progressive wasting syndrome characterized by extensive loss of adipose tissue and skeletal muscle in a patient who is not actively trying to lose weight. It can be a sequela of various underlying disorders, including cancer, certain infectious diseases (e.g. tuberculosis), acquired immunodeficiency syndrome (AIDS), congestive heart failure, renal failure, cystic fibrosis, rheumatoid arthritis, and Crohn's disease. Cachexia physically weakens patients to a state of immobility stemming from anorexia, asthenia, and anemia.

As used herein, the phrase "increasing the body weight or lean body mass of a patient," and all phrases similar to the foregoing phrase, refer to (i) a gain in body weight or lean body mass experienced by a patient in response to therapy in comparison to the baseline (pretreatment) body weight or lean body mass of the patient, or (ii) a reduction in or prevention of a loss of body weight or lean body mass experienced by a patient in response to therapy in comparison to the loss of body weight or lean body mass experienced by placebo-treated control patients or untreated control patients.

As used herein, the "nitrogen balance" of a patient is defined as the difference between the nitrogen intake (as protein or amino acids) in an individual and the total nitrogen excretion. When the nitrogen intake equals the nitrogen excretion, the subject is in nitrogen equilibrium. If the nitrogen intake exceeds the nitrogen excretion, the nitrogen balance is positive, but if the nitrogen excretion is greater than the nitrogen intake, the nitrogen balance is negative. Nitrogen balance can be estimated by monitoring urinary nitrogen. Absolute nitrogen balance also requires fecal nitrogen measurement, but in most cases this does not change appreciably unless the diet is substantially altered. Thus, the nitrogen content of urine can be approximately correlated with total nitrogen excretion. Monitoring nitrogen content of urine is especially important where the patient has or is expected to have a persistent negative nitrogen balance.

As used herein, "growth hormone" or "GH" refers to growth hormone in native-sequence or in variant form, and from any source, whether natural, synthetic, or recombinant. Examples include human growth hormone (hGH), which is natural or recombinant GH with the human native sequence (somatotropin or somatropin), and recombinant growth hormone (rGH), which refers to any GH or GH variant produced by means of recombinant DNA technology, including somatrem, somatotropin, and somatropin. Preferred herein for human use is recombinant human native-sequence, mature GH with or without a methionine at its N-terminus. More preferred is methionyl human growth hormone (met-hGH) produced in E. coli, e.g., by the process described in U.S. Pat. No. 4,755,465 issued Jul. 5, 1988 and Goeddel et al., Nature, 282: 544 (1979). Met-hGH, which is sold under the trademark PROTROPIN® by Genentech, Inc., is identical to the natural polypeptide, with the exception of the presence of an N-terminal methionine residue. This added amino acid is a result of the bacterial protein synthesis process. Also preferred is recombinant hGH available from Genentech, Inc. under the trademark NUTROPIN®. Additionally preferred is recombinant rhGH liquid for injection available from Genentech, Inc. under the trademark NUTROPIN AQ®. These latter two hGH products lack an N-terminal methionine residue and have an amino acid sequence identical to that of the natural hormone. See Gray et al., Biotechnology 2: 161 (1984). Both methionyl hGH and hGH have equivalent potencies and pharmacokinetic values. Moore et al., Endocrinology, 122: 2920-2926 (1988). Another appropriate hGH candidate is an hGH variant that is a placental form of GH with pure somatogenic and no lactogenic activity as described in U.S. Pat. No. 4,670,393 issued 2 Jun. 1987. Also included are GH variants as described in WO 90/04788 published 3 May 1990 and WO 92/09690 published 11 Jun. 1992.

As used herein, "IGF-1" refers to insulin-like growth factor-1 from any species, including bovine, ovine, porcine, equine, avian, and preferably human, in native-sequence or in variant form, and from any source, whether natural, synthetic, or recombinant.

Suitable for use in the subject methods is human native-sequence, mature IGF-1, for example, without an N-terminal methionine, prepared, e.g., by the process described in EP 230,869 published Aug. 5, 1987; EP 128,733 published Dec. 19, 1984; or EP 288,451 published Oct. 26, 1988. More preferably, this native-sequence IGF-1 is recombinantly produced as described in EP 123,228 and 128,733, and U.S. Pat. No. 6,331,414 issued Dec. 18, 2001. Still more preferably, this native-sequence IGF-1 is the active pharmaceutical ingredient in the drug product commercially marketed as INCRELEX™ (mecasermin [rDNA origin] for injection). The term "rhIGF-1" refers to recombinant human IGF-1.

As used herein, reference to "variants" or "analogs, homologs and mimics" of IGF-1 embraces compounds which differ from the structure of native IGF-1 by as little as the replacement and/or deletion of one or more residues thereof, to compounds which have no apparent structural similarity. Such compounds in all instances, however, have substantially the same activity as native IGF-1. Thus, "analogs" refers to compounds having the same basic structure as IGF-1, but differing in several residues; and "homologs" refers to compounds which differ from native IGF-1 by the deletion and/or replacement of a limited number of residues.

Suitable for use in the present invention are IGF-1 variants described in U.S. Pat. Nos. 5,077,276 issued Dec. 31, 1991; 5,164,370; 5,470,828; in PCT WO 87/01038 published Feb. 26, 1987 and in PCT WO 89/05822 published Jun. 29, 1989, i.e., those wherein at least the glutamic acid residue is absent at position 3 from the N-terminus of the mature molecule or those having a deletion of up to five amino acids at the N-terminus. The most preferred variant has the first three amino acids from the N-terminus deleted (variously designated as brain IGF, tIGF-1, des(1-3)-IGF-1, or des-IGF-1). Other compounds are the IGF-1 displacers compounds as described below, and in U.S. Pat. Nos. 6,121,416, 6,251,865, and 6,420,518.

As used herein, an "IGF binding protein" or "IGFBP" refers to a protein or polypeptide normally associated with or bound or complexed to IGF-1 or IGF-2, whether or not it is circulatory (i.e., in blood (e.g., serum) or tissue). Such binding proteins do not include receptors. This definition includes IGFBP-1, IGFBP-2, IGFBP-3, IGFBP-4, IGFBP-5, IGFBP-6, Mac 25 (IGFBP-7), and prostacyclin-stimulating factor (PSF) or endothelial cell-specific molecule (ESM-1), as well as other proteins with high homology to IGFBPs. Mac 25 is described, for example, in Swisshelm et al., 1995, Proc Natl Acad Sci USA, 92: 4472-4476 and Oh et al., J Biol Chem, 271: 30322-30325 (1996). PSF is described in Yamauchi et al., 1994, Biochem J, 303:591-598. ESM-1 is described in Lassalle et al., 1996, J Biol Chem, 271: 20458-20464. For other identified IGFBPs, see, e.g., EP 375,438 published Jun. 27, 1990; EP 369,943 published May 23, 1990; WO 89/09268 published Oct. 5, 1989; Wood et al., 1988, Mol Endocrinol, 2: 1176-1185; Brinkman et al., 1988, EMBO J, 7: 2417-2423; Lee et al., 1988, Mol Endocrinol, 2:404-411; Brewer et al., 1988, Biochem Biophys Res Comm, 152: 1289-1297; EP 294,021 published Dec. 7, 1988; Baxter et al., 1987, Biochem Biophys Res Comm, 147: 408-415; Leung et al., 1987, Nature, 330: 537-543; Martin et al., 1986, J Biol Chem, 261:8754-8760; Baxter et al., 1988, Comp Biochem Physiol, 91B: 229-235; WO 89/08667 published Sep. 21, 1989; WO 89/09792 published Oct. 19, 1989; and Binkert et al., 1989, EMBO J, 8: 2497-2502.

As used herein, "active", "bioactive", "biologically active" or "free" IGF-1 in the context of changing blood and tissue levels of endogenous IGF-1 refers to IGF-1 that binds to an IGF receptor or an insulin receptor, or a hybrid IGF/insulin receptor, or to an IGF binding protein, or otherwise causes a biological activity of endogenous or exogenous. IGF-1 to occur.

As used herein, "high-affinity growth hormone binding protein" or "high-affinity GHBP" refers to the extracellular domain of the GHR that circulates in blood and functions as a GHBP in several species (Ymer et al., 1985, Mol. Cell. Endocrinol. 41:153; Smith et al., 1988, Endocrinology 123: 1489-1494; Emtner et al., 1990, Acta Endocrinologica (Copenh.), 122:296-302), including man (Baumann et al., 1986, J. Clin. Endocrinol. Metab., 62:134-141; EP 366,710 published 9 May 1990; Herington et al., 1986, J. Clin. Invest., 77:1817-1823; Leung et al., 1987, Nature 330:537-543. A second BP with lower affinity for GH has also been described that appears to be structurally unrelated to the GHR (Baumann et al., 1990, J. Clin. Endocrinol. Metab. 70:680-686. Various methods exist for measuring functional GHBP in blood, with the preferred method being a ligand-mediated immunofunctional assay (LIFA) described by Carlsson et al. (1991, J. Clin. Endocrinol. Metab. 73:1216) and U.S. Pat. No. 5,210,017.

As used herein, "increasing the growth rate of a patient" includes not only the situation where the patient attains a similar ultimate height as GH-deficient patients treated with GH (i.e., patients diagnosed with GHD) or IGF-1 deficient patients treated with IGF-1, but also refers to a situation where the patient catches up in height at a similar growth rate as GH-deficient patients treated with GH or IGF-1 deficient patients treated with IGF-1, or achieves adult height that is close to the target height range, i.e., an ultimate height more consistent with their genetic potential as determined by the mid-parental target height, or increases their height typically measured by a growth rate (in cm/year) or by an increase in the height SD score.

As used herein, "alleviating a symptom of an endocrine disorder characterized by partial endogenous growth hormone activity or signaling" refers to achieving a therapeutic benefit for a symptom associated with an endocrine disorder characterized by partial endogenous growth hormone activity or signaling. Symptoms of patients suffering from endocrine disorders characterized by partial endogenous growth hormone activity or signaling include, but are not limited to, decreased growth rate or height SDS, increased blood pressure, decreased cardiac performance, cardiac disease, renal disease, neurological disease, impaired exercise performance, decreased muscle mass, decreased bone density, obesity and abnormalities of carbohydrate and lipid metabolism. Thus, alleviating symptoms of an endocrine disorder characterized by partial endogenous growth hormone activity or signaling results in increased growth rates, increased height SDS, increased bone mineral density, improved bone structure, improved renal and cardiac function, and improved glucose control and body composition.

As used herein, "treatment" or "treating" refers to inhibiting the progression of a disease or disorder, e.g., short stature or other endocrine disorder characterized by partial endogenous growth hormone activity or signaling, or delaying the onset of a disease or disorder, e.g., short stature or other endocrine disorder characterized by partial endogenous growth hormone activity or signaling, whether physically, e.g., stabilization of a discernible symptom, physiologically, e.g., stabilization of a physical parameter, or both. As used herein, the terms "treatment," "treating," and the like, refer to obtaining a desired pharmacologic and/or physiologic effect. The effect may be prophylactic in terms of completely or partially preventing a disease or condition, or a symptom thereof and/or may be therapeutic in terms of a partial or complete cure for a disease or disorder and/or adverse affect attributable to the disease or disorder. "Treatment," as used herein, covers any treatment of a disease or disorder in a mammal, such as a human, and includes: decreasing the risk of death due to the disease; preventing the disease of disorder from occurring in a subject which may be predisposed to the disease but has not yet been diagnosed as having it; inhibiting the disease or disorder, i.e., arresting its development (e.g., reducing the rate of disease progression); and relieving the disease, i.e., causing regression of the disease. Therapeutic benefits of the present invention include, but are not necessarily limited to, reduction of risk of onset or severity of disease or conditions associated with short stature or other endocrine disorder characterized by partial endogenous growth hormone activity or signaling.

As used herein, a "therapeutically effective amount" refers to that amount of the compound sufficient to treat or manage a disease or disorder, e.g., short stature or other endocrine disorder characterized by partial endogenous growth hormone activity or signaling. A therapeutically effective amount may refer to the amount of a compound that provides a therapeutic benefit in the treatment or management of a disease or disorder. Further, a therapeutically effective amount with respect to a compound of the invention means that amount of compound alone, or in combination with other therapies, that provides a therapeutic benefit in the treatment or management of a disease or disorder. The term can encompass an amount that improves overall therapy, reduces or avoids unwanted effects, or enhances the therapeutic efficacy of or synergies with another therapeutic agent.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, subcutaneous, intradermal, intratracheal and the like. In some embodiments the composition is suitable for administration by a transdermal route, using a penetration enhancer other than DMSO. In other embodiments, the pharmaceutical compositions are suitable for administration by a route other than transdermal administration.

As used herein, the phrase "pharmaceutically acceptable carrier" refers to a carrier medium that does not interfere with the effectiveness of the biological activity of the active ingredient. Said carrier medium is essentially chemically inert and nontoxic.

As used herein, the phrase "pharmaceutically acceptable" means approved by a regulatory agency of the Federal government or a state government, or listed in the U.S. Pharmacopeia or other generally recognized pharmacopeia for use in animals, and more particularly for use in humans.

As used herein, the term "carrier" refers to a diluent, adjuvant, excipient, or vehicle with which the therapeutic is administered. Such carriers can be sterile liquids, such as saline solutions in water, or oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The carrier, if desired, can also contain minor amounts of wetting or emulsifying agents, or pH buffering agents. These pharmaceutical compositions can take the form of solutions, suspensions, emulsion, tablets, pills, capsules, powders, sustained-release formulations and the like. The composition can be formulated as a suppository, with traditional binders and carriers such as triglycerides. Examples of suitable pharmaceutical carriers are described in *Remington's Pharmaceutical Sciences* by E. W. Martin. Examples of suitable pharmaceutical carriers are a variety of cationic polyamines and lipids, including, but not limited to N-(1(2,3-dioleyloxy)propyl)-N,N,N-trimethylammonium chloride (DOTMA) and diolesylphosphotidylethanolamine (DOPE). Liposomes are suitable carriers for gene therapy uses of the invention. Such pharmaceutical compositions should contain a therapeutically effective amount of the compound, together with a suitable amount of carrier so as to provide the form for proper administration to the subject. The formulation should suit the mode of administration.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

As used herein, the phrase "pharmaceutically acceptable salts" refers to salts prepared from pharmaceutically acceptable, essentially nontoxic, acids and bases, including inorganic and organic acids and bases. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

As used herein, an "immediate release" formulation of IGF-1, an "immediate release" formulation of GH, an "immediate release" co-formulation of IGF-1 and GH, or any mixture of an "immediate release" formulation of IGF-1 and an "immediate release" formulation of GH, refers to a drug composition or mixture of drug, compositions in which there is no carrier that regulates the bioavailability of the drug's active ingredient(s) to tissues at the site of drug administration in the patient's body. It will be understood that any component of the formulation that limits or impairs access of the drug's active ingredient(s) to tissues at the site of drug administration in the patient's body is a carrier that regulates the bioavailability of the active ingredient(s) so affected for purposes of the foregoing definition. By this definition, a formulation comprising an IGF-1/IGFBP-3 non-covalently associated complex fails to qualify as an "immediate release" formulation of IGF-1. Since it prevents the IGF-1 in the complex from binding to IGF-1 receptors in tissues and/or competes with IGF-1 receptors in tissues for binding to such IGF-1, the IGFBP-3 component of the IGF-1/IGFBP-3 non-covalently associated complex limits or impairs the access of such IGF-1 to tissues, and so qualifies as a carrier that regulates the bioavailability of such IGF-1 to tissues at the site of drug administration in the patient's body. In addition, this definition precludes any formulation that provides sustained-release or time-release of the drug's active ingredient(s) from a pool or reservoir in a macromolecular matrix carrier. For example, a formulation comprising IGF-1, GH, or any mixture of IGF-1 and GH, encapsulated in a bioerodible microsphere carrier fails to qualify as an "immediate release" formulation of IGF-1, GH or mixture thereof.

As used herein, the phrase "mean or maximum stimulated blood level of GH" means above a GH level in blood of about 3 or 5 ng/ml in adults and above about 3, 5 or 10 ng/ml in children as measured by a radioimmunoassay following a GH stimulation test wherein a compound or compounds are administered that causes the release of GH.

"In combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an," and "the" include plural referents unless the context clearly dictates otherwise. Thus, for example, reference to "an individual" includes one or more individuals, and reference to "the method" includes reference to equivalent steps and methods known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. Citation or discussion of a reference herein shall not be construed as an admission that such is prior art to the present invention.

The invention will now be described in more detail.

Mean body weight change (g/week) for each dose level cohort is shown at regular intervals over the course of treatment. The open circles, solid circles, open squares, solid squares, and open triangles represent treatment groups that received daily subcutaneous injections of placebo, 0.25 mg IGF-1/kg body weight, 1 mg IGF-1/kg body weight, 4 mg IGF-1/kg body weight, and 10 mg IGF-1/kg body weight, respectively.

Figure 17:
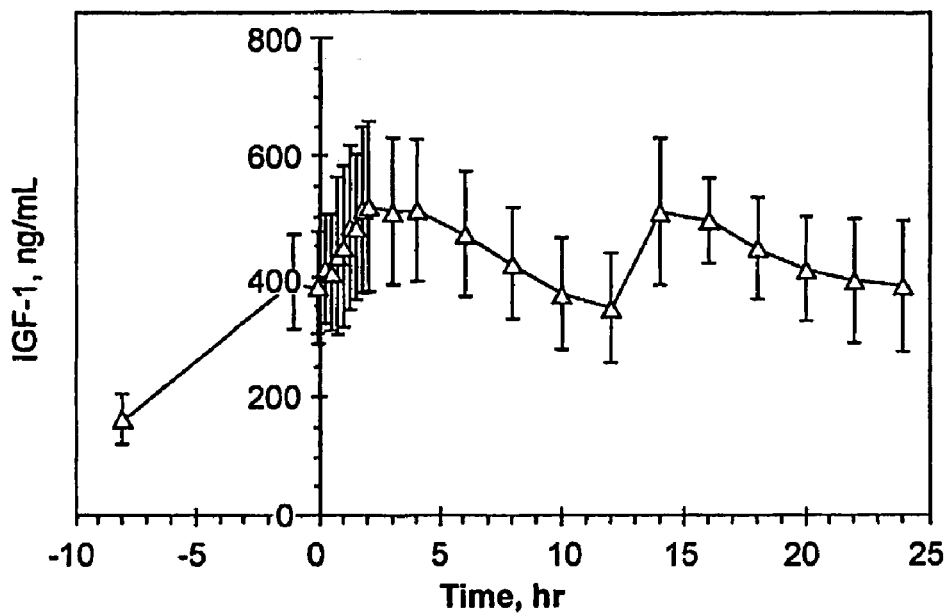

FIG. 17 is a graph depicting a plot of IGF-1 blood concentration over 24 hours at steady state in patients receiving 40 μg IGF-1/kg body weight twice daily (BID).

Figure 18:
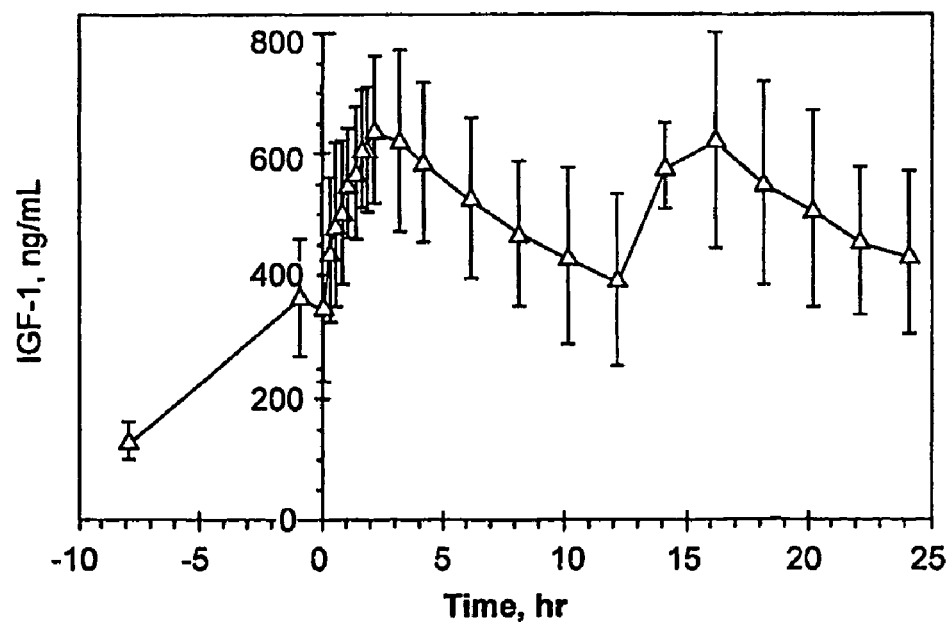

FIG. 18 is a graph depicting a plot of IGF-1 blood concentration over 24 hours at steady state in patients receiving 80 μg IGF-1/kg body weight twice daily (BID).

Figure 19:
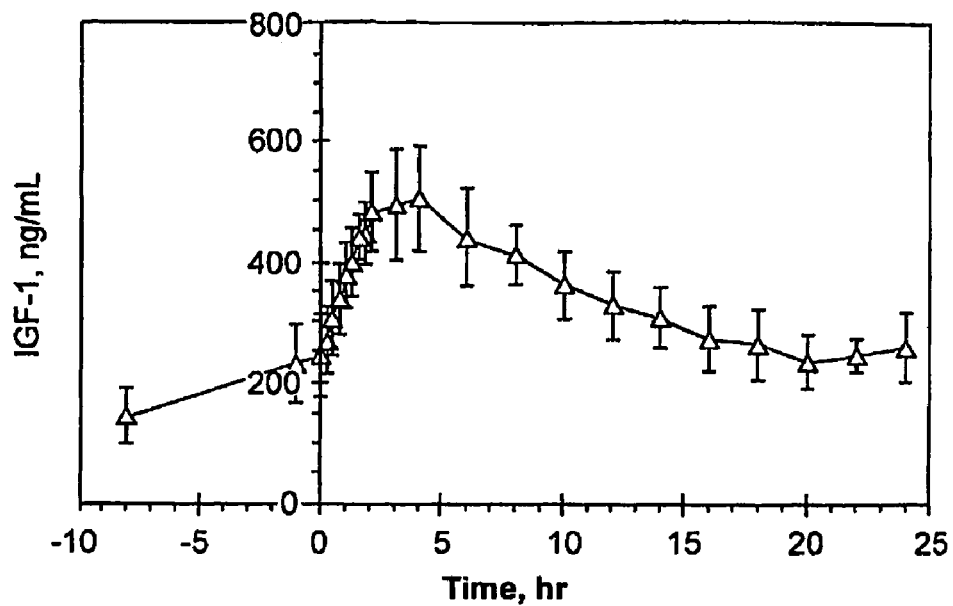

FIG. 19 is a graph depicting a plot of IGF-1 blood concentration over 24 hours at steady state in patients receiving 80 μg IGF-1/kg body weight once daily (QD).

Figure 20:
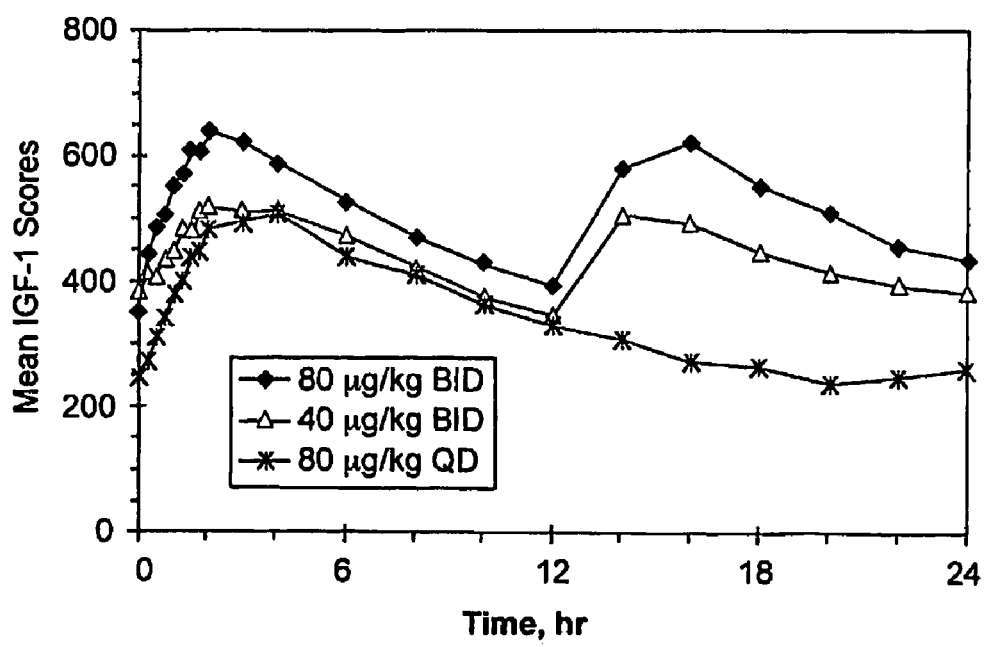

FIG. 20 is a graph depicting a plot of average IGF-1 blood concentration over 24 hours at steady state for each of the 40 μg IGF-1/kg body weight BID, 80 μg IGF-1/kg body weight BID, and 80 μg IGF-1/kg body weight QD dosage cohorts.

Figure 21:
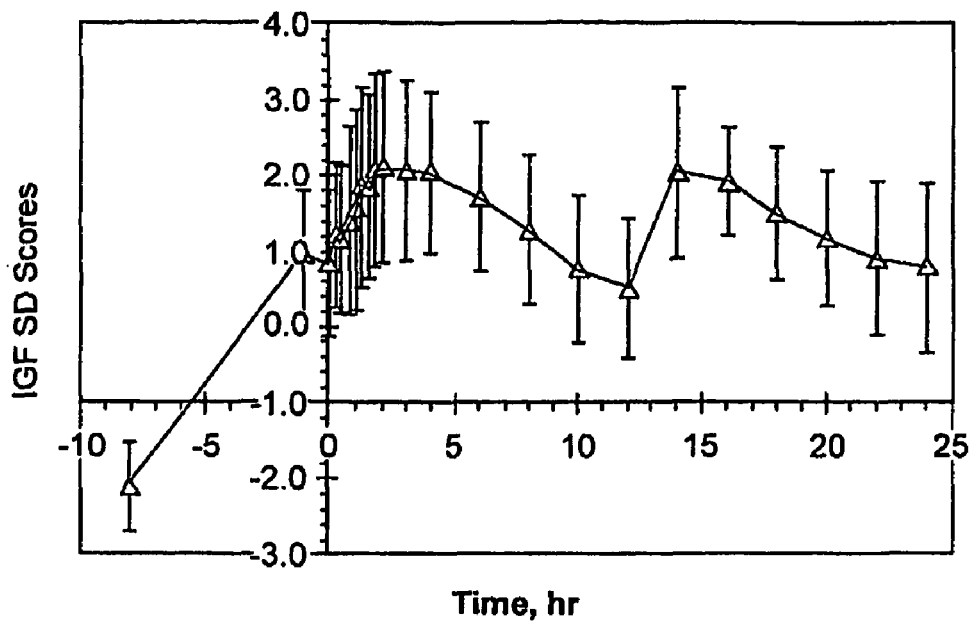

FIG. 21 is a graph depicting a plot of average IGF-1 blood concentration as standard deviation scores (SDS) over 24 hours at steady state for patients receiving 40 μg IGF-1/kg body weight BID.

Figure 22:
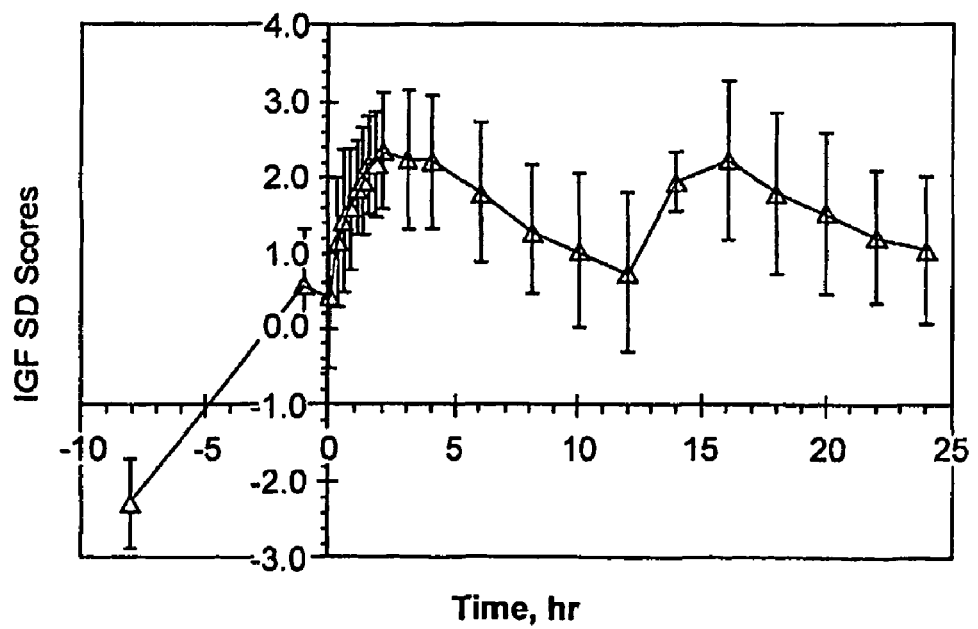

FIG. 22 is a graph depicting a plot of average IGF-1 blood concentration SDS over 24 hours at steady state for patients receiving 80 μg IGF-1/kg body weight BID.

Figure 23:
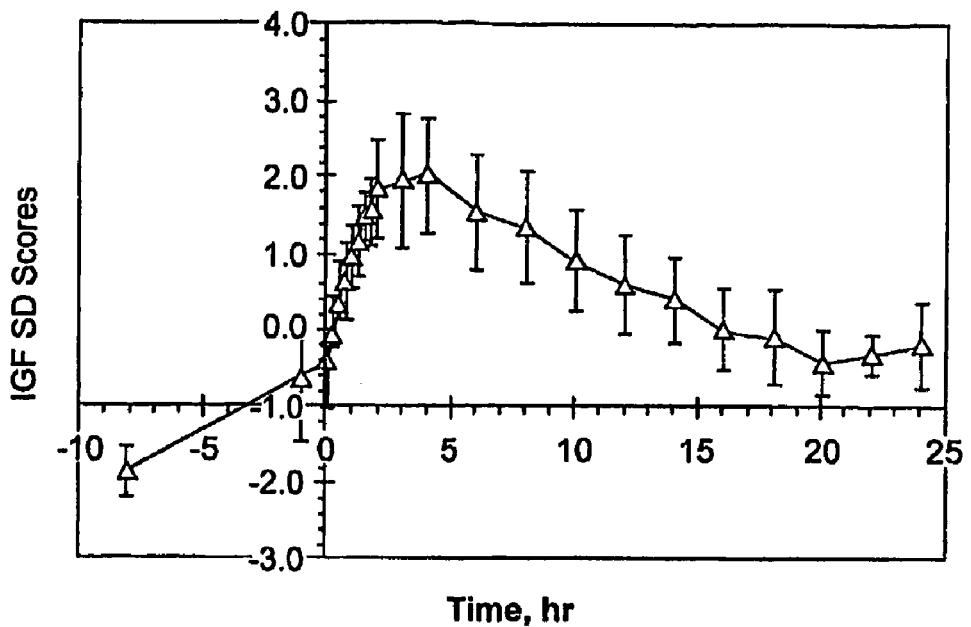

FIG. 23 is a graph depicting a plot of average IGF-1 blood concentration SDS over 24 hours at steady state for patients receiving 80 μg IGF-1/kg body weight QD.

Figure 24:
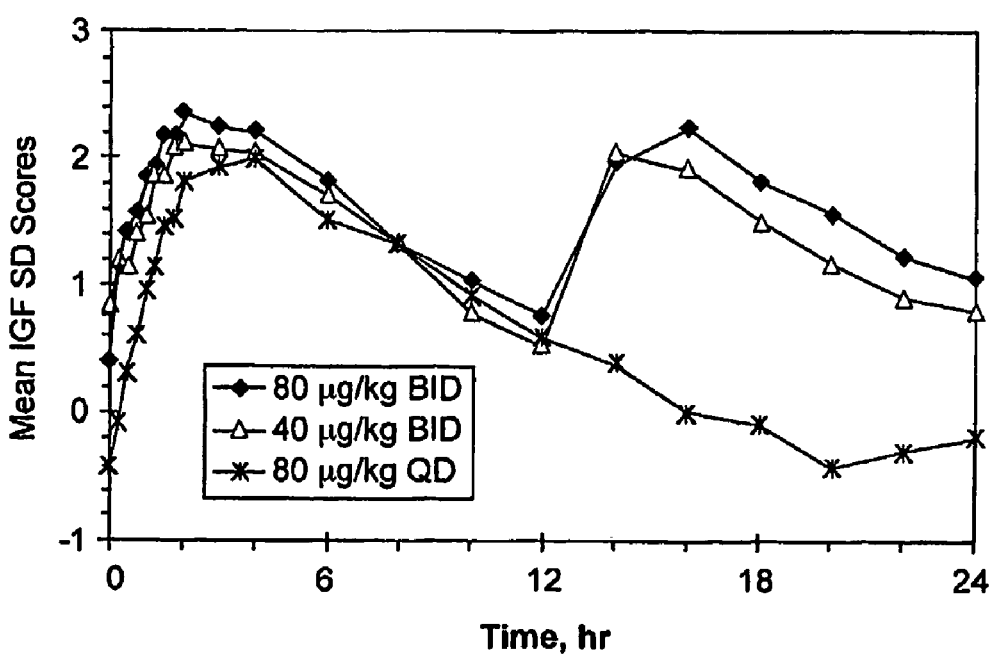

FIG. 24 is a graph depicting a plot of average IGF-1 blood concentration SDS over 24 hours at steady state for each of the 40 μg IGF-1/kg body weight BID, 80 μg IGF-1/kg body weight BID, and 80 μg IGF-1/kg body weight QD dosage cohorts.

Figure 25:
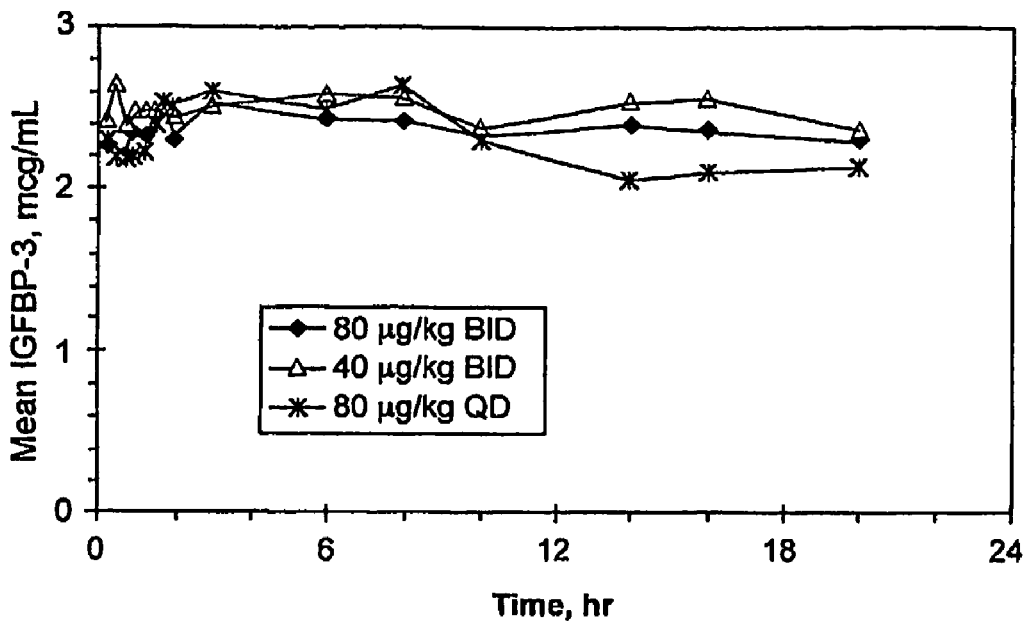

FIG. 25 is a graph depicting a plot of average IGFBP-3 blood concentration in micrograms per ml over 20 hours at steady state for each of the 40 μg IGF-1/kg body weight BID, 80 μg IGF-1/kg body weight BID, and 80 μg IGF-1/kg body weight QD dosage cohorts.

Figure 26:
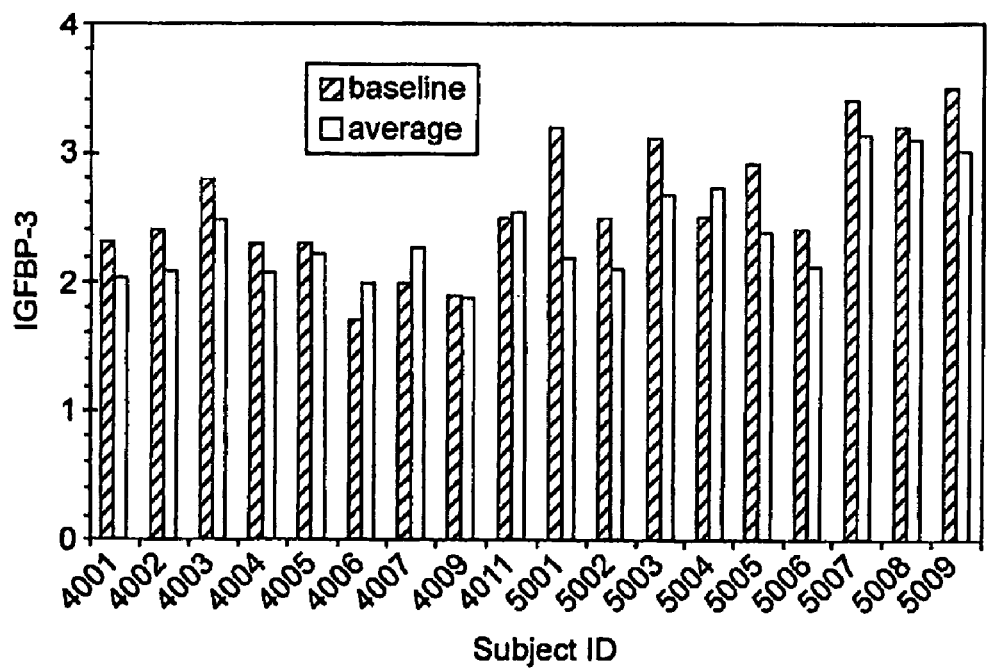

FIG. 26 is a bar chart depicting for each individual patient a comparison of the patient's IGFBP-3 blood concentration SD score at baseline against the patient's average IGFBP-3 blood concentration SD score over 24 hours at steady state.

Figure 27:
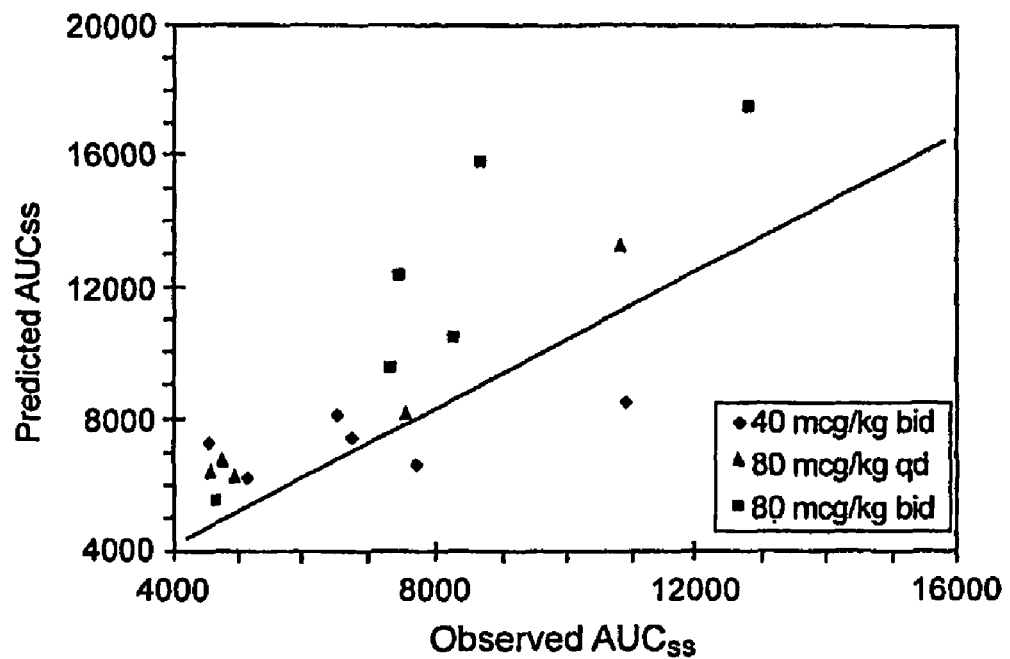

FIG. 27 is a graph depicting for each individual patient a comparison of the patient's predicted and observed $AUC_{ss}$ (hr*ng/mL) of total IGF-1 concentration in blood over 24 hours for each of the 40 μg IGF-1/kg body weight BID, 80 μg IGF-1/kg body weight BID, and 80 μg IGF-1/kg body weight QD dosage cohorts, in which the predicted score is calculated as a function of IGF-1 dosage and IGFBP-3 blood concentration at screening.

Figure 28:
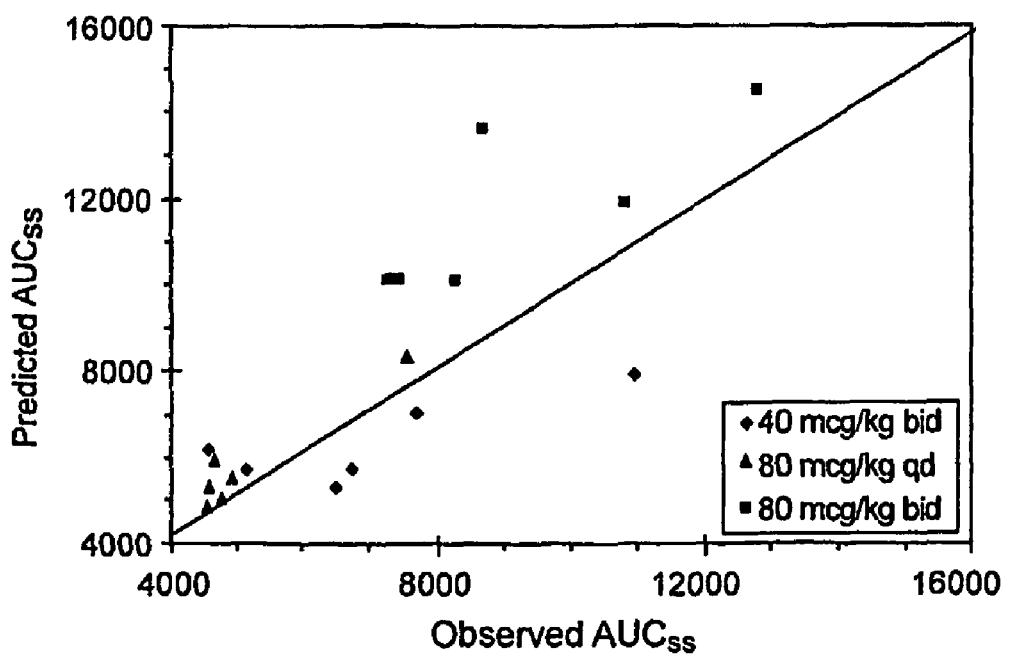

FIG. 28 is a graph depicting for each individual patient a comparison of the patient's predicted and observed $AUC_{ss}$ (hr*ng/mL) of total IGF-1 concentration in blood over 24 hours for each of the 40 μg IGF-1/kg body weight BID, 80 μg IGF-1/kg body weight BID, and 80 μg IGF-1/kg body weight QD dosage cohorts, in which the predicted score is calculated as a function of IGF-1 dosage and IGFBP-3 blood concentration on Day 21 just prior to dosing.

Figure 29:
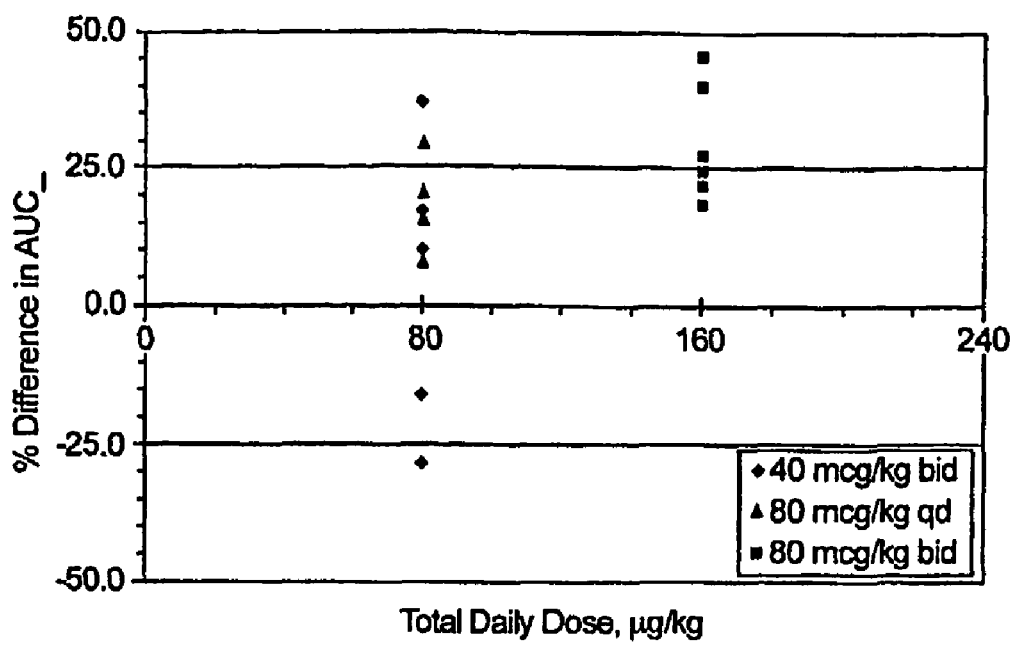

FIG. 29 is a plot depicting for each individual patient the percent difference between the patient's predicted and observed $AUC_{ss}$ (hr*ng/mL) of total IGF-1 concentration in blood over 24 hours for each of the 40 μg IGF-1/kg body weight BID, 80 μg IGF-1/kg body weight BID, and 80 μg IGF-1/kg body weight QD dosage cohorts, in which the predicted score is calculated as a function of IGF-1 dosage and IGFBP-3 blood concentration at screening. The percent difference score is calculated by the equation: Percent difference=100%*(Observed $AUC_{ss}$–Predicted AUCss)/Predicted AUCss.

Figure 30:
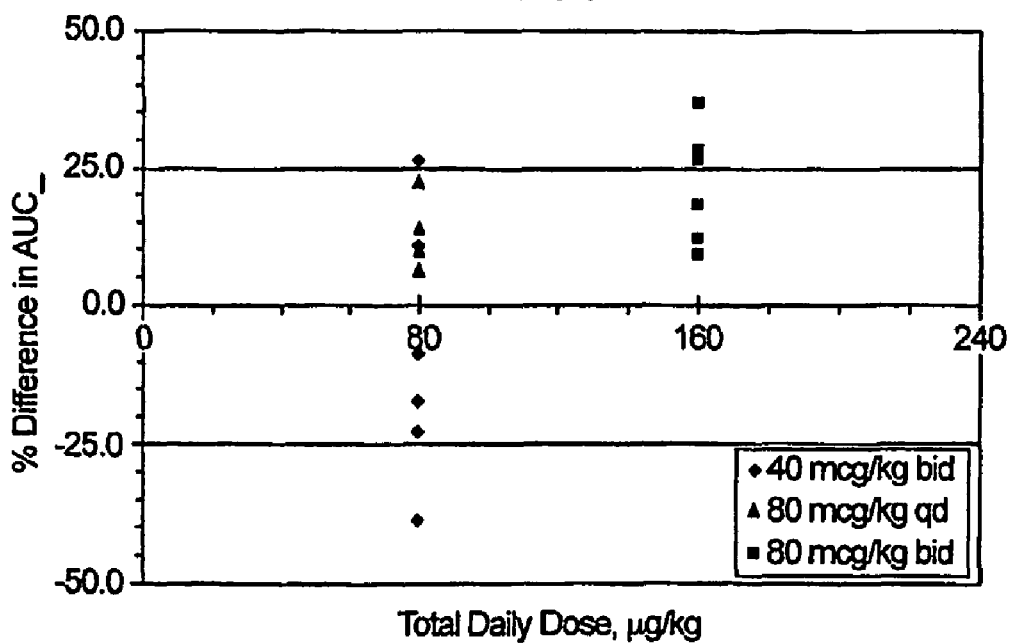

FIG. 30 is a plot depicting for each individual patient the percent difference between the patient's predicted and observed $AUC_{ss}$ (hr*ng/mL) of total IGF-1 concentration in blood over 24 hours for each of the 40 μg IGF-1/kg body weight BID, 80 μg IGF-1/kg body weight BID, and 80 μg IGF-1/kg body weight QD dosage cohorts, in which the predicted score is calculated as a function of IGF-1 dosage and IGFBP-3 blood concentration on Day 21 just prior to dosing. The percent difference score is calculated by the equation: Percent difference=100%*(Observed $AUC_{ss}$–Predicted AUCss)/Predicted AUCss.

DETAILED DESCRIPTION OF THE INVENTION

It has been common practice in children to administer IGF-1 by twice daily injection to induce a statural growth response. These data have been produced in rare children with no growth hormone activity or signaling, usually due to a lack of growth hormone receptor function.

The present invention is based on the surprising finding that IGF-1 therapy is likely to be more effective in the treatment of growth disorders in children with some endogenous GH signaling (i.e., patients suffering from a growth disorder characterized by partial endogenous growth hormone activity or signaling), particularly in children further characterized by partial GH deficiency, moderate primary IGFD, or non-GHD non-IGFD (ISS) syndrome, when administered by once daily injection to induce a growth response.

The present invention is also based on the unexpected result that IGF-1 and growth hormone (GH) combination therapy is likely to be more effective in the treatment of children suffering from a growth disorder characterized by partial endogenous GH signaling, particularly in children further characterized by partial GH deficiency, moderate primary IGFD, or non-GHD non-IGFD (ISS) syndrome, when GH and IGF-1 are each administered once daily, and when the GH administration is substantially contemporaneous with the IGF-1 administration each day.

Until recently GH was used only in children with GH deficiency—in these children it was not necessary to understand how endogenous GH is produced or how to account for endogenous GH secretion in dosing with GH. In addition, IGF-1 was used only in children with IGF-1 deficiency caused by complete GH resistance—in these children it was also not necessary to take account of GH secretion as the GH produced had no effect due to a lack of GH receptor function. But when GH and/or IGF-1 are used in children with some endogenous GH, and some endogenous GH signaling, the configuration of dosing regimens becomes much more important.

In subjects suffering from short stature characterized by a complete lack of GH signaling administering GH does not stimulate statural growth. It has been found that twice daily administration of rhIGF-1 is the treatment regimen of choice to stimulate statural growth in these patients. It might therefore be expected that in other subjects suffering from short stature that twice daily rhIGF-1 would be the dose regimen of choice. However, in the present study of the effects of twice daily rhIGF-1 administration vs. once daily rhIGF-1 administration in short stature patients who have some GH signaling, once daily rhIGF-1 administration was unexpectedly discovered to be the superior mode of administration.

In this study, several doses (15, 30, 60, 120 micrograms/kg) of rhIGF-1 were administered once daily. A key finding of this study is that GH secretion is inhibited for several hours after IGF-1 delivery, but that GH secretion then returns and is increased (or "rebounds"). Since IGFBP-3 is a protein that is regulated by GH, the blood level of IGFBP-3 can be used as a marker of GH activity. In this study the blood level of IGFBP-3 is increased after 24 and 36 hours. Therefore with once daily dosing of rhIGF-1 the net effect on "GH activity" is increased.

In another of the present studies, rhIGF-1 was administered by twice daily injection at two doses (40 and 80 micrograms/kg) or by once daily injection at 80 micrograms/kg. In this study, the patients exhibited blood levels of IGFBP-3 that declined in response to twice daily rhIGF-1 therapy. As discovered in the present invention, this is due to twice daily IGF-1 effectively reducing GH, suppressing IGFBP-3, and reducing the amount of endogenous GH activity and GH signaling.

It is known that exposure to exogenous GH downregulates the secretion of endogenous GH in treated patients. In view of the present discovery that once daily IGF-1 administration increases the net effect on "GH activity," as described above, it was further discovered that in the context of IGF-1 and GH combination therapy for patients having partial endogenous GH signaling, coincident or substantially contemporaneous administration of IGF-1 and GH once daily will increase the net effect on "GH activity" in the patient.

Accordingly, one patient group who will benefit from the dosing regimens of the invention are patients who have
1) Endogenous GH activity, i.e. are not GH deficient—if a subject is GH deficient there is no opportunity to affect their GH secretion; and
2) Endogenous GH signaling, i.e. are not GH resistant—if a subject is GH resistant an effect on GH secretion will have no obvious effect as the patient is not able to respond to GH.

Therefore, the therapeutic approach of the invention is well suited to patients who have non-GHD and non-IGFD short stature, better known as subjects who are ISS, in that they
1) have the ability to secrete GH; and
2) are able to respond to GH.

Methods of Treatment
1. Growth Disorders in Pediatric Patients

The present invention provides methods and compositions for improving growth in patients suffering from growth disorders characterized by partial endogenous growth hormone activity or signaling. In general, the growth disorder patient exhibits (1) a height SDS that is at least −2 (i.e., at least 2 SD below the normal mean for the corresponding age and gender of the patient) and (2) an endocrine system that exhibits endogenous GH induction of IGF-1 and IGFBP-3, and (3) evidence of endogenous GH secretion.

In one embodiment, the invention provides a method of treating a growth disorder comprising administering to a patient suffering from a growth disorder characterized by partial endogenous growth hormone activity or signaling an amount of insulin-like growth factor-1 (IGF-1) effective to promote growth in the patient, and wherein the patient receives IGF-1 in a single administration per day. In some embodiments, the patient receives the single administration of IGF-1 at around the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) effective to promote growth in the patient, wherein the patient has idiopathic short stature (ISS), and wherein the patient receives IGF-1 in a single administration per day. In some embodiments, the patient receives the single administration of IGF-1 at around the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) effective to promote growth in the patient, wherein the patient has moderate primary insulin-like growth factor deficiency (IGFD) but not severe primary IGFD, and wherein the patient receives IGF-1 in a single administration per day. In some embodiments, the patient receives the single administration of IGF-1 at around the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) effective to promote growth in the patient, wherein the patient has a blood level of IGF-1 that at the time of treatment or prior to initial treatment with IGF-1 is below, usually at least about 1 standard deviation below, but not more than about 2 standard deviations below, normal mean levels for the corresponding age and gender of the patient, and wherein the patient receives IGF-1 in a single administration per day. In some embodiments, the patient receives the single administration of IGF-1 at around the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) effective to promote growth in the patient, wherein the patient has a normal blood level of growth hormone (GH) at the time of treatment or prior to initial treatment with IGF-1, and wherein the patient receives IGF-1 in a single administration per day. In some embodiments, the patient receives the single administration of IGF-1 at around the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) effective to promote growth in the patient, wherein the patient has a normal blood level of GH at the time of treatment or prior to initial treatment with IGF-1 and has a blood level of IGF-1 that at the time of treatment or prior to initial treatment with IGF-1 is below, usually at least about 1 standard deviation below, but not more than about 2 standard deviations below, normal mean levels for the corresponding age and gender of the patient, and wherein the patient receives IGF-1 in a single administration per day. In some embodiments, the patient receives the single administration of IGF-1 at or about the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) effective to promote growth in the patient, wherein the patient has intact growth hormone (GH) secretion, and wherein the patient receives IGF-1 in a single administration per day. In some embodiments, the patient receives the single administration of IGF-1 at or about the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) effective to promote growth in the patient, wherein the patient has intact IGF-1 induction in response to GH, and wherein the patient receives IGF-1 in a single administration per day. In some embodiments, the patient receives the single administration of IGF-1 at around the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) effective to promote growth in the patient, wherein the patient has intact growth hormone (GH) secretion and intact IGF-1 induction in response to GH, and wherein the patient receives IGF-1 in a single administration per day. In some embodiments, the patient receives the single administration of IGF-1 at or about the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) effective to promote growth in the patient, wherein the patient has levels of high affinity growth hormone binding protein (GHBP) in blood equal to or greater than normal mean levels for the corresponding age and gender of the patient, and wherein the patient receives IGF-1 in a single administration per day. In some embodiments, the patient receives the single administration of IGF-1 at or about the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) effective to promote growth in the patient, wherein the patient has idiopathic short stature (ISS), and has levels of high affinity growth hormone binding protein (GHBP) in blood equal to or greater than normal mean levels for the corresponding age and gender of the patient, and wherein the patient receives IGF-1 in a single administration per day. In some embodiments, the patient receives the single administration of IGF-1 at or about the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) effective to promote growth in the patient, wherein the patient has moderate primary insulin-like growth factor deficiency (IGFD) but not severe primary IGFD, and has levels of high affinity growth hormone binding protein (GHBP) in blood equal to or greater than normal mean levels for the corresponding age and gender of the patient, and wherein the patient receives IGF-1 in a single administration per day. In some embodiments, the patient receives the single administration of IGF-1 at or about the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) effective to promote growth in the patient, wherein the patient has a blood level of IGF-1 that at the time of treatment or prior to initial treatment with IGF-1 is below, usually at least about 1 standard deviation below, but not more than about 2 standard deviations below, normal mean levels for the corresponding age and gender of the patient, and has levels of high affinity growth hormone binding protein (GHBP) in blood equal to or greater than normal mean levels for the corresponding age and gender of the patient, and wherein the patient receives IGF-1 in a single administration per day. In some embodiments, the patient receives the single administration of IGF-1 at or about the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) effective to promote growth in the patient, wherein the patient has a normal blood level of growth hormone (GH) at the time of treatment or prior to initial treatment with IGF-1, and has levels of high affinity growth hormone binding protein (GHBP) in blood equal to or greater than normal mean levels for the corresponding age and gender of the patient, and wherein the patient receives IGF-1 in a single administration per day. In some embodiments, the patient receives the single administration of IGF-1 at or about the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) effective to promote growth in the patient, wherein the patient has a normal blood level of growth hormone (GH) at the time of treatment or prior to initial treatment with IGF-1, has a blood level of IGF-1 that at the time of treatment or prior to initial treatment with IGF-1 is below, usually at least about 1 standard deviation below, but not more than about 2 standard deviations below, normal mean levels for the corresponding age and gender of the patient, and has levels of high affinity growth hormone binding protein (GHBP) in blood equal to or greater than normal mean levels for the corresponding age and gender of the patient, and wherein the patient receives IGF-1 in a single administration per day. In some embodiments, the patient receives the single administration of IGF-1 at or about the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) effective to promote growth in the patient, wherein the patient has intact GH secretion, and levels of high affinity growth hormone binding protein (GHBP) in blood equal to or greater than normal mean levels for the corresponding age and gender of the patient, and wherein the patient receives IGF-1 in a single administration per day. In some embodiments, the patient receives the single administration of IGF-1 at or about the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) effective to promote growth in the patient, wherein the patient has intact IGF-1 induction in response to GH, and levels of high affinity growth hormone binding protein (GHBP) in blood equal to or greater than normal mean levels for the corresponding age and gender of the patient, and wherein the patient receives IGF-1 in a single administration per day. In some embodiments, the patient receives the single administration of IGF-1 at or about the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) effective to promote growth in the patient, wherein the patient has intact GH secretion, intact IGF-1 induction in response to GH, and levels of high affinity growth hormone binding protein (GHBP) in blood equal to or greater than normal mean levels for the corresponding age and gender of the patient, and wherein the patient receives IGF-1 in a single administration per day. In some embodiments, the patient receives the single administration of IGF-1 at or about the time of breakfast or within about two hours of awakening from sleep each day.

In another embodiment, the invention provides any of the above-described methods for IGF-1 therapy to promote growth in a patient suffering from a growth disorder characterized by partial endogenous growth hormone activity or signaling, wherein the patient is further characterized by not having partial growth hormone insensitivity syndrome (GHIS).

In another embodiment, the invention provides any of the above-described methods for IGF-1 therapy to promote growth in a patient suffering from a growth disorder characterized by partial endogenous growth hormone activity or signaling, wherein the patient receives the single daily administration of IGF-1 by subcutaneous bolus injection.

In another embodiment, the invention provides a method of treating a growth disorder comprising administering to a patient suffering from a growth disorder characterized by partial endogenous growth hormone activity or signaling an amount of insulin-like growth factor-1 (IGF-1) and an amount of growth hormone (GH) that are effective when given as a combination therapy to promote growth in the patient, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at around the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) and an amount of growth hormone (GH) that are effective when given as a combination therapy to promote growth in the patient, wherein the patient has at least normal levels of high affinity growth hormone binding protein (GHBP) in blood, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at around the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) and an amount of growth hormone (GH) that are effective when given as a combination therapy to promote growth in the patient, wherein the patient has idiopathic short stature (ISS), wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at around the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) and an amount of growth hormone (GH) that are effective when given as a combination therapy to promote growth in the patient, wherein the patient has idiopathic short stature (ISS), and has at least normal levels of high affinity growth hormone binding protein (GHBP) in blood, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at around the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) and an amount of growth hormone (GH) that are effective when given as a combination therapy to promote growth in the patient, wherein the patient has moderate primary insulin-like growth factor deficiency (IGFD) but not severe primary IGFD, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at around the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) and an amount of growth hormone (GH) that are effective when given as a combination therapy to promote growth in the patient, wherein the patient has moderate primary insulin-like growth factor deficiency (IGFD) but not severe primary IGFD, and has at least normal levels of high affinity growth hormone binding protein (GHBP) in blood, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at around the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) and an amount of growth hormone (GH) that are effective when given as a combination therapy to promote growth in the patient, wherein the patient has a blood level of IGF-1 that at the time of treatment or prior to initial treatment with IGF-1 and GH is below, usually at least about 1 standard deviation below, but not more than about 2 standard deviations below, normal mean levels for a corresponding age and gender, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at around the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) and an amount of growth hormone (GH) that are effective when given as a combination therapy to promote growth in the patient, wherein the patient has a blood level of IGF-1 that at the time of treatment or prior to initial treatment with IGF-1 and GH is below, usually at least about 1 standard deviation below, but not more than about 2 standard deviations below, normal mean levels for a corresponding age and gender, and has at least normal levels of high affinity growth hormone binding protein (GHBP) in blood, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at around the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) and an amount of growth hormone (GH) that are effective when given as a combination therapy to promote growth in the patient, wherein the patient has a normal blood level of GH at the time of treatment or prior to initial treatment with IGF-1 and GH, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at around the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) and an amount of growth hormone (GH) that are effective when given as a combination therapy to promote growth in the patient, wherein the patient has normal blood levels of GH at the time of treatment or prior to initial treatment with IGF-1 and GH, and has at least normal levels of high affinity growth hormone binding protein (GHBP) in blood, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at around the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) and an amount of growth hormone (GH) that are effective when given as a combination therapy to promote growth in the patient, wherein the patient has a normal blood level of GH at the time of treatment or prior to initial treatment with IGF-1 and GH, and has a blood level of IGF-1 that at the time of treatment or prior to initial treatment with IGF-1 and GH is below, usually at least about 1 standard deviation below, but not more than about 2 standard deviations below, normal mean levels for a corresponding age and gender, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at around the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) and an amount of growth hormone (GH) that are effective when given as a combination therapy to promote growth in the patient, wherein the patient has a normal blood level of GH at the time of treatment or prior to initial treatment with IGF-1 and GH, has a blood level of IGF-1 that at the time of treatment or prior to initial treatment with IGF-1 and GH is below, usually at least about 1 standard deviation below, but not more than about 2 standard deviations below, normal mean levels for a corresponding age and gender, and has at least normal levels of high affinity growth hormone binding protein (GHBP) in blood, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at around the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) and an amount of growth hormone (GH) that are effective when given as a combination therapy to promote growth in the patient, wherein the patient has intact GH secretion, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at around the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) and an amount of growth hormone (GH) that are effective when given as a combination therapy to promote growth in the patient, wherein the patient has intact GH secretion, and at least normal levels of high affinity growth hormone binding protein (GHBP) in blood, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at around the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) and an amount of growth hormone (GH) that are effective when given as a combination therapy to promote growth in the patient, wherein the patient has intact IGF-1 induction in response to GH, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at around the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) and an amount of growth hormone (GH) that are effective when given as a combination therapy to promote growth in the patient, wherein the patient has intact IGF-1 induction in response to GH, and at least normal levels of high affinity growth hormone binding protein (GHBP) in blood, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at around the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) and an amount of growth hormone (GH) that are effective when given as a combination therapy to promote growth in the patient, wherein the patient has intact GH secretion and IGF-1 induction in response to GH, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at around the time of breakfast or within about two hours of awakening from sleep each day.

In another embodiment, the invention provides a method of treating a growth disorder comprising administering to a patient suffering from a growth disorder characterized by partial endogenous growth hormone activity or signaling an amount of insulin-like growth factor-1 (IGF-1) and an amount of growth hormone (GH) that are effective when given as a combination therapy to promote growth in the patient, wherein the patient has intact GH secretion and intact IGF-1 induction in response to GH, and at least normal levels of high affinity growth hormone binding protein (GHBP) in blood, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at around the time of breakfast or within about two hours of awakening from sleep each day.

In another embodiment, the invention provides any of the above-described methods for GH and IGF-1 combination therapy to promote growth in a patient suffering from a growth disorder characterized by partial endogenous growth hormone activity or signaling, wherein the patient does not have partial growth hormone insensitivity syndrome (GHIS).

In some embodiments, the patient receives the single administration of IGF-1 and the single administration of GH by bolus injection each day. In some of these embodiments, the IGF-1 and GH are in the form of a co-formulated or co-mixed drug that is administered to the patient by a single subcutaneous injection each day. In other embodiments, the IGF-1 and GH are in the form of separately formulated drugs that are administered to the patient by one injection or by separate injections.

In addition, the invention provides a modification of any of the above-described methods of treating growth disorders in which whatever IGF-1 administration is called for in the subject method is administered to the patient in a single administration of an immediate release formulation of IGF-1, and whatever IGF-1 and GH administration combination is called for in the subject method is (a) administered to the patient in a single administration of an immediate release co-formulation of IGF-1 and GH, (b) administered to the patient in a single administration of an immediate release formulation of IGF-1 and in a single administration of a separate immediate release formulation of GH, or (c) administered to the patient in a single administration of an immediate release formulation of IGF-1 and a separate immediate release formulation of GH that are admixed prior to such administration.

2. Endocrine Disorders in Adult Patients

The present invention provides methods and compositions for improving metabolism in adult patients suffering from endocrine disorders characterized by partial endogenous growth hormone activity or signaling. Typically, adult patients well suited for the therapies of the invention include patients who as children suffered from growth disorders characterized by partial endogenous growth hormone activity or signaling. When partial endogenous growth hormone activity or signaling conditions that cause growth disorders in childhood persist into adulthood, the affected adult can suffer from a variety of metabolic disorders and/or sequelae of such metabolic disorders, including increased blood pressure, decreased cardiac performance, cardiac disease, renal disease, neurological disease, impaired exercise performance, decreased muscle mass, decreased bone density, obesity, and abnormalities of lipid and carbohydrate metabolism. The methods of the invention provide therapies for the replacement of normal endocrine function to improve the metabolic health of these patients.

In one embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) effective to improve a metabolic abnormality in the patient, and wherein the patient receives IGF-1 in a single administration per day. In some embodiments, the patient receives the single administration of IGF-1 at around the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) effective to improve a metabolic abnormality in the patient, wherein the patient has adult idiopathic short stature (ISS) syndrome, and wherein the patient receives IGF-1 in a single administration per day. In some embodiments, the patient receives the single administration of IGF-1 at around the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) effective to improve a metabolic abnormality in the patient, wherein the patient has moderate primary insulin-like growth factor deficiency (IGFD) but not severe primary IGFD, and wherein the patient receives IGF-1 in a single administration per day. In some embodiments, the patient receives the single administration of IGF-1 at around the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) effective to improve a metabolic abnormality in the patient, wherein the patient has a blood level of IGF-1 that at the time of treatment or prior to initial treatment with IGF-1 is below, usually at least about 1 standard deviation below, but not more than about 2 standard deviations below, normal mean levels for the corresponding age and gender of the patient, and wherein the patient receives IGF-1 in a single administration per day. In some embodiments, the patient receives the single administration of IGF-1 at around the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) effective to improve a metabolic abnormality in the patient, wherein the patient has a blood level of growth hormone (GH) that is normal at the time of treatment or prior to initial treatment with IGF-1, and wherein the patient receives IGF-1 in a single administration per day. In some embodiments, the patient receives the single administration of IGF-1 at around the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) effective to improve a metabolic abnormality in the patient, wherein the patient has a blood level of GH that is normal at the time of treatment or prior to initial treatment with IGF-1, and has a blood level of IGF-1 that at the time of treatment or prior to initial treatment with IGF-1 is below, usually at least about 1 standard deviation below, but not more than about 2 standard deviations below, normal mean levels for the corresponding age and gender of the patient, and wherein the patient receives IGF-1 in a single administration per day. In some embodiments, the patient receives the single administration of IGF-1 at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) effective to improve a metabolic abnormality in the patient, wherein the patient has intact growth hormone (GH) secretion, and wherein the patient receives IGF-1 in a single administration per day. In some embodiments, the patient receives the single administration of IGF-1 at or around the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) effective to improve a metabolic abnormality in the patient, wherein the patient has intact IGF-1 induction in response to GH, and wherein the patient receives IGF-1 in a single administration per day. In some embodiments, the patient receives the single administration of IGF-1 at or around the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) effective to improve a metabolic abnormality in the patient, wherein the patient has intact growth hormone (GH) secretion and intact IGF-1 induction in response to GH, and wherein the patient receives IGF-1 in a single administration per day. In some embodiments, the patient receives the single administration of IGF-1 at or around the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) effective to improve a metabolic abnormality in the patient, wherein the patient has levels of high affinity growth hormone binding protein (GHBP) in blood equal to or greater than normal mean levels for the corresponding age and gender of the patient, and wherein the patient receives IGF-1 in a single administration per day. In some embodiments, the patient receives the single administration of IGF-1 at or around the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) effective to improve a metabolic abnormality in the patient, wherein the patient has adult idiopathic short stature (ISS) syndrome, and has levels of high affinity growth hormone binding protein (GHBP) in blood equal to or greater than normal mean levels for the corresponding age and gender of the patient, and wherein the patient receives IGF-1 in a single administration per day. In some embodiments, the patient receives the single administration of IGF-1 at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) effective to improve a metabolic abnormality in the patient, wherein the patient has moderate primary insulin-like growth factor deficiency (IGFD) but not severe primary IGFD, and has levels of high affinity growth hormone binding protein (GHBP) in blood equal to or greater than normal mean levels for the corresponding age and gender of the patient, and wherein the patient receives IGF-1 in a single administration per day. In some embodiments, the patient receives the single administration of IGF-1 at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) effective to improve a metabolic abnormality in the patient, wherein the patient has a blood level of IGF-1 that at the time of treatment or prior to initial treatment with IGF-1 is below, usually at least about 1 standard deviation below, but not more than about 2 standard deviations below, normal mean levels for the corresponding age and gender of the patient, and has levels of high affinity growth hormone binding protein (GHBP) in blood equal to or greater than normal mean levels for the corresponding age and gender of the patient, and wherein the patient receives IGF-1 in a single administration per day. In some embodiments, the patient receives the single administration of IGF-1 at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) effective to improve a metabolic abnormality in the patient, wherein the patient has a normal blood level of growth hormone (GH) at the time of treatment or prior to initial treatment with IGF-1, and has levels of high affinity growth hormone binding protein (GHBP) in blood equal to or greater than normal mean levels for the corresponding age and gender of the patient, and wherein the patient receives IGF-1 in a single administration per day. In some embodiments, the patient receives the single administration of IGF-1 at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) effective to improve a metabolic abnormality in the patient, wherein the patient has a normal blood level of growth hormone (GH) at the time of treatment or prior to initial treatment with IGF-1, has a blood level of IGF-1 that at the time of treatment or prior to initial treatment with IGF-1 is below, usually at least about 1 standard deviation below, but not more than about 2 standard deviations below, normal mean levels for the corresponding age and gender of the patient, and has levels of high affinity growth hormone binding protein (GHBP) in blood equal to or greater than normal mean levels for the corresponding age and gender of the patient, and wherein the patient receives IGF-1 in a single administration per day. In some embodiments, the patient receives the single administration of IGF-1 at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) effective to improve a metabolic abnormality in the patient, wherein the patient has a normal blood level of GH, and levels of high affinity growth hormone binding protein (GHBP) in blood equal to or greater than normal mean levels for the corresponding age and gender of the patient, and wherein the patient receives IGF-1 in a single administration per day. In some embodiments, the patient receives the single administration of IGF-1 at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) effective to improve a metabolic abnormality in the patient, wherein the patient has intact IGF-1 induction by growth hormone, and levels of high affinity growth hormone binding protein (GHBP) in blood equal to or greater than normal mean levels for the corresponding age and gender of the patient, and wherein the patient receives IGF-1 in a single administration per day. In some embodiments, the patient receives the single administration of IGF-1 at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) effective to improve a metabolic abnormality in the patient, wherein the patient has intact GH secretion, intact IGF-1 induction in response to GH, and levels of high affinity growth hormone binding protein (GHBP) in blood equal to or greater than normal mean levels for the corresponding age and gender of the patient, and wherein the patient receives IGF-1 in a single administration per day. In some embodiments, the patient receives the single administration of IGF-1 at or about the time of breakfast or within about two hours of awakening from sleep each day.

In another embodiment, the invention provides any of the above-described methods for IGF-1 therapy to improve a metabolic abnormality in a patient suffering from a metabolic disorder characterized by partial endogenous growth hormone activity or signaling, wherein the patient is further characterized by having had a growth disorder characterized by partial endogenous growth hormone activity or signaling during childhood.

In another embodiment, the invention provides any of the above-described methods for IGF-1 therapy to improve a metabolic abnormality in an adult patient suffering from a metabolic disorder characterized by partial endogenous growth hormone activity or signaling, wherein the patient is further characterized by not having partial growth hormone insensitivity syndrome (GHIS).

In another embodiment, the invention provides any of the above-described methods for IGF-1 therapy to improve a metabolic abnormality in an adult patient suffering from a metabolic disorder characterized by partial endogenous growth hormone activity or signaling, wherein the patient receives the single daily administration of IGF-1 by subcutaneous bolus injection.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) and an amount of growth hormone (GH) that are effective in combination therapy to improve a metabolic abnormality in the patient, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) and an amount of growth hormone (GH) that are effective in combination therapy to improve a metabolic abnormality in the patient, wherein the patient has at least normal levels of high affinity growth hormone binding protein (GHBP) in blood, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) and an amount of growth hormone (GH) that are effective in combination therapy to improve a metabolic abnormality in the patient, wherein the patient has adult idiopathic short stature (ISS) syndrome, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) and an amount of growth hormone (GH) that are effective in combination therapy to improve a metabolic abnormality in the patient, wherein the patient has idiopathic short stature (ISS) syndrome, and has at least normal levels of high affinity growth hormone binding protein (GHBP) in blood, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) and an amount of growth hormone (GH) that are effective in combination therapy to improve a metabolic abnormality in the patient, wherein the patient has moderate primary insulin-like growth factor deficiency (IGFD) but not severe primary IGFD, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) and an amount of growth hormone (GH) that are effective in combination therapy to improve a metabolic abnormality in the patient, wherein the patient has moderate primary insulin-like growth factor deficiency (IGFD) but not severe primary IGFD, and has at least normal levels of high affinity growth hormone binding protein (GHBP) in blood, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) and an amount of growth hormone (GH) that are effective in combination therapy to improve a metabolic abnormality in the patient, wherein the patient has a blood level of IGF-1 that at the time of treatment or prior to initial treatment with IGF-1 and GH is below, usually at least about 1 standard deviation below, but not more than about 2 standard deviations below, normal mean levels for a corresponding age and gender, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) and an amount of growth hormone (GH) that are effective in combination therapy to improve a metabolic abnormality in the patient, wherein the patient has a blood level of IGF-1 that at the time of treatment or prior to initial treatment with IGF-1 and GH is below, usually at least about 1 standard deviation below, but not more than about 2 standard deviations below, normal mean levels for a corresponding age and gender, and has at least normal levels of high affinity growth hormone binding protein (GHBP) in blood, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) and an amount of growth hormone (GH) that are effective in combination therapy to improve a metabolic abnormality in the patient, wherein the patient has a normal blood level of GH, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) and an amount of growth hormone (GH) that are effective in combination therapy to improve a metabolic abnormality in the patient, wherein the patient has a normal blood level of GH, and has at least normal levels of high affinity growth hormone binding protein (GHBP) in blood, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) and an amount of growth hormone (GH) that are effective in combination therapy to improve a metabolic abnormality in the patient, wherein the patient has a normal blood level of GH, and has a blood level of IGF-1 that at the time of treatment or prior to initial treatment with IGF-1 and GH is below, usually at least about 1 standard deviation below, but not more than about 2 standard deviations below, normal mean levels for a corresponding age and gender, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) and an amount of growth hormone (GH) that are effective in combination therapy to improve a metabolic abnormality in the patient, wherein the patient has a normal blood level of GH, has a blood level of IGF-1 that at the time of treatment or prior to initial treatment with IGF-1 and GH is below, usually at least about 1 standard deviation below, but not more than about 2 standard deviations below, normal mean levels for a corresponding age and gender, and has at least normal levels of high affinity growth hormone binding protein (GHBP) in blood, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) and an amount of growth hormone (GH) that are effective in combination therapy to improve a metabolic abnormality in the patient, wherein the patient has intact GH secretion, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at or about the time of breakfast or within about two hours of awakening from sleep each day.

In another embodiment, the invention provides a method of treating an endocrine growth disorder comprising administering to an adult patient suffering from a metabolic disorder characterized by partial endogenous growth hormone activity or signaling an amount of insulin-like growth factor-1 (IGF-1) and an amount of growth hormone (GH) that are effective in combination therapy to improve a metabolic abnormality in the patient, wherein the patient has intact GH secretion, and has at least normal levels of high affinity growth hormone binding protein (GHBP) in blood, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) and an amount of growth hormone (GH) that are effective in combination therapy to improve a metabolic abnormality in the patient, wherein the patient has intact IGF-1 induction in response to GH, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) and an amount of growth hormone (GH) that are effective in combination therapy to improve a metabolic abnormality in the patient, wherein the patient has intact IGF-1 induction in response to GH, and has at least normal levels of high affinity growth hormone binding protein (GHBP) in blood, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) and an amount of growth hormone (GH) that are effective in combination therapy to improve a metabolic abnormality in the patient, wherein the patient has intact GH secretion and IGF-1 induction in response to GH, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at or about the time of breakfast or within about two hours of awakening from sleep each day.

In another embodiment, the invention provides a method of treating an endocrine disorder comprising administering to an adult patient suffering from a metabolic disorder characterized by partial endogenous growth hormone activity or signaling an amount of insulin-like growth factor-1 (IGF-1) and an amount of growth hormone (GH) that are effective in combination therapy to improve a metabolic abnormality in the patient, wherein the patient has intact GH secretion and intact IGF-1 induction in response to GH, and has at least normal levels of high affinity growth hormone binding protein (GHBP) in blood, wherein the patient receives IGF-1 in a single administration per day and receives GH in a single administration per day, and wherein the patient receives the administrations of IGF-1 and GH contemporaneously or substantially contemporaneously. In some embodiments, the patient receives the single daily administration of IGF-1 and the single daily administration of GH at or about the time of breakfast or within about two hours of awakening from sleep each day.

In another embodiment, the invention provides any of the above-described methods for GH and IGF-1 combination therapy to improve a metabolic abnormality in a patient suffering from a metabolic disorder characterized by partial endogenous growth hormone activity or signaling, wherein the patient is further characterized by having had a growth disorder characterized by partial endogenous growth hormone activity or signaling during childhood.

In another embodiment, the invention provides any of the above-described methods for GH and IGF-1 combination therapy to improve a metabolic abnormality in a patient suffering from a metabolic disorder characterized by partial endogenous growth hormone activity or signaling, wherein the patient does not have partial growth hormone insensitivity syndrome (GHIS).

In some embodiments, the patient receives the single administration of IGF-1 and the single administration of GH by subcutaneous bolus injection each day. In some of these embodiments, the IGF-1 and GH are in the form of a coformulated drug that is administered to the patient by a single injection each day. In other embodiments, the IGF-1 and GH are in the form of separately formulated drugs that are administered to the patient by separate injections.

In addition, the invention provides a modification of any of the above-described methods of treating metabolic disorders in adults in which whatever IGF-1 administration is called for in the subject method is administered to the patient in a single administration of an immediate release formulation of IGF-1, and whatever IGF-1 and GH administration combination is called for in the subject method is (a) administered to the patient in a single administration of an immediate release co-formulation of IGF-1 and GH, (b) administered to the patient in a single administration of an immediate release formulation of IGF-1 and in a single administration of a separate immediate release formulation of GH, or (c) administered to the patient in a single administration of an immediate release formulation of IGF-1 and a separate immediate release formulation of GH that are admixed prior to such administration.

3. Endocrine Disorders Caused by Physiological Stress

The present invention provides methods and compositions for improving metabolic abnormalities in patients suffering from endocrine disorders that are caused by physiological stress and characterized by partial endogenous growth hormone activity or signaling. Typically, patients well suited for the therapies of the invention include patients who acquire growth hormone resistance or another disturbance of the IGF-1/GH axis in response to a physiological stress. The physiological stress can be the patient's underlying disease state, such as cancer, infections, congestive heart failure, rheumatoid arthritis, cystic fibrosis, Crohn's disease, and the like, or the patient's exposure to an environmental stress such as nutritional stress. As a consequence of such physiological stress, the patient can suffer from a variety of metabolic disorders and/or sequelae of such metabolic disorders, including increased blood pressure, decreased cardiac performance, cardiac disease, renal disease, neurological disease, impaired exercise performance, decreased muscle mass, anorexia, cachexia, decreased bone density, osteopenia, osteoporosis, obesity, and abnormalities of lipid and carbohydrate metabolism. The methods of the invention provide therapies for the replacement of normal endocrine function to improve the metabolic health of these patients and to prevent or reduce the medical complications the patient would otherwise experience during the period of endocrine dysfunction and/or thereafter.

In one embodiment, the invention provides a method comprising administering to a patient suffering from an endocrine disorder caused by physiological stress and characterized by partial endogenous growth hormone activity or signaling, an amount of insulin-like growth factor-1 (IGF-1) effective to improve a metabolic abnormality in the patient, wherein the patient receives the amount of IGF-1 in a single administration per day. In some embodiments, the endocrine disorder is cachexia. In other embodiments, the cachexic disorder is a sequela of an underlying cancer in the patient. In other embodiments, the endocrine disorder is anorexia. In other embodiments, the endocrine disorder is anorexia and osteopenia. In other embodiments, the endocrine disorder is anorexia and osteoporosis. In other embodiments, the endocrine disorder is anorexia in patients who are weight recovering but not weight recovered. In other embodiments, the endocrine disorder is anorexia and osteopenia in patients who are weight recovering but not weight recovered. In other embodiments, the endocrine disorder is anorexia and osteoporosis in patients who are weight recovering but not weight recovered. In any of the foregoing embodiments, the improvement in metabolism can be (i) an improvement in bone metabolism, e.g., an improvement in bone mineral density (BMD), (ii) an improvement in nitrogen balance and/or (iii) an increase in body weight or lean body mass. In any of the foregoing embodiments, the patient's anorexic disorder can be anorexia nervosa. In any of the foregoing embodiments, the patient can be a human female. In addition, the invention provides a modification of any of the methods described above in this paragraph, in which the patient receives the single daily administration of IGF-1 at or about the time of breakfast or within about two hours of awakening from sleep each day. In addition, the invention provides a modification of any of the methods of treating osteopenia or osteoporosis described above in this paragraph, in which the patient receives an amount of an anti-resorptive agent, such as estrogen, that in combination with the amount of IGF-1 administered according to the method is effective to improve bone metabolism, e.g., improve bone mineral density (BMD), in the patient.

In another embodiment, the invention provides a method comprising administering to a patient suffering from an endocrine disorder caused by physiological stress and characterized by partial endogenous growth hormone activity or signaling, an amount of insulin-like growth factor-1 (IGF-1) and an amount of growth hormone (GH) that are effective in combination therapy to improve a metabolic abnormality in the patient, wherein the patient receives the amount of IGF-1 in a single administration per day and receives the amount of GH in a single administration per day, and wherein the patient receives the administrations of IGF-1 and GH contemporaneously or substantially contemporaneously. In some embodiments, the endocrine disorder is cachexia. In other embodiments, the cachexic disorder is a sequela of an underlying cancer in the patient. In other embodiments, the endocrine disorder is anorexia. In other embodiments, the endocrine disorder is anorexia and osteopenia. In other embodiments, the endocrine disorder is anorexia and osteoporosis. In other embodiments, the endocrine disorder is anorexia in patients who are weight recovering but not weight recovered. In other embodiments, the endocrine disorder is anorexia and osteopenia in patients who are weight recovering but not weight recovered. In other embodiments, the endocrine disorder is anorexia and osteoporosis in patients who are weight recovering but not weight recovered. In any of the foregoing embodiments, the improvement in metabolism can be (i) an improvement in bone metabolism, e.g., an improvement in bone mineral density (BMD), (ii) an improvement in the nitrogen balance and/or (iii) an increase in body weight or lean body mass. In any of the foregoing embodiments, the patient's anorexic disorder can be anorexia nervosa. In any of the foregoing embodiments, the patient can be a human female. In addition, the invention provides a modification of any of the methods described above in this paragraph, in which the patient receives the single daily administration of IGF-1 and the single daily administration of growth hormone at or about the time of breakfast or within about two hours of awakening from sleep each day. In addition, the invention provides a modification of any of the methods of treating osteopenia or osteoporosis described above in this paragraph, in which the patient receives an amount of an anti-resorptive agent, such as estrogen, that in combination with the amounts of IGF-1 and growth hormone administered according to the method is effective to improve bone metabolism, e.g., improve bone mineral density (BMD), in the patient.

In another embodiment, the invention provides a method comprising administering to a patient suffering from anorexia an amount of insulin-like growth factor-1 (IGF-1) that is effective to improve a metabolic abnormality in the patient, wherein the patient receives the amount of IGF-1 in a single administration per day. In some embodiments, the patient suffering from anorexia is weight recovering but not weight recovered. In any of the foregoing embodiments, the patient's anorexic disorder can be anorexia nervosa. In addition, the invention provides a modification of any of the methods described above in this paragraph, in which the improvement in metabolism is an improvement in bone metabolism and in which the method further comprises administering to the patient an amount of an anti-resorptive agent, such as estrogen, that in combination with the amount of IGF-1 administered according to the method is effective to improve bone metabolism in the patient. In any of the foregoing embodiments, the improvement in metabolism can be (i) an improvement in bone metabolism, e.g., an improvement in bone mineral density (BMD), (ii) an improvement in nitrogen balance and/or (iii) an increase in body weight or lean body mass. In any of the foregoing embodiments, the patient can be a human female. In addition, the invention provides a modification of any of the methods described above in this paragraph, in which the patient receives the single daily administration of IGF-1 at or about the time of breakfast or within about two hours of awakening from sleep each day.

In another embodiment, the invention provides a method comprising administering to a patient suffering from anorexia an amount of insulin-like growth factor-1 (IGF-1) and an amount of growth hormone (GH) that are effective in combination therapy to improve a metabolic abnormality in the patient, wherein the patient receives the amount of IGF-1 in a single administration per day and receives the amount of GH in a single administration per day, and wherein the patient receives the administrations of IGF-1 and GH contemporaneously or substantially contemporaneously. In some embodiments, the patient suffering from anorexia is weight recovering but not weight recovered. In any of the foregoing embodiments, the patient's anorexic disorder can be anorexia nervosa. In addition, the invention provides a modification of any of the methods described above in this paragraph, in which the improvement in metabolism is an improvement in bone metabolism and in which the method further comprises administering to the patient an amount of an anti-resorptive agent, such as estrogen, that in combination with the amounts of IGF-1 and GH administered according to the method is effective to improve bone metabolism in the patient. In any of the foregoing embodiments, the improvement in metabolism can be (i) an improvement in bone metabolism, e.g., an improvement in bone mineral density (BMD), an improvement in nitrogen balance and/or (iii) an increase in body weight or lean body mass. In any of the foregoing embodiments, the patient can be a human female. In addition, the invention provides a modification of any of the methods described above in this paragraph, in which the patient receives the single daily administration of IGF-1 and the single daily administration of growth hormone at or about the time of breakfast or within about two hours of awakening from sleep each day.

In another embodiment, the invention provides a method comprising administering to a patient suffering from anorexia an amount of insulin-like growth factor-1 (IGF-1) effective to prevent, delay the onset of, delay the progression of, reduce the risk of the development of, or reduce the disease burden of, osteoporosis in the patient, wherein the patient receives the amount of IGF-1 in a single administration per day. In some embodiments, the patient suffering from anorexia is weight recovering but not weight recovered. In any of the foregoing embodiments, the patient's anorexic disorder can be anorexia nervosa. In addition, the invention provides a modification of any of the methods described above in this paragraph, in which the method further comprises administering to the patient an amount of an anti-resorptive agent, such as estrogen, that in combination with the amount of IGF-1 administered according to the method is effective to prevent, delay the onset of, delay the progression of, reduce the risk of the development of, or reduce the disease burden of, osteoporosis in the patient. In any of the foregoing embodiments, the method can prevent, delay the onset of, delay the progression of, reduce the risk of the development of, or reduce the disease burden of, osteoporosis in the patient by improving the bone mineral density (BMD) of the patient. In any of the foregoing embodiments, the patient can be a human female. In addition, the invention provides a modification of any of the methods described above in this paragraph, in which the patient receives the single daily administration of IGF-1 at or about the time of breakfast or within about two hours of awakening from sleep each day.

In another embodiment, the invention provides a method comprising administering to a patient suffering from anorexia an amount of insulin-like growth factor-1 (IGF-1) and an amount of growth hormone (GH) that are effective in combination therapy to prevent, delay the onset of, delay the progression of, reduce the risk of the development of, or reduce the disease burden of, osteoporosis in the patient, wherein the patient receives the amount of IGF-1 in a single administration per day and receives the amount of GH in a single administration per day, and wherein the patient receives the administrations of IGF-1 and GH contemporaneously or substantially contemporaneously. In some embodiments, the patient suffering from anorexia is weight recovering but not weight recovered. In any of the foregoing embodiments, the patient's anorexic disorder can be anorexia nervosa. In addition, the invention contemplates a modification of any of the methods described above in this paragraph, in which the method further comprises administering to the patient an amount of an anti-resorptive agent, such as estrogen, that in combination with the amounts of IGF-1 and GH administered according to the method is effective to prevent, delay the onset of, delay the progression of, reduce the risk of the development of, or reduce the disease burden of, osteoporosis in the patient. In any of the foregoing embodiments, the method can prevent, delay the onset of, delay the progression of, reduce the risk of the development of, or reduce the disease burden of, osteoporosis in the patient by improving the bone mineral density (BMD) of the patient. In any of the foregoing embodiments, the patient can be a human female. In addition, the invention provides a modification of any of the methods described above in this paragraph, in which the patient receives the single daily administration of IGF-1 and the single daily administration of growth hormone at or about the time of breakfast or within about two hours of awakening from sleep each day.

In another embodiment, the invention provides a method comprising administering to a patient suffering from anorexia and osteopenia an amount of insulin-like growth factor-1 (IGF-1) effective to prevent, delay the onset of, delay the progression of, reduce the risk of the development of, or reduce the disease burden of, osteoporosis in the patient, wherein the patient receives the amount of IGF-1 in a single administration per day. In some embodiments, the patient suffering from anorexia and osteopenia is weight recovering but not weight recovered. In any of the foregoing embodiments, the patient's anorexic disorder can be anorexia nervosa. In addition, the invention provides a modification of any of the methods described above in this paragraph, in which the method further comprises administering to the patient an amount of an anti-resorptive agent, such as estrogen, that in combination with the amount of IGF-1 administered according to the method is effective to prevent, delay the onset of, delay the progression of, reduce the risk of the development of, or reduce the disease burden of, osteoporosis in the patient. In any of the foregoing embodiments, the method can prevent, delay the onset of, delay the progression of, reduce the risk of the development of, or reduce the disease burden of, osteoporosis in the patient by improving the bone mineral density (BMD) of the patient. In any of the foregoing embodiments, the patient can be a human female. In addition, the invention provides a modification of any of the methods described above in this paragraph, in which the patient receives the single daily administration of IGF-1 at or about the time of breakfast or within about two hours of awakening from sleep each day.

In another embodiment, the invention provides a method comprising administering to a patient suffering from anorexia and osteopenia an amount of insulin-like growth factor-1 (IGF-1) and an amount of growth hormone (GH) that are effective in combination therapy to prevent, delay the onset of, delay the progression of, reduce the risk of the development of, or reduce the disease burden of, osteoporosis in the patient, wherein the patient receives the amount of IGF-1 in a single administration per day and receives the amount of GH in a single administration per day, and wherein the patient receives the administrations of IGF-1 and GH contemporaneously or substantially contemporaneously. In some embodiments, the patient suffering from anorexia and osteopenia is weight recovering but not weight recovered. In any of the foregoing embodiments, the patient's anorexic disorder can be anorexia nervosa. In addition, the invention provides a modification of any of the methods described above in this paragraph, in which the method further comprises administering to the patient an amount of an anti-resorptive agent, such as estrogen, that in combination with the amounts of IGF-1 and GH administered according to the method is effective to prevent, delay the onset of, delay the progression of, reduce the risk of the development of, or reduce the disease burden of, osteoporosis in the patient. In any of the foregoing embodiments, the method can prevent, delay the onset of, delay the progression of, reduce the risk of the development of, or reduce the disease burden of, osteoporosis in the patient by improving the bone mineral density (BMD) of the patient. In any of the foregoing embodiments, the patient can be a human female. In addition, the invention provides a modification of any of the methods described above in this paragraph, in which the patient receives the single daily administration of IGF-1 and the single daily administration of growth hormone at or about the time of breakfast or within about two hours of awakening from sleep each day.

In another embodiment, the invention provides a method comprising administering to a patient suffering from anorexia and osteoporosis an amount of insulin-like growth factor-1 (IGF-1) effective to delay the progression or reduce the disease burden of osteoporosis in the patient, wherein the patient receives the amount of IGF-1 in a single administration per day. In some embodiments, the patient suffering from anorexia and osteoporosis is weight recovering but not weight recovered. In any of the foregoing embodiments, the patient's anorexic disorder can be anorexia nervosa. In addition, the invention provides a modification of the any of the methods described above in this paragraph, in which the method further comprises administering to the patient an amount of an anti-resorptive agent, such as estrogen, that in combination with the amount of IGF-1 administered according to the method is effective to delay the progression or reduce the disease burden of osteoporosis in the patient. In any of the foregoing embodiments, the method can delay the progression or reduce the disease burden of osteoporosis in the patient by improving the bone mineral density (BMD) of the patient. In any of the foregoing embodiments, the patient can be a human female. In addition, the invention provides a modification of any of the methods described above in this paragraph, in which the patient receives the single daily administration of IGF-1 at or about the time of breakfast or within about two hours of awakening from sleep each day.

In another embodiment, the invention provides a method comprising administering to a patient suffering from anorexia and osteoporosis an amount of insulin-like growth factor-1 (IGF-1) and an amount of growth hormone (GH) that are effective in combination therapy to delay the progression or reduce the disease burden of osteoporosis in the patient, wherein the patient receives the amount of IGF-1 in a single administration per day and receives the amount of GH in a single administration per day, and wherein the patient receives the administrations of IGF-1 and GH contemporaneously or substantially contemporaneously. In some embodiments, the patient suffering from anorexia and osteoporosis is weight recovering but not weight recovered. In any of the foregoing embodiments, the patient's anorexic disorder can be anorexia nervosa. In addition, the invention provides a modification of any of the methods described above in this paragraph, in which the method further comprises administering to the patient an amount of an anti-resorptive agent, such as estrogen, that in combination with the amounts of IGF-1 and GH administered according to the method is effective to delay the progression or reduce the disease burden of osteoporosis in the patient. In any of the foregoing embodiments, the method can delay the progression or reduce the disease burden of osteoporosis in the patient by improving the bone mineral density (BMD) of the patient. In any of the foregoing embodiments, the patient can be a human female. In addition, the invention provides a modification of any of the methods described above in this paragraph, in which the patient receives the single daily administration of IGF-1 and the single daily administration of growth hormone at or about the time of breakfast or within about two hours of awakening from sleep each day.

In another embodiment, the invention provides a method comprising administering to a patient suffering from cachexia an amount of insulin-like growth factor-1 (IGF-1) effective to improve nitrogen balance in the patient, wherein the patient receives the amount of IGF-1 in a single administration per day. In addition, the invention provides a modification of any of the methods described above in this paragraph, in which the patient receives the single daily administration of IGF-1 at or about the time of breakfast or within about two hours of awakening from sleep each day.

In another embodiment, the invention provides a method comprising administering to a patient suffering from cachexia an amount of insulin-like growth factor-1 (IGF-1) and an amount of growth hormone (GH) that are effective in combination therapy to improve nitrogen balance or increase body weight or lean body mass in the patient, wherein the patient receives the amount of IGF-1 in a single administration per day and receives the amount of GH in a single administration per day, and wherein the patient receives the administrations of IGF-1 and GH contemporaneously or substantially contemporaneously. In addition, the invention provides a modification of any of the methods described above in this paragraph, in which the patient receives the single daily administration of IGF-1 and the single daily administration of growth hormone at or about the time of breakfast or within about two hours of awakening from sleep each day.

In addition, the invention provides a modification of any of the above-described methods of treating patients suffering from anorexia, cachexia or other endocrine disorders caused by physiological stress and characterized by partial endogenous growth hormone activity or signaling, in which whatever IGF-1 administration is called for in the subject method is administered to the patient in a single administration of an immediate release formulation of IGF-1, and whatever IGF-1 and GH administration combination is called for in the subject method is (a) administered to the patient in a single administration of an immediate release co-formulation of IGF-1 and GH, (b) administered to the patient in a single administration of an immediate release formulation of IGF-1 and in a single administration of a separate immediate release formulation of GH, or (c) administered to the patient in a single administration of an immediate release formulation of IGF-1 and a separate immediate release formulation of GH that are admixed prior to such administration.

It will be appreciated that any of the methods of the present invention calling for the administration of estrogen can be modified to employ another bone resorption inhibiting agent in place of, or in addition to, the estrogen therapy specified in the subject method. In addition, such methods can be practiced by co-administering, either simultaneously or sequentially with the anabolic drug(s) specified in the subject method (IGF-1 administration or IGF-1 and GH administration combination), a bone resorption inhibiting agent. The bone resorption-inhibiting agent can be a bisphosphonate, estrogen, a selective estrogen receptor modulator, a selective androgen receptor modulator, calcitonin, a vitamin D analog, or a calcium salt. The bone resorption-inhibiting agent can also be alendronate, risedronate, etidronate, pamidronate, tiludronate, zoledronic acid, raloxifene, tamoxifen, droloxifene, toremifene, idoxifene, levormeloxifene, or conjugated estrogens. In one embodiment, the patient receives intermittent administration of the anabolic drug(s) for a three-month period of time, followed by a three-month period of treatment with a bone resorption-inhibiting agent. A skilled artisan will recognize that the sequential treatment regimen could begin with a treatment period with a bone resorption inhibiting agent followed by a treatment period with the anabolic drug(s), that the length of sequential treatment periods can be modified (e.g., 1-18 months), and that the anabolic drug(s) can be concurrently administered with the bone resorption inhibiting agent (e.g., sequential treatment period of anabolic drug(s) and a bone resorption inhibiting agent followed by a treatment period of a bone resorption inhibiting agent alone or anabolic drug(s) alone). The sequential treatment periods (e.g., three months of the anabolic drug(s) followed by three month of the bone resorption inhibiting agent) can be repeated until the patient BMD is restored (e.g., a T-score <−2.0 or −2.5 below the mean).

In a preferred embodiment, any of the above-described methods that specify the administration of an anti-resorptive agent is modified to use a commercially available anti-resorptive drug selected from the group of estrogens, such as conjugated estrogens (Premarin™); selective estrogen receptor modulators (SERMs), such as raloxifene (Evista™); calcitonin (Miacalcin™); and bisphosphonates, such as alendronate (Fosamax™), risedronate (Actonel™), etidronate (Didronel™), pamidronate (Aredia™), tiludronate (Skelid™), and zoledronic acid (Zometa™).

Administration of IGF-1

The present invention provides methods and compositions for increasing the height and growth rates and improving the metabolism of patients with IGFD by administering to the patients an effective amount of IGF-1. In addition, the present invention provides methods and compositions for improving metabolism in patients suffering from anorexia, cachexia or other endocrine disorders caused by physiological stress and characterized by partial endogenous growth hormone activity or signaling, by administering to the patients an effective amount of IGF-1. In some embodiments, native human IGF-1 is used. In other embodiments, IGF-1 variants are used.

Suitable for use in the subject methods are IGF-1 variants. IGF-1 variants can be designed that retain efficient binding to the type I IGF receptor, yet would have reduced binding to serum carrier proteins, e.g. IGFBPs. In one aspect, the design of these variants is based on the observation that insulin does not bind to serum carrier proteins. See U.S. Pat. No. 4,876,242, issued Oct. 24, 1989, herein expressly incorporated by reference in its entirety. Evidence from synthetic, insulin-like two chain analogs suggests that amino acids of IGF-1 responsible for carrier protein binding are in the B region of IGF-1. Therefore a synthetic gene for human IGF-1 can be modified to encode an IGF-1 variant in which the first 16 amino acids of hIGF-1 are replaced by the first 17 amino acids of the B chain of human insulin. The synthetic gene is then placed in a yeast recombinant DNA expression system and the peptide analog which is produced by the modified yeast cells is extracted therefrom and purified. Additional modifications of the IGF-1 molecule have been carried out leading to additional analogs, all of which have substantial IGF-1 type I receptor binding and reduced binding to serum carrier proteins.

Other IGF-1 variants and analogs well known in the art are also suitable for use in the subject methods. Such variants include, for example, the variant having resides 1-69 of authentic IGF-1, further described in WO 96/33216, and the two-chain IGF-1 superagonists which are derivatives of the naturally occurring single-chain IGF-1 having an abbreviated C domain, further described in EP 742,228. IGF-1 analogs are of the formula: BC$^n$, A wherein B is the B domain of IGF-1 or a functional analog thereof, C is the C domain of IGF-1 or a functional analog thereof, n is the number of amino acids in the C domain and is from about 6 to about 12 amino acids, including about 8 to about 10 amino acids, and A is the A domain of IGF-1 or a functional analog thereof.

Also suitable for use in the subject methods are functional mutants of IGF-1 that are well known in the art. Such functional mutants include those described in Cascieri et al. (1988, Biochemistry 27:3229-3233), which discloses four mutants of IGF-1, three of which have reduced affinity to the Type I IGF receptor. These mutants are: (Phe$^{23}$, Phe$^{24}$, Tyr$^{25}$) IGF-1 (which is equipotent to human IGF-1 in its affinity to the Types 1 and 2 IGF and insulin receptors), (Leu$^{24}$)IGF-1 and (Ser$^{24}$)IGF-1 (which have a lower affinity than IGF-1 to the human placental Type I IGF receptor, the placental insulin receptor, and the Type I IGF receptor of rat and mouse cells), and desoctapeptide (Leu$^{24}$)IGF-1 (in which the loss of aromaticity at position 24 is combined with the deletion of the carboxyl-terminal D region of hIGF-1, which has lower affinity than (Leu$^{24}$)IGF-1 for the Type I receptor and higher affinity for the insulin receptor). These four mutants have normal affinities for human serum binding proteins.

Also suitable for use with the subject methods include structural analogs of IGF-1 well known in the art. Such structural analogs include those described in Bayne et al. (1988, J Biol Chem 264:11004-11008), which discloses three structural analogs of IGF-1: (1-62)IGF-1, which lacks the carboxyl-terminal 8-amino-acid D region of IGF-1; (1-27, Gly$^4$, 38-70)IGF-1, in which residues 28-37 of the C region of IGF-1 are replaced by a four-residue glycine bridge; and (1-27, Gly$^4$, 38-62) IGF-1; with a C region glycine replacement and a D region deletion. Peterkofsky et al. (1991, Endocrinology, 128: 1769-1779) discloses data using the Gly$^4$ mutant of Bayne et al., supra. U.S. Pat. No. 5,714,460 refers to using IGF-1 or a compound that increases the active concentration of IGF-1 to treat neural damage.

Other structural analogs include those described in Cascieri et al. (1989, J Biol Chem, 264: 2199-2202) discloses three IGF-1 analogs in which specific residues in the A region of IGF-1 are replaced with the corresponding residues in the A chain of insulin. The analogs are: (Ile$^{41}$, Glu$^{45}$, Gln$^{46}$, Thr$^{49}$, Ser$^{50}$, Ile$^{51}$, Ser$^{53}$, Tyr$^{55}$, Gln$^{56}$)IGF-1, an A chain mutant in which residue 41 is changed from threonine to isoleucine and residues 42-56 of the A region are replaced; (Thr$^{49}$, Ser$^{50}$, Ile$^{51}$)IGF-1; and (Tyr$^{55}$, Gln$^{56}$)IGF-1.

Combination Therapy

In another aspect, the IGF-1 regimens and/or the IGF-1 and GH combination regimens of the invention can be modified to include the use of additional growth-promoting agents. Additional growth-promoting agents suitable for use in conjunction with the IGF-1 therapies or IGF-1 and GH combination therapies of the invention include agents that increase total IGF-1 levels in the blood or enhance the effect of the IGF-1. In one embodiment, these additional reagents generally allow an excess of blood IGF-1 over the amount of IGFBPs in blood or the IGF-1 to be released from IGFBPs, and include growth-promoting agents.

Growth-promoting agents for this purpose include, but are not limited to, GH secretagogues that promote the release of endogenous GH in mammals to increase concentrations of the IGF in the blood. Examples include TRH, diethylstilbestrol, theophylline, enkephalins, E series prostaglandins, peptides of the VIP-secretin-glucagon-GRF family, and other GH secretagogues such as GHRP-6, GHRP-1 as described in U.S. Pat. No. 4,411,890, and benzo-fused lactams such as those disclosed in U.S. Pat. No. 5,206,235. See also, e.g., WO 96/15148 published May 23, 1996. Other growth-promoting agents include GHRPs, GHRHs, GH and their analogs. For example, GHRPs are described in WO 95/17422 and WO 95/17423 both published Jun. 29, 1995; Bowers, J, 1993, Pediatr Endocrinol, 6:21-31; and Schoen et al., 1993, Annual Reports in Medicinal Chemistry, 28: 177-186. GHRHs and their analogs are described, for example, in WO 96/37514 published Nov. 28, 1996.

The agent can be co-administered sequentially or simultaneously with the IGF-1 administration or IGF-1 and GH co-administration provided in the method of the invention, and may be administered in the same, higher, or a lower dose than if used alone depending on such factors as, for example, the type of reagent used, the purpose for which the reagent and compound are being used, and clinical considerations. In addition, other means of manipulating IGF status, such as regimens of diet or exercise, are also considered to be combination treatments as part of this invention.

In another embodiment, IGF-1 is appropriately administered together with any one or more of its binding proteins, for example, IGFBP-1, IGFBP-2, IGFBP-3, IGFBP-4, IGFBP-5, or IGFBP-6. Without being bound by a mechanism, co-administration of IGF-1 and an IGFBP may provide a greater response than IGF-1 alone by increasing the half-life of IGF-1.

A binding protein suitable for use is IGFBP-3, which is described in U.S. Pat. No. 5,258,287 and by Martin and Baxter, 1986, J Biol Chem, 261: 8754-8760. This glycosylated IGFBP-3 protein is an acid-stable component of about 53 Kd on a non-reducing SDS-PAGE gel of a 125-150 Kd glycoprotein complex found in human plasma that carries most of the endogenous IGFs and is also regulated by GH.

The administration of the IGF binding protein with IGF-1 may be accomplished by the method described in U.S. Pat. No. 5,187,151. Briefly, the IGF-1 and IGFBP are administered in effective amounts by subcutaneous bolus injection in a molar ratio of from about 0.5:1 to about 3:1, including about 0.75:1 to about 2:1, such as about 1:1.

Anti-Resporptive Therapy

Whenever the above-described methods call for the administration of anti-resorptive agents, the practitioner may use any commercially available pharmaceutical product suitable for the inhibition of bone resorption, including conjugated estrogens, such as Premarin™, selective estrogen receptor modulators (SERMs), such as raloxifene (Evista™), calcitonin (Miacalcin™), and bisphosphonates, such as alendronate (Fosamax™), risedronate (Actonel™), etidronate (Didronel™), pamidronate (Aredia™), tiludronate (Skelid™), and zoledronic acid (Zometa™), according to the dosage(s), route(s) of administration, protocol(s), and regimen(s) specified in the product's package insert.

Subjects Suitable for Treatment

Subjects suitable for treatment with the methods disclosed herein include subjects that suffer from a growth disorder characterized by partial endogenous growth hormone activity or signaling. In general, the growth disorder patient population has, for example, the following characteristics: 1) a height at least about 2 standard deviations (SD) below the normal mean for the corresponding age and gender, and 2) a blood level of IGFBP-3 that is below, but not more than 2 SD below, normal mean levels for the subject's corresponding age and gender. In one embodiment, the present invention encompasses methods for treating IGFD children who do not have a blood level of high-affinity growth hormone binding protein that is at least 2 SDs below normal mean levels, and do not have Laron syndrome. In another embodiment, the present invention encompasses methods for treating IGFD children who do not have a blood level of high-affinity growth hormone binding protein that is at least 2 SDs below normal mean levels, and do not have partial growth hormone insensitivity syndrome (partial GHIS).

In one embodiment, the present invention encompasses methods for treating IGFD children who have a mean or maximum stimulated blood level of growth hormone which is at least within the normal range.

In certain embodiments, the subject suffering from IGFD has a height, for example, of at least about 2.0 SD below the normal mean for a corresponding age and gender, at least about 2.5 SD below the normal mean for a corresponding age and gender (i.e., −2.5 SD), or at least about 3.0 SD below the normal mean for a corresponding age and gender, usually at least about usually between about 2.0 SD and about 3.0 SD below the normal mean for a corresponding age and gender, between about 2.5 SD and about 3.0 SD below the normal mean for a corresponding age and gender, or at least about 3.0 SD below the normal mean for a corresponding age and gender. In certain embodiments, the subject suffering from IGFD has a blood level of IGF-1 at least 1 SD below the normal range for their corresponding age and gender. IGF-1 deficient subjects can have blood levels of IGF-1 that are, for example, at least about 2.0 SD below normal mean levels for a corresponding age and gender, at least about 3.0 SD below normal mean levels for a corresponding age and gender, usually from about 2.0 SD to about 3.0 SD below normal mean levels for the corresponding age and gender. An IGFD patient may also have blood levels of high affinity growth hormone binding protein less than the normal mean, but not more than 2SD below the normal mean. In certain embodiments, the blood level of high-affinity growth hormone binding protein is between normal mean levels and −0.5 SD below normal mean levels, between normal mean levels and 0.5 SD below normal mean levels, between 0.5 SD and 1.0 SD below normal mean levels, between 1.0 SD and 1.5 SD below normal mean levels, or between 1.5 SD and 2.0 SD below normal mean levels.

Short stature patients who will benefit from increased IGF-1 levels can be identified using routine methods known in the art. IGF-1 levels can be detected in blood. A genetic abnormality associated with IGF-1 can be detected using standard genetic assays. A marker for a local IGF-1 deficit (such as levels of IGFBP-1) can be detected using routine assays.

Measuring IGF levels in a biological fluid such as a body or blood fluid can be done by any means, including RIA and ELISA. For example, total IGF-1 in the blood can be determined by commercially available radioimmunoassays (Medgenix Diagnostics, Brussels, Belgium; IGF-1 RIA Kit, Nichols Institute, San Juan Capistrano, Calif.) especially after the extraction of the blood sample using acid ethanol to remove binding proteins which interfere with the detection of the IGF-1 by competing with anti-IGF-1 antibody. IGFBP can be measured using commercially available immunoradiometric assays (IRMAs) for measuring IGFBP-1 and IGFBP-3 (Diagnostic System Laboratories Inc., Webster, Tex.).

Another method involves measuring the level of "free" or active IGF in blood. For example, one method is described in U.S. Pat. No. 5,198,340, herein expressly incorporated by reference in its entirety. An additional method is described in U.S. Pat. No. 6,251,865, issued Jun. 26, 2001, herein expressly incorporated by reference in its entirety, for detecting endogenous or exogenous IGF bound to an IGF binding protein or the amount of a compound that binds to an IGF binding protein and does not bind to a human IGF receptor bound to an IGF binding protein or detecting the level of unbound IGF in a biological fluid. This method comprises: (a) contacting the fluid with 1) a means for detecting the compound that is specific for the compound (such as a first antibody specific for epitopes on the compound) attached to a solid-phase carrier, such that in the presence of the compound the IGF binding sites remain available on the compound for binding to the IGF binding protein, thereby forming a complex between the means and the IGF binding protein; and 2) the compound for a period of time sufficient to saturate all available IGF binding sites on the IGF binding protein, thereby forming a saturated complex; (b) contacting the saturated complex with a detectably labeled second means which is specific for the IGF binding protein (such as a second antibody specific for epitopes on the IGFBP) which are available for binding when the compound is bound to the IGF binding protein; and (c) quantitatively analyzing the amount of the labeled means bound as a measure of the IGFBP in the biological fluid, and therefore as a measure of the amount of bound compound and IGF binding protein, bound IGF and IGF binding protein, or active IGF present in the fluid.

U.S. Pat. Nos. 5,593,844 and 5,210,017, herein expressly incorporated by reference in their entireties, disclose a ligand-mediated immunofunctional binding protein assay method that can be used to quantitate the amount of IGFBP in a liquid sample by the use of antibodies, where complex formation takes place between one of these binding proteins and the ligand that binds to it.

The quantitative technique mentioned above using antibodies, called the ligand-mediated immunofunctional method (LIFA), is described for determining the amount of IGFBP by contact with IGF in U.S. Pat. No. 5,593,844, herein expressly incorporated by reference in its entirety.

Measurement of Bone Mass

Several noninvasive techniques are now available for estimating skeletal mass or density. These include dual-energy x-ray absorptiometry (DXA), single-energy x-ray absorptiometry (SXA), quantitative computed tomography (CT), and ultrasound.

DXA is a highly accurate x-ray technique that has become the standard for measuring bone density in most centers. Though it can be used for measurements of any skeletal site, clinical determinations are usually made of the lumbar spine and hip. Portable DXA machines have been developed that measure the heel (calcaneus), forearm (radius and ulna), or finger (phalanges), and DXA can also be used to measure body composition. In the DXA technique, two x-ray energies are used to estimate the area of mineralized tissue, and the mineral content is divided by the area, which partially corrects for body size. However, this correction is only partial since DXA is a two-dimensional scanning technique and cannot estimate the depths or posteroanterior length of the bone. Thus, small people tend to have lower-than-average bone mineral density (BMD). Newer DXA techniques that measure information BMD are currently under evaluation. Bone spurs, which are frequent in osteoarthritis, tend to falsely increase bone density of the spine. Because DXA instrumentation is provided by several different manufacturers, the output varies in absolute terms. Consequently, it has become standard practice to relate the results to "normal" values using T-scores, which compare individual results to those in a normal young adult population that is matched for race and gender. Alternatively, Z-scores compare individual results to those of an age-matched population that is also matched for race and gender. Thus, a 60-year-old woman with a Z-score of −1 (1 SD below mean for age) could have a T-score of −2.5 (2.5 SD below mean for a young control group).

CT is used primarily to measure the spine, and peripheral CT is used to measure bone in the forearm or tibia. Research into the use of CT for measurement of the hip is ongoing. CT has the added advantage of studying bone density in subtypes of bone, e.g., trabecular vs. cortical. The results obtained from CT are different from all others currently available since this technique specifically analyzes trabecular bone and can provide a true density (mass of bone per unit volume) measurement. However, CT remains expensive, involves greater radiation exposure, and is less reproducible.

Ultrasound is used to measure bone mass by calculating the attenuation of the signal as it passes through bone or the speed with which it traverses the bone. It is unclear whether ultrasound assesses bone quality, but this may be an advantage of the technique. Because of its relatively low cost and mobility, ultrasound is amenable for use as a screening procedure.

All of these techniques for measuring BMD have been approved by the U.S. Food and Drug Administration (FDA) based upon their capacity to predict fracture risk. The hip is the preferred site of measurement in most individuals, since it directly assesses bone mass at an important fracture site. When hip measurements are performed by DXA, the spine can be measured at the same time. In younger individuals, such as perimenopausal women, spine measurements may be the most sensitive indicator of bone loss.

Measurement of Nitrogen Balance

Any known method of calculating or estimating a patient's nitrogen balance can by utilized for patient diagnosis or evaluation of patient outcomes in connection with the present methods of treating endocrine disorders. The monitoring of urinary excretion of nitrogen can be used to estimate nitrogen balance as described in U.S. Pat. No. 5,348,979. Urinary nitrogen can be quantitated by the Kjeldahl method, e.g., as described in the "Guide to Kjeldahl Nitrogen Determination Methods and Apparatus" published in 1998 by Labconco Corporation, 8811 Prospect Avenue, Kansas City, Mo. 64132-2696.

Measurement of Body Weight or Lean Body Mass

Any known method of calculating or estimating a patient's body weight or lean body mass, including estimates of lean body mass and body fat mass, can by utilized for patient diagnosis or evaluation of patient outcomes in connection with the present methods of treating endocrine disorders.

Dosage and Schedule of Administration

Selection of the therapeutically effective dose can be determined (e.g., via clinical trials) by a skilled artisan, such as a clinician or a physician, based upon the consideration of several factors which will be known to one of ordinary skill in the art. Such factors include, for example, the particular form of IGF-1, and the compound's pharmacokinetic parameters such as bioavailability, metabolism, half-life, and the like, which is established during the development procedures typically employed in obtaining regulatory approval of a pharmaceutical compound. Further factors in considering the dose include the disease or condition to be treated, the benefit to be achieved in a subject, the subject's body mass, the subject's immune status, the route of administration, whether administration of the compound or combination therapeutic agent is acute or chronic, concomitant medications, and other factors known by the skilled artisan to affect the efficacy of administered pharmaceutical agents.

The identification and treatment of IGFD as a new condition has direct parallels with the identification and treatment of GHD. It has been noted by others (Drake et al., 2001, *Endocrine Reviews* 22: 425-450) that it was only the advent of modern neuro-radiological imaging techniques in 1989 that allowed the diagnosis of GH deficiency in adults to be established with certainty. It was this identification of patients with small or damaged pituitaries and low IGF-1 levels and low GH levels that greatly assisted in establishing a diagnosis of adult GHD. It was also therefore only relatively recently that it was recognized that there is a characteristic clinical syndrome associated with failure of spontaneous GH secretion and that the use of recombinant GH to reverse many of its features has become established.

In terms of how to treat with IGF-1 it is instructive to consider the methods by which GH replacement therapy is practiced. In adults there is no biological marker of GH action that is the equivalent of height or growth in a child. Therefore it is difficult to judge the efficacy of GH replacement in adults. The assessment of optimal GH replacement is made difficult by the occurrence of side effects if too high doses are administered. GH treatment is therefore begun at low doses, with doses then being increased to the dose that is the final maintenance dose. It is further very instructive that appropriate GH dosing in adults is best determined by the measurement of blood levels of IGF-1, so as to avoid supra-physiological levels of IGF-1.

In addition the use of growth hormone antagonists has also been instructive. In states of GH excess (such as acromegaly) the current aim of treatment with growth hormone antagonists is to reduce IGF-1 levels into the normal range. The measurement of blood levels of IGF-1 has been characterized as a sensitive and specific indicator for the presence acromegaly and the persistence of disease after therapy (Freda, 2003, GH and IGF Research 13:171-184).

There are now normative data on blood levels of IGF-1 that have been measured in many thousands of patients so that IGF-1 standard deviation scores (IGF-1 SDS) have been established (Juul, G H and IGF Research 13, 113-170, 2003). Just as in children these normative data are age and gender adjusted to establish the normative range for a subject at a given age and gender.

It is clearly a parallel argument that appropriate replacement therapy in adults (and in children) is to establish doses of IGF-1 that raise IGF-1 levels into the age adjusted normal range. There has been much recent work to establish the normal range of IGF-1 levels in children and adults (Juul, G H and IGF Research 13, 113-170, 2003, herein expressly incorporated by reference in its entirety).

In some embodiments, the total pharmaceutically effective amount of IGF-1 administered parenterally per dose will be in the range of about 10 µg/kg/day to about 400 µg/kg/day, including about 20 µg/kg/day to about 200 µg/kg/day, such as, about 40 µg/kg/day to about 100 µg/kg/day, of subject body weight, although, this will be subject to a great deal of therapeutic discretion. Preferred doses for adults are in the range of about 10 µg/kg/day to about 160 µg/kg/day. Other doses of interest for adults are in the range of about 10 µg/kg/day to about 180 µg/kg/day In some embodiments of particular interest, 20 to 240 µg/kg/day IGF-1 is administered to the subject. The IGF-1 may be administered by any means suitable for the delivery of a single administration of drug per day, including injections. In certain embodiments, the IGF-1 is administered once per day by subcutaneous bolus injection. If a slow release formulation is used, typically the dosages used (calculated on a daily basis) will be less, up to one-half of those described above.

The present invention further provides methods for increasing growth rate using a pharmaceutical composition of IGF-1, and a pharmaceutically acceptable carrier. Suitable pharmaceutically acceptable carriers include essentially chemically inert and nontoxic pharmaceutical compositions that do not interfere with the effectiveness of the biological activity of the pharmaceutical composition. Examples of suitable pharmaceutical carriers include, but are not limited to, saline solutions, glycerol solutions, ethanol, N-(1(2,3-dioleyloxy)propyl)-N,N,N-trimethylammonium chloride (DOTMA), diolesylphosphotidylethanolamine (DOPE), and liposomes. Such pharmaceutical compositions should contain a therapeutically effective amount of the compound, together with a suitable amount of carrier so as to provide the form for proper administration to the subject. The formulation should suit the mode of administration. For example, oral administration requires enteric coatings to protect the compounds of the invention from degradation within the gastrointestinal tract. In another example, the compounds of the invention may be administered in a liposomal formulation, particularly for nucleic acids, to shield the compounds from degradative enzymes, facilitate transport in circulatory system, and effect delivery across cell membranes to intracellular sites.

In another embodiment, a pharmaceutical composition comprises an IGF-1 protein, and/or one or more therapeutic agents; and a pharmaceutically acceptable carrier. In one embodiment, a pharmaceutical composition, comprising a IGF-1 protein, with or without other therapeutic agents; and a pharmaceutically acceptable carrier, is at an effective dose.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In some embodiments, the composition is formulated in accordance with routine procedures as a pharmaceutical composition adapted for subcutaneous injection or intravenous administration to humans. Typically, pharmaceutical compositions for subcutaneous injection or intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where the composition is to be administered by infusion, it can be dispensed with an infusion bottle, bag, or other acceptable container, containing sterile pharmaceutical grade water, saline, or other acceptable diluents. Where the composition is administered by injection, an ampule of sterile water for injection or saline can be provided so that the ingredients may be mixed prior to administration.

In certain embodiments, the formulation for IGF-1 is that described in U.S. Pat. No. 5,681,814. This formulation is as follows: about 2 to about 20 mg/ml of IGF-1, about 2 to about 50 mg/ml of an osmolyte, about 1 to about 15 mg/ml of at least one stabilizer, and a buffer (such as an acetic acid salt buffer, or sodium acetate) in an amount such that the composition has a pH of about 5 to about 5.5. Optionally, the formulation may also contain a surfactant, preferably in an amount of about 1 to about 5 mg/ml, such as about 1 to about 3 mg/ml.

In some embodiments, the osmolyte is an inorganic salt at a concentration of about 2-10 mg/ml or a sugar alcohol at a concentration of about 40 to about 50 mg/ml, the stabilizer is benzyl alcohol, phenol, or both, and the buffered solution is an acetic acid salt buffered solution. In further embodiments, the osmolyte is an inorganic salt, such as sodium chloride.

In yet further embodiments, the formulation includes about 8 to about 12 mg/ml of IGF-1, about 5 to about 6 mg/ml of sodium chloride, benzyl alcohol as the stabilizer in an amount of about 8 to about 10 mg/ml and/or phenol in an amount of about 2 to about 3 mg/ml, and about 50 mM sodium acetate buffer so that the pH is about 5.4. Optionally, the formulation contains polysorbate as a surfactant in an amount of about 1 to about 3 mg/ml.

Pharmaceutical compositions adapted for oral administration may be provided, for example, as capsules or tablets; as powders or granules; as solutions, syrups or suspensions (in aqueous or non-aqueous liquids); as edible foams or whips; or as emulsions. Tablets or hard gelatine capsules may comprise, for example, lactose, starch or derivatives thereof, magnesium stearate, sodium saccharine, cellulose, magnesium carbonate, stearic acid or salts thereof. Soft gelatine capsules may comprise, for example, vegetable oils, waxes, fats, semisolid, or liquid polyols, etc. Solutions and syrups may comprise, for example, water, polyols and sugars.

An active agent intended for oral administration may be coated with or admixed with a material (e.g., glyceryl monostearate or glyceryl distearate) that delays disintegration or affects absorption of the active agent in the gastrointestinal tract. Thus, for example, the sustained release of an active agent may be achieved over many hours and, if necessary, the active agent can be protected from being degraded within the gastrointestinal tract. Taking advantage of the various pH and enzymatic conditions along the gastrointestinal tract, pharmaceutical compositions for oral administration may be formulated to facilitate release of an active agent at a particular gastrointestinal location.

Pharmaceutical compositions adapted for parenteral administration include, but are not limited to, aqueous and non-aqueous sterile injectable solutions or suspensions, which may contain antioxidants, buffers, bacteriostats and solutes that render the pharmaceutical compositions substantially isotonic with the blood of an intended recipient. Other components that may be present in such pharmaceutical compositions include water, alcohols, polyols, glycerine and vegetable oils, for example. Compositions adapted for parenteral administration may be presented in unit-dose or multi-dose containers, for example, sealed ampules and vials, and may be stored in a freeze-dried (lyophilized) condition requiring the addition of a sterile liquid carrier, e.g., sterile saline solution for injections, immediately prior to use. Extemporaneous injection solutions and suspensions may be prepared from sterile powders, granules and tablets. Such pharmaceutical compositions should contain a therapeutically or cosmetically effective amount of a compound which increases IGF-1 blood levels, together with a suitable amount of carrier so as to provide the form for proper administration to the subject. The formulation should suit the mode of administration.

Pharmaceutical compositions adapted for transdermal administration may be provided as discrete patches intended to remain in intimate contact with the epidermis for a prolonged period of time. Pharmaceutical compositions adapted for topical administration may be provided as, for example, ointments, creams, suspensions, lotions, powders, solutions, pastes, gels, sprays, aerosols or oils. A topical ointment or cream is preferably used for topical administration to the skin, mouth, eye or other external tissues. When formulated in an ointment, the active ingredient may be employed with either a paraffinic or a water-miscible ointment base. Alternatively, the active ingredient may be formulated in a cream with an oil-in-water base or a water-in-oil base.

Pharmaceutical compositions adapted for topical administration to the eye include, for example, eye drops or injectable pharmaceutical compositions. In these pharmaceutical compositions, the active ingredient can be dissolved or suspended in a suitable carrier, which includes, for example, an aqueous solvent with or without carboxymethylcellulose. Pharmaceutical compositions adapted for topical administration in the mouth include, for example, lozenges, pastilles and mouthwashes.

Pharmaceutical compositions adapted for nasal administration may comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, pharmaceutical compositions adopted for nasal administration may comprise liquid carriers such as, for example, nasal sprays or nasal drops. These pharmaceutical compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient.

Pharmaceutical compositions adapted for rectal administration may be provided as suppositories or enemas. Pharmaceutical compositions adapted for vaginal administration may be provided, for example, as pessaries, tampons, creams, gels, pastes, foams or spray formulations.

Suppositories generally contain active ingredients in the range of 0.5% to 10% by weight. Oral formulations preferably contain 10% to 95% active ingredient by weight.

In yet another embodiment, IGF-1 may be administered using long-acting IGF-1 formulations that either delay the clearance of IGF-1 from the site or cause a slow release of IGF-1 from, e.g., an injection or administration site. The long-acting formulation that prolongs IGF-1 plasma clearance may be in the form of IGF-1 complexed, or covalently conjugated (by reversible or irreversible bonding) to a macromolecule such as a water-soluble polymer selected from PEG and polypropylene glycol homopolymers and polyoxyethylene polyols, i.e., those that are soluble in water at room temperature. See, e.g., U.S. Pat. No. 5,824,642, hereby expressly incorporated by reference in its entirety. Alternatively, the IGF-1 may be complexed or bound to a polymer to increase its circulatory half-life. Examples of polyethylene polyols and polyoxyethylene polyols useful for this purpose include polyoxyethylene glycerol, polyethylene glycol, polyoxyethylene sorbitol, polyoxyethylene glucose, or the like. The glycerol backbone of polyoxyethylene glycerol is the same backbone occurring in, for example, animals and humans in mono-, di-, and triglycerides. The polymer need not have any particular molecular weight, but it is preferred that the molecular weight be between about 3500 and 100,000, more preferably between 5000 and 40,000. Preferably the PEG homopolymer is unsubstituted, but it may also be substituted at one end with an alkyl group. Preferably, the alkyl group is a C1-C4 alkyl group, and most preferably a methyl group. Most preferably, the polymer is an unsubstituted homopolymer of PEG, a monomethyl-substituted homopolymer of PEG (mPEG), or polyoxyethylene glycerol (POG) and has a molecular weight of about 5000 to 40,000.

The IGF-1 may also be coupled to a receptor or antibody or antibody fragment for administration.

Administration of the pharmaceutical compositions of the invention includes, but is not limited to, oral, intravenous infusion, subcutaneous injection, intramuscular, topical, depo injection, implantation, time-release mode, intracavitary, intranasal, inhalation, intralesional, intraocular, and controlled release. The pharmaceutical compositions of the invention also may be introduced parenterally, transmucosally (e.g., orally), nasally, rectally, intravaginally, sublingually, submucosally, or transdermally. Preferably, administration is parenteral, i.e., not through the alimentary canal but rather through some other route via, for example, intravenous, subcutaneous, intramuscular, intraperitoneal, intraorbital, intracapsular, intraspinal, intrasternal, intra-arterial, or intradermal administration. The skilled artisan can appreciate the specific advantages and disadvantages to be considered in choosing a mode of administration. Multiple modes of administration are encompassed by the invention. For example, an IGF-1 protein is administered by subcutaneous injection, whereas a combination therapeutic agent is administered by intravenous infusion. Moreover, administration of one or more species of IGF-1 proteins, with or without other therapeutic agents, may occur simultaneously (i.e., co-administration) or sequentially. For example, a IGF-1 protein is first administered to increase sensitivity to subsequent administration of a second therapeutic agent or therapy. In another embodiment, the periods of administration of one or more species of IGF-1 protein, with or without other therapeutic agents may overlap. For example, an IGF-1 protein is administered for 7 days, and a second therapeutic agent is introduced beginning on the fifth day of IGF-1 protein treatment, and treatment with the second therapeutic agent continues beyond the 7-day IGF-1 protein treatment. The IGF-1 can also be administered intermittently in a cyclical manner as described in U.S. Pat. No. 5,565,428.

In one embodiment, a pharmaceutical composition of the invention is delivered by a controlled-release or sustained release system. For example, the pharmaceutical composition may be administered using intravenous infusion, an implantable osmotic pump, a transdermal patch, liposomes, or other modes of administration. In one embodiment, a pump may be used (See, e.g., Langer, 1990, Science 249:1527-33; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, the compound can be delivered in a vesicle, in particular a liposome (See, e.g., Langer, Science 249:1527-33 (1990); Treat et al., 1989, in *Liposomes in the Therapy of Infectious Disease and Cancer*, Lopez-Berestein and Fidler (eds.), Liss, New York, pp. 353-65; Lopez-Berestein, ibid., pp. 317-27 International Patent Publication No. WO 91/04014; U.S. Pat. No. 4,704,355). In another embodiment, polymeric materials can be used (See, e.g., *Medical Applications of Controlled Release*, Langer and Wise (eds.), CRC Press: Boca Raton, Fla., 1974; *Controlled Drug Bioavailability, Drug Product Design and Performance*, Smolen and Ball (eds.), Wiley: New York (1984); Ranger and Peppas, 1953, J. Macromol. Sci. Rev. Macromol. Chem. 23:61; Levy et al., 1985, Science 228:190; During et al., 1989, Ann. Neurol. 25:351; Howard et al., 1989, J. Neurosurg. 71:105). Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (see Sidman et al., 1983, Biopolymers, 22:547-556), poly(2-hydroxyethyl methacrylate) (Langer et al., 1981, J. Biomed Mater Res, 15:167-277), and Langer, 1982, Chem Tech, 12:98-105), ethylene vinyl acetate (Langer et al., supra) or poly-D-(−)-3-hydroxybutyric acid (EP 133,988). Sustained-release IGF-1 compositions also include liposomally entrapped IGF-1. Liposomes containing IGF-1 are prepared by methods known per se: DE 3,218,121; Epstein et al., 1985, Proc Natl Acad Sci USA, 82:3688-3692; Hwang et al, 1980, Proc Natl Acad Sci USA, 77: 4030-4034; EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (from or about 200 to 800 Angstroms) unilamellar type in which the lipid content is greater than about 30 mol percent cholesterol, the selected proportion being adjusted for the optimal IGF-1 therapy.

In yet another embodiment, a controlled release system can be placed in proximity of the target. For example, a micropump may deliver controlled doses directly into the brain, thereby requiring only a fraction of the systemic dose (See, e.g., Goodson, 1984, in *Medical Applications of Controlled Release*, vol. 2, pp. 115-138). IGF-1 could be delivered directly into the peritoneal cavity to preferentially expose visceral fat to drug.

In one embodiment, it may be desirable to administer the pharmaceutical composition of the invention locally to the area in need of treatment; this may be achieved, for example, and not by way of limitation, by local infusion during surgery, topical application (e.g., in conjunction with a wound dressing after surgery), injection, by means of a catheter, by means of a suppository, or by means of an implant. An implant can be of a porous, non-porous, or gelatinous material, including membranes, such as sialastic membranes, or fibers.

IGF-1 can be administered before, during, and/or after the administration of one or more therapeutic agents. In yet another embodiment, there can be a period of overlap between the administration of IGF-1 and/or one or more therapeutic agents.

In a further embodiment, both IGF-1 and GH can be administered to the patient, each in effective amounts, or each in amounts that are sub-optimal but when combined are effective. Preferably such amounts are about 25 to 250 micrograms IGF-1/kg bodyweight/day and about 0.05 to 0.5 mg GH/kg bodyweight/week. Preferably, the administration of both IGF-1 and GH is by injection using, e.g., intravenous or subcutaneous means. More preferably, the administration is by subcutaneous injection for both IGF-1 and GH, most preferably daily bolus injections.

It is noted that practitioners devising doses of both IGF-1 and GH should take into account the known side effects of treatment with these hormones. For GH, the side effects include sodium retention and expansion of extracellular volume (Ikkos et al., Acta Endocrinol. (Copenhagen), 32: 341-361 (1959); Biglieri et al., J. Clin. Endocrinol. Metab., 21: 361-370 (1961)), as well as hyperinsulinemia and hyperglycemia. The major apparent side effect of IGF-1 is hypoglycemia (Guler et al., Proc. Natl. Acad. Sci. USA, 86: 2868-2872 (1989)). Indeed, the combination of IGF-1 and GH may lead to a reduction in the unwanted side effects of both agents (e.g., hypoglycemia for IGF-1 and hyperinsulinism for GH) and to a restoration of blood levels of GH, the secretion of which is suppressed by IGF-1.

For parenteral administration, in one embodiment, the IGF-1 and GH are formulated generally by mixing each at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the IGF-1 and GH each uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or non-ionic surfactants such as polysorbates, poloxamers, or PEG; and/or neutral salts, e.g., NaCl, KCl, $MgCl_2$, $CaCl_2$, etc.

The IGF-1 and GH are each typically formulated individually in such vehicles at a concentration of about 0.1 mg/mL to 100 mg/mL, preferably 1-10 mg/mL, at a pH of about 4.5 to 8. Full-length IGF-1 is preferably formulated at a pH about 5-6, and des(1-3)-IGF-1 is preferably formulated at a pH about 3.2 to 5. GH is preferably at a pH of 7.4-7.8. It will be understood that use of certain of the foregoing excipients, carriers, or stabilizers will result in the formation of IGF-1 or GH salts.

While GH can be formulated by any suitable method, the preferred formulations for GH are as follows. For met-GH (PROTROPIN™ brand), the pre-lyophilized bulk solution contains 2.0 mg/mL met-GH, 16.0 mg/mL mannitol, 0.14 mg/mL sodium phosphate, and 1.6 mg/mL sodium phosphate (monobasic monohydrate), pH 7.8. The 5-mg vial of met-GH contains 5 mg met-GH, 40 mg mannitol, and 1.7 mg total sodium phosphate (thy weight) (dibasic anhydrous), pH 7.8. The 10-mg vial contains 10 mg met-GH, 80 mg mannitol, and 3.4 mg total sodium phosphate (dry weight) (dibasic anhydrous), pH. 7.8.

For metless-GH (NUTROPIN™ brand), the pre-lyophilized bulk solution contains 2.0 mg/mL GH, 18.0 mg/mL mannitol, 0.68 mg/mL glycine, 0.45 mg/mL sodium phosphate, and 1.3 mg/mL sodium phosphate (monobasic monohydrate), pH 7.4. The 5-mg vial contains 5 mg GH, 45 mg mannitol, 1.7 mg glycine, and 1.7 mg total sodium phosphates (dry weight) (dibasic anhydrous), pH 7.4. The 10-mg vial contains 10 mg GH, 90 mg mannitol, 3.4 mg glycine, and 3.4 mg total sodium phosphates (dry weight) (dibasic anhydrous).

Alternatively, a liquid formulation of hGH (e.g. NUTROPIN AQ™ brand hGH) can be used, for example: 5.0±0.5 mg/mL rhGH; 8.8±0.9 mg/mL sodium chloride; 2.0±0.2 mg/mL Polysorbate 20; 2.5±0.3 mg/mL phenol; 2.68±0.03 mg/mL sodium citrate dihydrate; and 0.17±0.02 mg/mL citric acid anhydrous (total anhydrous sodium citrate/citric acid is 2.5 mg/mL, or 10 mM); pH 6.0±0.3. This formulation is suitably put in a 10-mg vial, which is a 2.0-mL fill of the above formulation in a 3-cc glass vial. Alternatively, a 10-mg (2.0 mL) cartridge containing the above formulation can be placed in an injection pen for injection of liquid GH to the patient.

In addition, the IGF-1 and GH, preferably the full-length IGF-1, may be formulated together in an appropriate carrier vehicle to form a pharmaceutical composition that preferably does not contain cells. In one embodiment, the buffer used for formulation will depend on whether the composition will be employed immediately upon mixing or stored for later use. If employed immediately after mixing, a mixture of full-length IGF-1 and GH can be formulated in mannitol, glycine, and phosphate, pH 7.4. If this mixture is to be stored, it is formulated in a buffer at a pH of about 6, such as citrate, with a surfactant that increases the solubility of the GH at this pH, such as 0.1% polysorbate 20 or poloxamer 188. The final preparation may be a stable liquid or lyophilized solid.

In one aspect, the combined composition comprises IGF-1 and GH in a weight ratio of IGF-1:GH of between about 1:1 and 100:1 (w/w), about 0.05-0.3 mM of an osmolyte, about 0.1-10 mg/mL of a stabilizer, about 1-5 mg/mL of a surfactant, and about 5-100 mM of a buffer at about pH 5-6. In some embodiments, the osmolyte is an inorganic salt and the surfactant is nonionic. Preferably, the inorganic salt is sodium chloride or potassium chloride, the stabilizer is phenol or benzyl alcohol, the surfactant is polysorbate or poloxamer, the buffer is sodium acetate or sodium citrate or both, and the amounts of IGF-1 and GH are about 2-20 mg/mL and about 0.2-10 mg/mL, respectively, with the weight ratio of IGF-1:GH being between about 1:1 and 50:1, or about 3:1 to 30:1, or about 3:1 to 25:1, or about 5:1 to 20:1. Alternatively, the amount of IGF-1 is about 5-10 mg/mL, the amount of GH is about 1-10 mg/mL, the weight ratio of IGF-1:GH is about 1:1 to 4:1, the amount of sodium chloride is about 5-7 mg/mL, the amount of phenol is about 0.1-3 mg/mL, the amount of benzyl alcohol is about 6-10 mg/mL, the surfactant is polysorbate in an amount of about 1-3 mg/mL, the amount of sodium acetate is about 2.5-4 mg/mL, and the amount of sodium citrate is about 0.1-1 mg/mL.

An "osmolyte" refers to an isotonic modifier or osmotic adjuster that lends osmolality to the buffered solution. Osmolality refers to the total osmotic activity contributed by ions and nonionized molecules to a solution. Examples include inorganic salts such as sodium chloride and potassium chloride, mannitol, polyethylene glycols (PEGs), polypropylene glycol, glycine, sucrose, glycerol, amino acids, and sugar alcohols such as mannitol known to the art that are generally regarded as safe (GRAS). The preferred osmolyte herein is sodium chloride or potassium chloride.

The "stabilizer" is any compound that functions to preserve the active ingredients in the formulation, i.e., GH and IGF-1, so that they do not degrade or otherwise become inactive over a reasonable period of time or develop pathogens or toxins that prevent their use. Examples of stabilizers include preservatives that prevent bacteria, viruses, and fungi from proliferating in the formulation, anti-oxidants, or other compounds that function in various ways to preserve the stability of the formulation.

For example, quaternary ammonium salts are useful stabilizers in which the molecular structure includes a central nitrogen atom joined to four organic (usually alkyl or aryl) groups and a negatively charged acid radical. These salts are useful as surface-active germicides for many pathogenic non-sporulating bacteria and fungi and as stabilizers. Examples include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of stabilizers include aromatic alcohols such as phenol and benzyl alcohol, alkyl parabens such as methyl or propyl paraben, and m-cresol. The most preferred stabilizer herein is phenol or benzyl alcohol.

The stabilizer is included in a stable liquid form of the GH and IGF-1 formulation, but not in a lyophilized form of the formulation. In the latter case, the stabilizer is present in the bacteriostatic water for injection (BWFI) used for reconstitution. The surfactant is also optionally present in the reconstitution diluent.

The "inorganic salt" is a salt that does not have a hydrocarbon-based cation or anion. Examples include sodium chloride, ammonium chloride, potassium chloride, magnesium chloride, calcium chloride, sodium phosphate, calcium phosphate, magnesium phosphate, potassium phosphate, ammonium phosphate, sodium sulfate, ammonium sulfate, potassium sulfate, magnesium sulfate, calcium sulfate, etc. Preferably, the cation is sodium and the anion is chloride or sulfate, and the most preferred inorganic salt is potassium chloride or sodium chloride.

The "surfactant" acts to increase the solubility of the IGF-1 and GH at a pH about 4-7. It is preferably a nonionic surfactant such as a polysorbate, e.g., polysorbates 20, 60, or 80, a poloxamer, e.g., poloxamer 184 or 188, or any others known to the art that are GRAS. More preferably, the surfactant is a polysorbate or poloxamer, more preferably a polysorbate, and most preferably polysorbate 20.

The "buffer" may be any suitable buffer that is GRAS and confers a pH of 5-6 on the GH+IGF-1 formulation and a pH of about 5-5.5 on the IGF-1 formulation. Examples include acetic acid salt buffer, which is any salt of acetic acid, including sodium acetate and potassium acetate, succinate buffer, phosphate buffer, citrate buffer, or any others known to the art to have the desired effect. The most preferred buffer is sodium acetate, optionally in combination with sodium citrate.

Suitable compositions of IGF-1 and GH before they are mixed together include the following: about 5-20 mg/ml of IGF-1, and about 5-20 mg/ml of GH.

Suitable compositions containing both IGF-1 and GH include the following: about 5-10 mg/ml of IGF-1, about 0.5-5 mg/ml of GH at a weight ratio of IGF-1:GH of about 1:1 to 20:1, about 5-7 mg/ml of sodium chloride, about 0.1-3 mg/ml of phenol and/or about 6-10 mg/ml of benzyl alcohol, about 1-3 mg/ml of polysorbate, about 2.5-4 mg/ml of sodium acetate, and about 0.1-1 mg/ml of sodium citrate, pH about 5.4.

The final formulation, if a liquid, is preferably stored at a temperature of about 2°-8° C. for up to about four weeks. Alternatively, the formulation can be lyophilized and provided as a powder for reconstitution with water for injection that is stored as described for the liquid formulation.

IGF-1 and GH to be used for therapeutic administration are preferably sterile. Sterility is readily accomplished by filtration through sterile filtration membranes (e.g., 0.2 micron membranes). Therapeutic IGF-1 and GH compositions generally are placed into a container having a sterile access port, for example, an intravenous solution bag or vial having a stopper pierceable by a hypodermic injection needle.

The IGF-1 and GH ordinarily will be stored in unit or multi-dose containers, for example, sealed ampoules or vials, as an aqueous solution, or as a lyophilized formulation for reconstitution. As an example of a lyophilized formulation, 10-mL vials are filled with 5 mL of sterile-filtered it (w/v) aqueous IGF-1 and GH solutions, and the resulting mixture is lyophilized. The infusion solution is prepared by reconstituting the lyophilized IGF-1 and GH using bacteriostatic Water-for-Injection.

The GH+IGF-1 formulation is preferably injected. If, however, the object is to affect the body composition of the patient or to increase not only whole body weight but also selected organs such as the thymus and kidney, for example, in patients that are immunodeficient (such as AIDS patients) or in patients with kidney disorders (such as ischemic or nephrotoxic dysfunction or chronic or acute renal insufficiency), the GH+IGF-1 formulation is preferably infused to the patient.

The formulation containing both the IGF-1 and GH can be made by many different methods. One method comprises mixing an IGF-1-containing composition (having osmolyte, stabilizer, and buffer as described below) with a buffered solution comprising GH at a pH about 6 in a dose (mg) ratio of from about 1:1 to 20:1 IGF-1:GH up to a dose no greater than about 5 mg/ml of GH. Preferably, this buffered solution contains about 0.5-5 mg/ml of GH in about 5-15 mg/ml of an inorganic salt, about 1-5 mg/ml of a stabilizer, about 1-5 mg/ml of a surfactant, and sodium citrate buffer at pH about 6. More preferably, the liquid GH formulation contains, about 1-5 mg/ml GH, about 8-9 mg/ml sodium chloride, about 1-3 mg/ml phenol, about 1-3 mg/ml polysorbate 20, and about 10 mM sodium citrate, pH about 6.

The IGF-1-containing solution useful for administering IGF-1 separately from GH and for admixing with the GH solution as described above is as follows: about 2-20 mg/ml of IGF-1, about 2-50 mg/ml of an osmolyte, about 1-15 mg/ml of at least one stabilizer, and a buffer (preferably an acetic acid salt buffer, and most preferably sodium acetate) in an amount such that the composition has a pH of about 5-5.5. The osmolyte, stabilizer, and buffer, and the preferred compounds within these categories are defined above. Optionally, the formulation may also contain a surfactant selected from the types described above, preferably in an amount of about 1-5 mg/ml, more preferably about 1-3 mg/ml.

In a preferred embodiment, the osmolyte is an inorganic salt at a concentration of about 2-10 mg/ml or a sugar alcohol at a concentration of about 40-50 mg/ml, the stabilizer is benzyl alcohol, phenol, or both, and the buffered solution is an acetic acid salt buffered solution. More preferably, the osmolyte is an inorganic salt, most preferably sodium chloride.

In an even more preferred formulation, the amount of IGF-1 is about 8-12 mg/ml, the amount of sodium chloride is about 5-6 mg/ml, the stabilizers are benzyl alcohol in an amount of about 8-10 mg/ml and/or phenol in an amount of about 2-3 mg/ml, and the buffer is about 50 mM sodium acetate so that the pH is about 5.4. Optionally, the formulation contains polysorbate as a surfactant in an amount of about 1-3 mg/ml. A 50-mM acetate concentration in the starting IGF-1 solution before mixing with GH ensures that the final pH will not vary significantly from 5.4 in the final IGF-1/GH mixture to maintain good solubility of both proteins over a wide mixing ratio range. However, a broader pH range in terms of stability of both proteins is from about 5 to about 6.

It will be understood that IGF-1 and GH combination therapies of the invention may be administered to the patient in the form of a single daily administration of an IGF-1 and GH co-formulated drug product, in the form of a single daily administration of an IGF-1 drug product and a separate, but coincident or substantially contemporaneous, single daily administration of a GH drug product, or in the form of a single daily administration of a co-mixture of an IGF-1 drug product and a separate GH drug product, where the IGF-1 drug product and the GH drug product are admixed prior to administration to the patient.

In connection with embodiments that employ admixture of separate IGF-1 and GH drug products prior to administration, the invention contemplates the use of any combination of drug product configurations and drug delivery systems that will achieve admixture of the separate IGF-1 and GH drug products at a time prior to administration. In some embodiments, separate liquid formulations of IGF-1 and GH are contained in separate vials, and a single syringe is used to draw into the syringe the desired doses of IGF-1 and GH from the respective vials, thereby admixing the IGF-1 and GH liquid formulations shortly before administration to the patient via a single injection.

In other embodiments, separate lyophilized formulations of IGF-1 and GH are reconstituted in separate vials, and a single syringe is used to draw into the syringe the desired doses of IGF-1 and GH from the respective vials, thereby admixing the IGF-1 and GH liquid formulations shortly before administration to the patient via a single injection.

In other embodiments, a liquid formulation of IGF-1 is used to reconstitute a lyophilized formulation of GH, thereby creating an admixture of IGF-1 and GH, and a single syringe is used to draw from the admixture the desired doses of IGF-1 and GH shortly before administration to the patient via a single injection.

In other embodiments, a liquid formulation of GH is used to reconstitute a lyophilized formulation of IGF-1, thereby creating an admixture of IGF-1 and GH, and a single syringe is used to draw from the admixture the desired doses of IGF-1 and GH shortly before administration to the patient via a single injection.

In other embodiments, a cartridge pre-filled with the desired dose of IGF-1 in a liquid formulation and a second cartridge pre-filled with the desired dose of GH in a liquid formulation are loaded into a double-barreled syringe, and a single plunge of the syringe's plunger is used to expel the liquid in each cartridge into (i) a common channel or chamber leading to a single aperture in positioned in the body of a patient or (ii) a common aperture positioned in the body of the patient, and effect the admixture of the liquids upon entry into the common channel, chamber or aperture shortly before administration to the patient via a single injection.

In other embodiments, a double-chambered syringe is pre-filled with the desired dose of IGF-1 in a liquid formulation in one chamber and is pre-filled with the desired dose of GH in a liquid formulation in the other chamber, and a single plunge of the syringe's plunger is used to expel the liquid in each chamber into (i) a common channel or chamber leading to a single aperture in positioned in the body of a patient or (ii) a common aperture positioned in the body of the patient, and effect the admixture of the liquids upon entry into the common channel, chamber or aperture shortly before administration to the patient via a single injection.

The present invention may be better understood by reference to the following non-limiting Examples, which are provided only as exemplary of the invention. The following examples are presented to more fully illustrate the preferred embodiments of the invention. They should in no way be construed, however, as limiting the broader scope of the invention.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

A Pharmacokinetic Study to Assess the Parameters Controlling the Clearance of IGF-1 and the Dosing Requirements for Recombinant Human IGF-1 (rhIGF-1) in Patients, Especially Those with IGF-1 Deficiency (IGFD)

In children with IGFD (defined as short stature and low blood IGF-1 concentrations) physiologic replacement therapy with rhIGF-1 should correct IGF-1 concentrations to age- and gender-appropriate levels. IGFD can be caused by a lack of GH or a lack of GH action. Across the spectrum of IGFD, there is a direct correlation between serum IGF-1 and IGFBP-3 concentrations. IGFBP-3 is also inversely related to rhIGF-1 clearance (as discussed in detail below; data presented in FIG. 5A). Thus, rhIGF-1 dosing may need to be adjusted to prevailing IGFBP-3 levels. A single-dose rhIGF-1 PK study was conducted in subjects who had a wide range of IGF-1 and IGFBP-3 concentrations.

The objectives were to determine the pharmacokinetic (PK) parameters of a subcutaneous injection of recombinant human IGF-1 (rhIGF-1); to determine the dependence of the PK parameters on serum IGFBP-3; and to determine the safety of a single subcutaneous (sc) dose of rhIGF-1.

Methods: Twelve subjects with an extreme form of IGFD (Laron syndrome; LS, with severe IGFD, IGF-1 SDS <−3), 12 with moderate IGFD (IGF-1 SDS <−2, and normal GH secretion), and 12 normal subjects (IGF-1 SDS >−2) were randomized to receive 15, 30, 60 or 120 µg/kg rhIGF-1 as a single SC dose. Key inclusion criteria included: body mass of ≧10 kg; and age <5 years. PK parameters for each subject were estimated with WinNonlin (Pharsight Corp., Mountain View, Calif.). A model was developed that accounted for endogenous IGF-1 production (or generation) and the effect of IGFBP-3 on serum IGF-1 retention. Model simulations were used with individual subject PK parameters to estimate IGF-1 concentrations after two weeks of BID dosing. IGF-1 concentrations were transformed to IGF-1 SD scores using the SDS calculator, described in Example 4, specific for the IGF-1 assay.

Cohorts, doses, and numbers of subjects are shown in Table 1.

TABLE 1

| Cohort | 15 µg/kg | 30 µg/kg | 60 µg/kg | 120 µg/kg |
|---|---|---|---|---|
| Severe IGFD IGF-1 SDS <−3 | 3 | 3 | 3 | 3 |
| IGFD IGF-1 SDS −3 to −2 | 3 | 3 | 3 | 3 |
| Normal IGF-1 IGF-1SDS −2 to +2 | 3 | 3 | 3 | 3 |

Figure 6:
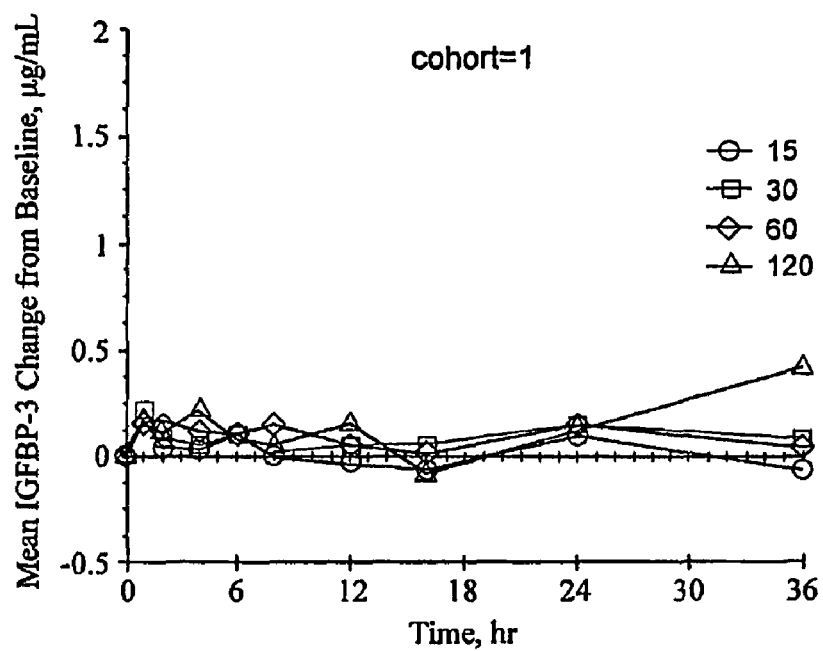
FIG. 6 is a graph depicting the change in mean endogenous IGFBP-3 concentration in blood over time (36 hours) in Severe Primary IGF-1 Deficient patients in response to a single subcutaneous injection of IGF-1 given at time zero for dosing levels of 15, 30, 60 and 120 μg IGF-1/kg body weight (which dosing levels are represented by circles, squares, diamonds and triangles, respectively, in the figure).

Population PK Model Development. The one-compartment model with first-order SC absorption and elimination was used to characterize pharmacokinetics of IGF-1, as shown in FIG. 6. A zero-order input rate ($K_{in}$) was used to characterize the endogenous formation rate of IGF-1.

PK parameters, absorption rate constant ($K_a$), IGF-1 generation rate ($K_{in}$), volume of distribution ($V_d$) and clearance (CL) are modeled as follows:

$$K_a = \theta_1 \cdot \exp(BSV_1)$$

$$K_{in} = \theta_2 \cdot \exp(BSV_2)$$

$$CL = \theta_3 \cdot \exp(BSV_3)$$

$$V_d = \theta_4 \cdot \exp(BSV_4)$$

$$K_{el} = CL/V_d$$

where $\theta_1$ are the fixed-effect parameters and $BSV_1$ are between-subject random-effect parameters estimated by NONMEM. Exponential error models were employed for the between subject variability of $K_a$, $K_{1n}$, CL, and $V_d$.

Results: The calculated PK parameter values by cohort and dose group are shown in Tables 2 and 3. IGF-1 AUC was directly related to dose (r=0.53, p=0.001) and IGFBP-3 level (r=0.44, p=0.008), where 'r' is a partial correlation coefficient reflecting adjustment for cohort. The log of IGFBP-3 was inversely related to both IGF-1 clearance (r=−0.91) and Kel (r=−0.92), both p<0.0001. Compared to severe IGFD subjects, IGFD subjects had higher AUC and lower Kel suggesting lower rhIGF-1 doses are possible as replacement therapy. Values for Kel are low, so simulations of two weeks of BID dosing predict an accumulation of IGF 1.

TABLE 2

Calculated AUCs by Cohort and Dose

| Cohort | 15 µg/kg | | | 30 µg/kg | | | 60 µg/kg | | | 120 µg/kg | | |
|---|---|---|---|---|---|---|---|---|---|---|---|---|
| | N | AUC | SD | N | AUC | SD | N | AUC | SD | N | AUC | SD |
| Severe IGFD IGF-1 SDS <−3 | 3 | 717 | 250 | 3 | 944 | 461 | 3 | 2082 | 1111 | 3 | 2932 | 1475 |
| IGFD IGF-1 SDS −3 to −2 | 3 | 4404 | 3033 | 3 | 5132 | 3544 | 3 | 4338 | 2634 | 3 | 9049 | 4567 |
| Normal IGF-1 IGF-1 SDS −2 to +2 | 3 | 4079 | 648 | 3 | 7160 | 2441 | 3 | 10256 | 4550 | 3 | 9549 | 2740 |

TABLE 3

PK Parameter Values

| Cohort | Vd (L/kg) | Clearance (mL/min/kg) | $K_{el}$ ($hr^{-1}$) | IGFBP-3 (µg/mL) | $K_{in}$ (µg/kg/hr) |
|---|---|---|---|---|---|
| Severe IGFD IGF-1 SDS <−3 | 0.257 | 0.700 | 0.173 | 0.62 | 0.94 |
| IGFD IGF-1 SDS −3 to −2 | 0.258 | 0.217 | 0.052 | 2.71 | 1.80 |
| Normal IGF-1 IGF-1 SDS −2 to +2 | 0.259 | 0.183 | 0.043 | 2.87 | 2.80 |

Figure 1:
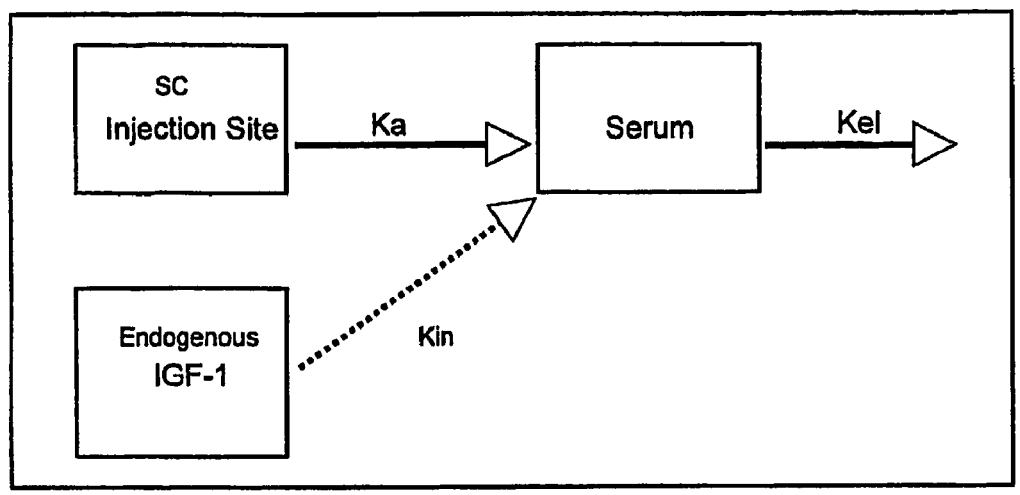
FIG. 1 is a schematic representation of an IGF-1 pharmacokinetic model indicating that when a natural molecule is administered the observed pharmacokinetics must also take account of the natural endogenous molecule (herein IGF-1). The letter (k) indicates kinetics of (a) absorption, (in) production and (el) elimination.
Figure 2:
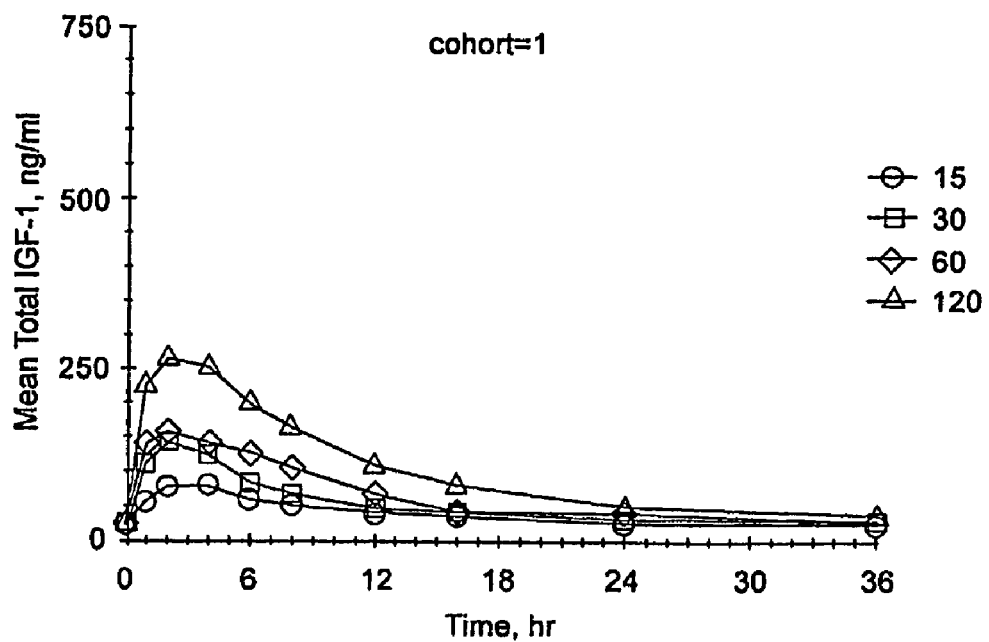
FIG. 2 is a graph depicting the pharmacokinetics of mean total IGF-1 concentration in serum over time (36 hours) in Severe Primary IGF-1 Deficient patients following a single subcutaneous injection of IGF-1 at time zero for dosing levels of 15, 30, 60 and 120 μg IGF-1/kg body weight (which dosing levels are represented by circles, squares, diamonds and triangles, respectively, in the figure).
Figure 3:
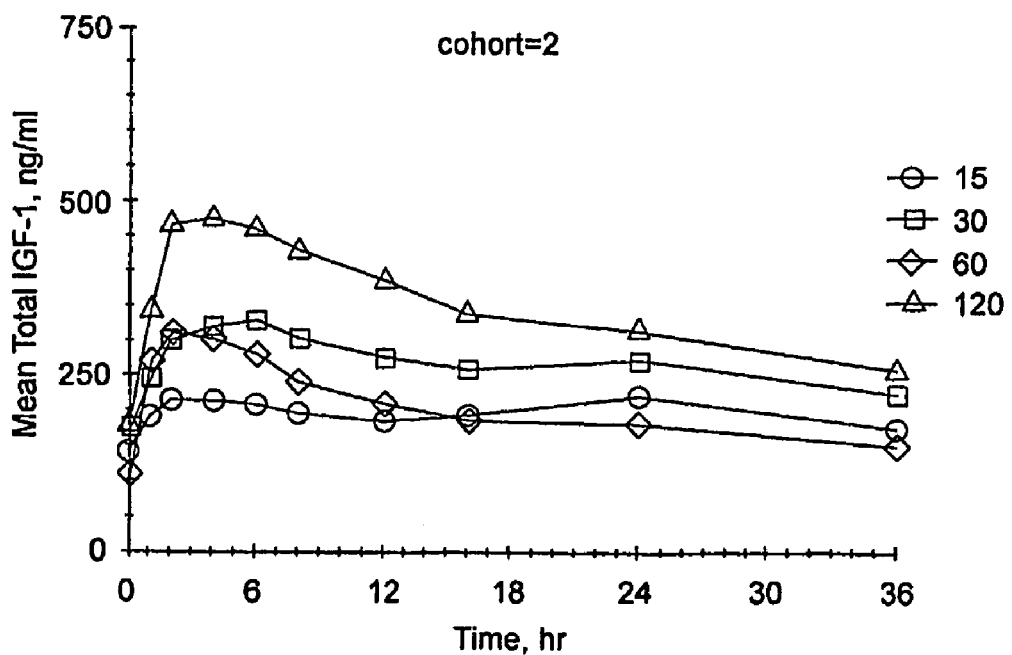
FIG. 3 is a graph depicting the pharmacokinetics of mean total IGF-1 concentration in serum over time (36 hours) in Moderate Primary IGF-1 Deficient patients following a single subcutaneous injection of IGF-1 at time zero for dosing levels of 15, 30, 60 and 120 μg IGF-1/kg body weight (which dosing levels are represented by circles, squares, diamonds and triangles, respectively, in the figure).
Figure 4:
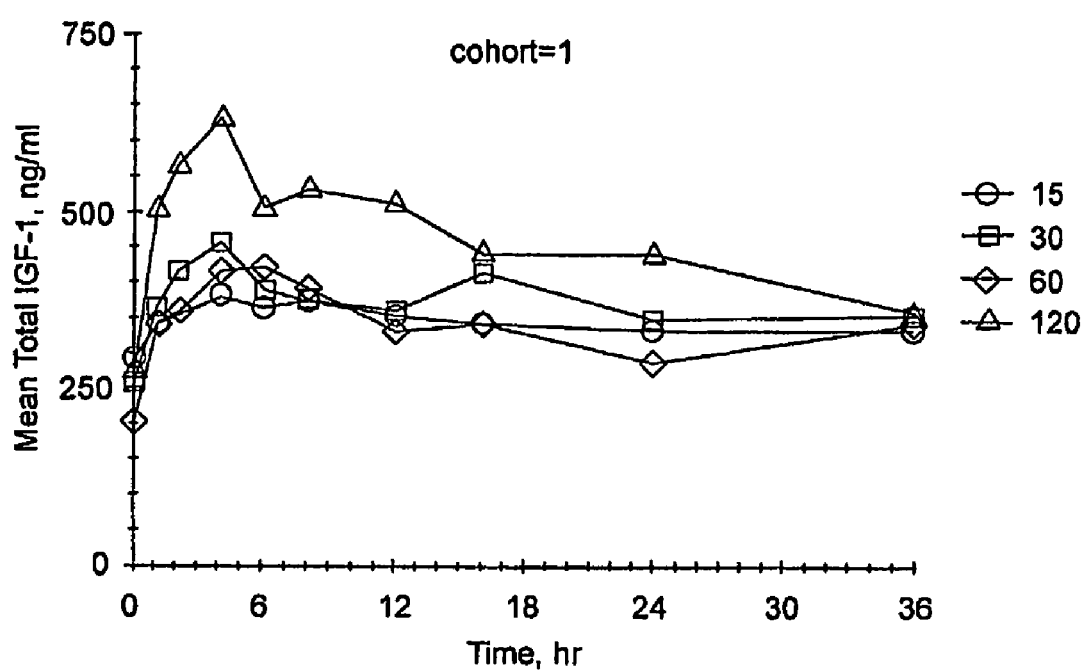
FIG. 4 is a graph depicting the pharmacokinetics of mean total IGF-1 concentration in blood over time (36 hours) in patients with normal IGF-1 levels following a single subcutaneous injection of IGF-1 at time zero for dosing levels of 15, 30, 60 and 120 μg IGF-1/kg body weight (which dosing levels are represented by circles, squares, diamonds and triangles, respectively, in the figure).
Figure 10:
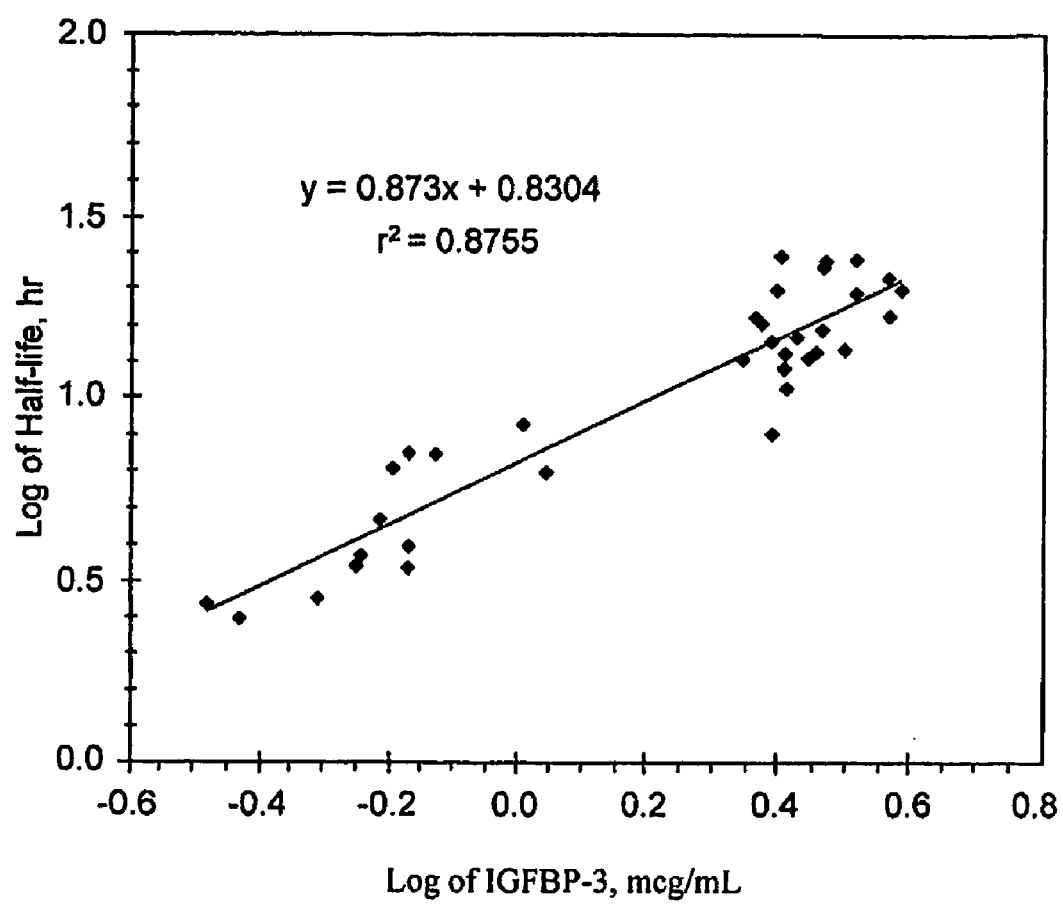
FIG. 10 is a graph depicting the relationship between IGFBP-3 blood concentration and IGF-1 blood concentration half-life (shown on a log-log scale). The solid line represents the model-predicted function.
Figure 11:
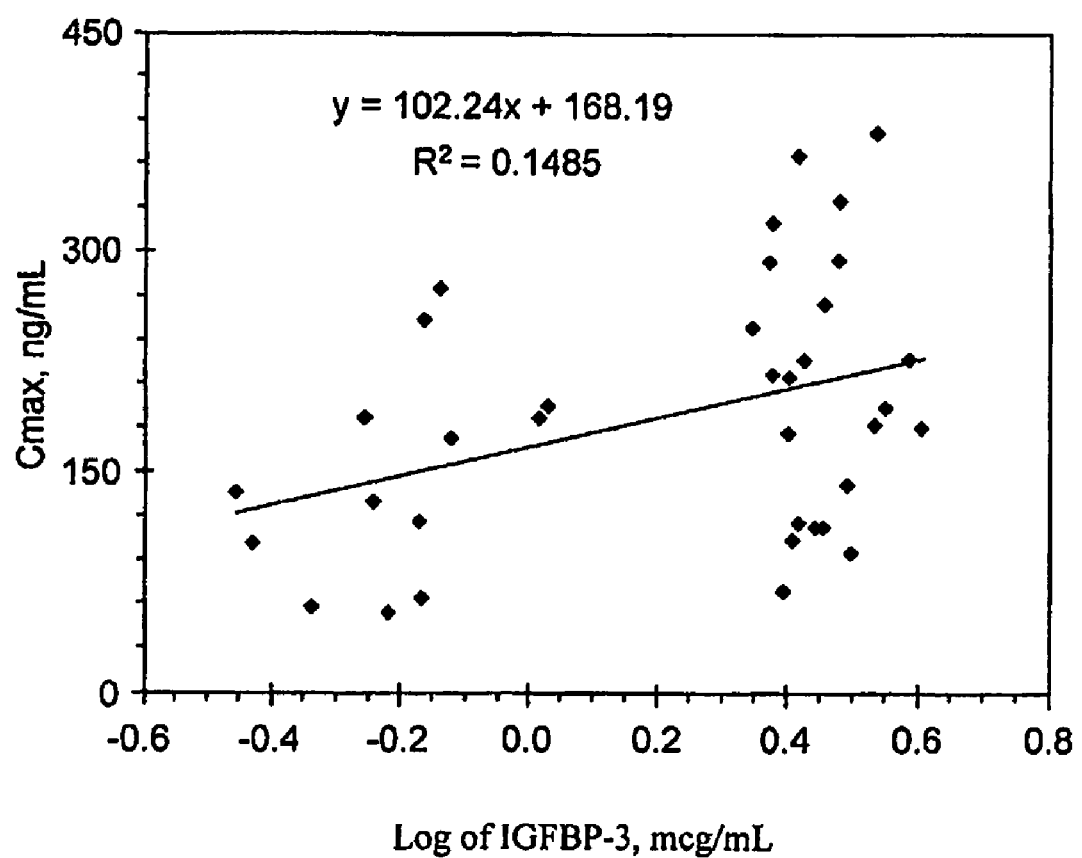
FIG. 11 is a graph depicting the relationship between IGFBP-3 blood concentration (IGFBP-3 concentration shown in log scale) and IGF-1 peak blood concentration (Cmax). The solid line represents the model-predicted function.

The pharmacokinetics of IGF-1 in (a) patients with IGF-1 deficiency (b) patients with moderate IGF-1 deficiency and (c) normal patients are depicted in FIGS. 2, 3 and 4, respectively. It was found that the pharmacokinetics of IGF-1 were very different in these patient groups. It was also found that the pharmacokinetics of IGF-1 depends on the blood concentrations of IGFBP-3 (see FIG. 10).

In patients with severe IGF-1 deficiency, the clearance of IGF-1 was found to be very rapid (see FIG. 2). In such patients with IGFD, there is little or no GH or GH action. From these data, it was determined that patients with severe GH deficiency or severe IGF-1 deficiency need prolonged exposure to IGF-1 each day, which can be effected by twice daily administration of IGF-1.

However, in patients who are not profoundly GH deficient or GH resistant, IGFBP-3 levels are closer to normal and the clearance of IGF-1 is closer to that of normal patients. In these patients, the half-life of IGF-1 is longer than in the severe patients. Therefore, the less severe patients experience a longer exposure to IGF-1 after a single injection of IGF-1, as shown in FIG. 3.

Figure 5:
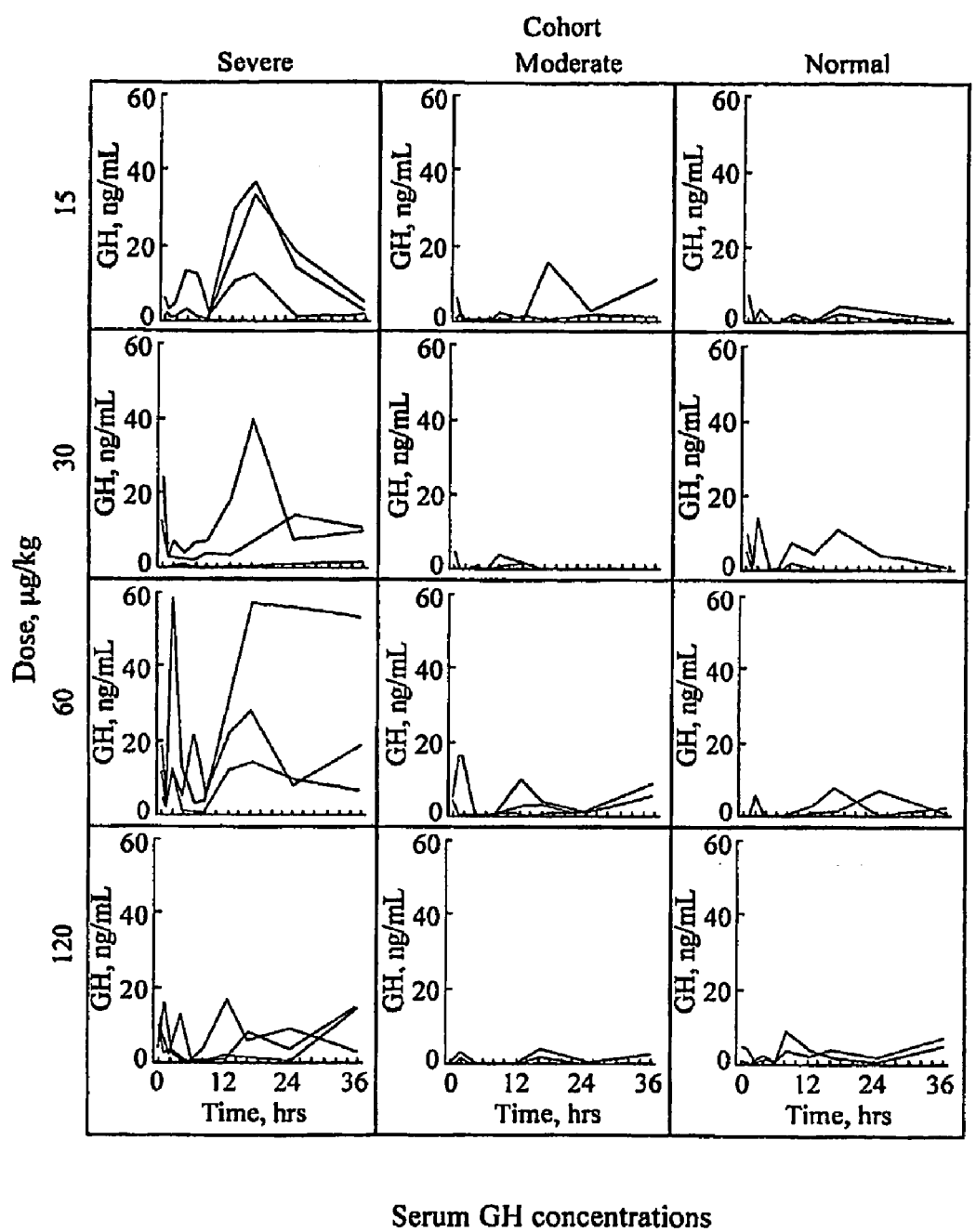
FIG. 5 is a collection of graphs depicting the change in mean endogenous GH concentration in blood over time in Severe Primary IGF-1 Deficient patients (left panels), Moderate Primary IGF-1 Deficient patients (middle panels), and normal patient cohorts (right panels) in response to a single subcutaneous injection of IGF-1 for dosing levels of 15 (top panels), 30 ($2^{nd}$ from top panels), 60 ($3^{rd}$ from top panels) and 120 (bottom panels) μg IGF-1/kg body weight. The graphs show that the concentrations of GH are suppressed for several hours following an injection of IGF-1, followed by a large rebound release of GH several hours following the IGF-1 administration. This is best seen in the patients with extreme IGFD but enhanced GH secretion.

The effects of IGF-1 administration on endogenous GH levels in blood of treated patients are depicted in FIG. 5. As shown in FIG. 5, the blood concentrations of GH are suppressed for several hours following IGF-1 administration, followed by a large "rebound" release of GH several hours after IGF-1 administration. This effect was most pronounced in patients with extreme IGFD but enhanced GH secretion. From these data, it was determined that once daily dosing of IGF-1 would allow for the recovery of endogenous GH secretion between injections.

Figure 7:
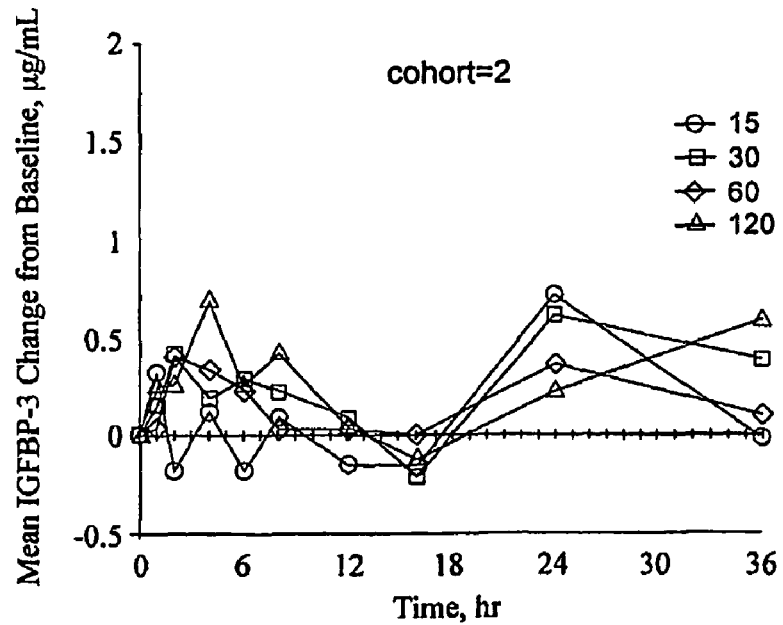
FIG. 7 is a graph depicting the change in mean endogenous IGFBP-3 concentration in blood over time (36 hours) in Moderate Primary IGF-1 Deficient patients in response to a single subcutaneous injection of IGF-1 given at time zero for dosing levels of 15, 30, 60 and 120 μg IGF-1/kg body weight (which dosing levels are represented by circles, squares, diamonds and triangles, respectively, in the figure).
Figure 8:
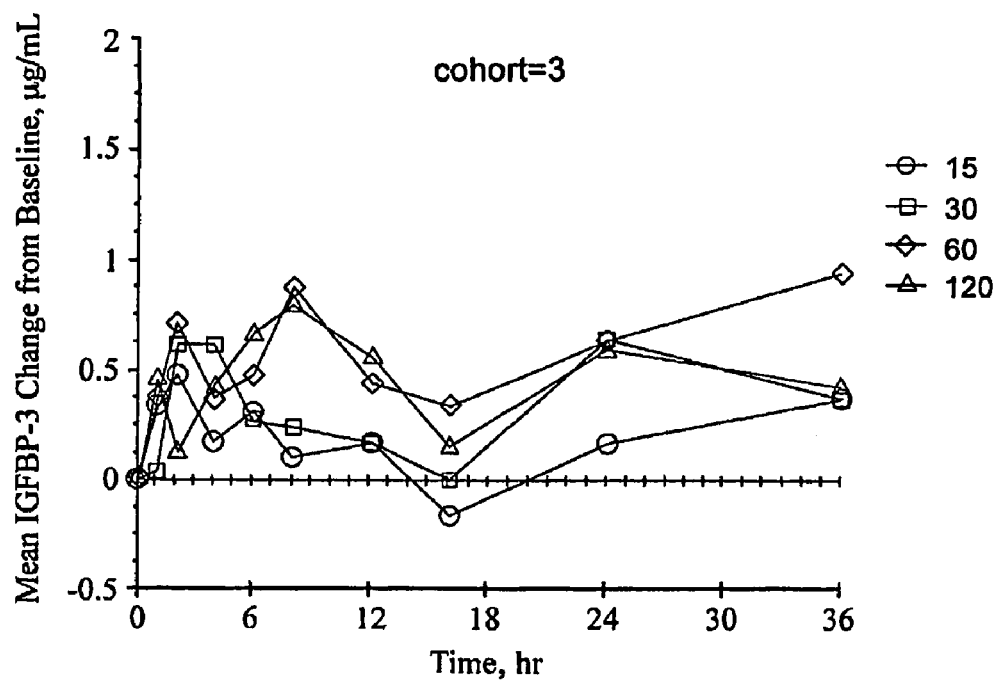
FIG. 8 is a graph depicting the change in mean endogenous IGFBP-3 concentration in blood over time (36 hours) in patients with normal IGF-1 levels in response to a single subcutaneous injection of IGF-1 at time zero for dosing levels of 15, 30, 60 and 120 μg IGF-1/kg body weight (which dosing levels are represented by circles, squares, diamonds and triangles, respectively, in the figure).
Figure 9:
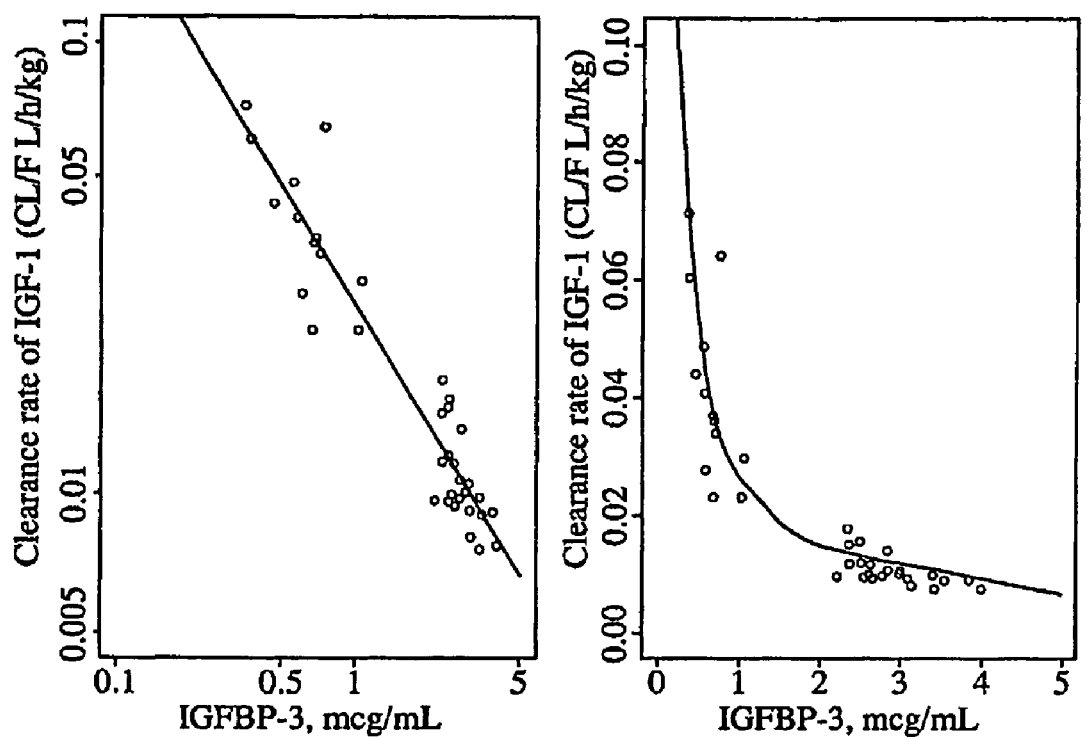
FIG. 9 is pair of graphs depicting the relationship between IGF-1 clearance and IGFBP-3 concentration in blood showing on the right this relationship plotted on an arithmetic basis, and on the left on a logarithmic basis whereby the relationship is linearized.

The effects of IGF-1 administration on endogenous IGFBP-3 levels in blood of (a) treated patients with severe IGF-1 deficiency (b) treated patients with moderate IGF-1 deficiency and (c) treated normal patients are depicted in FIGS. 6, 7 and 8, respectively. Upon administration of IGF-1, there was an immediate rise in IGFBP-3 levels in the blood. Twelve to fifteen hours after IGF-1 administration, the IGFBP-3 blood levels fell back to pretreatment baseline levels, or below. The IGFBP-3 blood levels then "rebounded" to above pretreatment baseline levels in all groups by 24 to 36 hours post-administration of IGF-1. From these data, it was determined that IGFBP-3 blood levels are a good marker of organic GH activity in a patient.

Conclusions: Once daily dosing of IGF-1 allows for the maintenance of organic GH activity in patients having growth disorders not characterized by severe GH deficiency or severe GH resistance. Thus, once daily dosing of IGF-1 is believed to be the optimum therapy for promotion of growth in patients not affected by severe GH deficiency or severe GH resistance, such as moderate primary IGFD patients and ISS patients. In addition, IGFBP-3 blood levels can aid in the selection of children who may be candidates for once-daily dosing with rhIGF-1.

Example 2

Short-Term Treatment with Recombinant Human Insulin-Like Growth Factor-1 (rhIGF-1): an Open-Label, Randomized Pharmacokinetic and Pharmacodynamic Study in Subjects with IGF-1 Deficiency The primary objective of the study was to determine the standard deviation scores (SDS) and pharmacokinetic parameters of serum IGF-1 and IGFBP-3 following three weeks of daily dosing with subcutaneous (SC) injections of rhIGF-1 in subjects with IGF-1 deficiency.

Methods: This was an open-label, randomized, parallel dose study to assess the steady-state PK/PD of IGF-1 at three SC dosing regimens following a short-term (e.g. 3 week) rhIGF-1 dosing: 40 mg/kg BID, 80 mg/kg BID or 80 mg/kg QD, on 18 IGFD subjects (i.e. IGF-1 SDS <−2.0).

The total IGF-1 SDS and IGFBP-3 over a 24-hour period at steady state were determined. The pharmacokinetic parameters of total IGF-1 were determined by a non-compartmental method based on the baseline corrected total IGF-1 concentrations at steady state: CL/F, V/F, AUC, $C_{max}$, $T_{max}$, $C_{min}$, half-life and fluctuation index.

Results: A total of 18 subjects completed the multiple-dose PK/PD study. The demographic characteristics of subjects are summarized in Tables 4 and 5 by cohort and by dose group, respectively. Total IGF-1 pharmacokinetic parameters based on the baseline corrected total IGF-1 concentrations at steady state are presented in Table 6 by dose group. In addition, Total IGF-1 SDS and concentration, and IGFBP-3 over the 24-hour period at steady state are summarized by dose groups in Tables 5-10 below and in FIGS. 17-25. The IGFBP-3 at baseline and the average over the 24-hour period at steady state were compared in FIG. 26.

The area under the curve (or AUC) of IGF-1 exposure was similar for 40 micrograms/kg given twice daily to that for 80 micrograms/kg given once daily (Tables 6 and 10). There was also a greater percent fluctuation in IGF-1 levels in the group treated once a day (136.9%) compared to the groups treated twice daily (68.7 and 77.4%).

Conclusion: IGF-1 exposure (measured as AUC) could be maintained with once daily dosing despite much greater fluctuations in IGF-1 levels. These greater fluctuations would allow GH secretion to rebound between IGF-1 injections.

TABLE 4

Demographic Summary of IGFD Patients by Cohort

| Parameter [a] | Cohort 1<br>IGFBP-3 < median<br>(N = 6M/3F) | Cohort 2<br>IGFBP-3 > median<br>(N = 7M/2F) |
|---|---|---|
| Age, year | 14.7 | 14.2 |
| (Range) | (12.6-18.7) | (11.2-18.8) |
| Height, cm | 148 | 147 |
| (Range) | (141-162) | (131-166) |
| Weight, kg | 40.9 | 50.1 |
| (Range) | (32.0-57.5) | (25.2-72.0) |
| IGFBP-3, µg/mL | 2.24 | 2.97 |
| (Range) | (1.70-2.80) | (2.40-3.50) |
| IGF-1, ng/mL | 146 | 125 |
| (Range) | (99-212) | (93-199) |

TABLE 5

Demographic Summary of IGFD Patients by Dose Group

| Parameter [a] | 40 µg/kg BID<br>(N = 3M/3F) | 80 µg/kg BID<br>(N = 6M) | 80 µg/kg QD<br>(N = 4M/2F) |
|---|---|---|---|
| Age, year | 16.0 | 14.0 | 13.3 |
| (Range) | (13.8-18.8) | (12.9-16.2) | (11.2-18.7) |
| Height, cm | 153 | 148 | 142 |
| (Range) | (141-164) | (141-166) | (131-162) |
| Weight, kg | 43.5 | 42.3 | 40.8 |
| (Range) | (33.0-50.5) | (32.0-83.5) | (28.0-57.5) |
| IGFBP-3, µg/mL | 2.85 | 2.50 | 2.47 |
| (Range) | (2.3-3.4) | (1.7-3.5) | (2.0-3.2) |
| IGF-1, ng/mL | 147.5 | 133 | 127 |
| (Range) | (110-212) | (99-199) | (93-201) |

TABLE 6

Geometric Mean and % CV of Total IGF-1 Steady-state Pharmacokinetic Parameters by Dose Group

| Parameter | 40 µg/kg BID | | 80 µg/kg BID | | 80 µg/kg QD | | All | |
|---|---|---|---|---|---|---|---|---|
| | Mean | % CV | Mean | % CV | Mean | % CV | Mean | % CV |
| $C_{min}$ (ng/mL) | 176 | 65.8 | 225 | 48.5 | 85 | 47.8 | 150 | 80.0 |
| $C_{max}$ (ng/mL) | 373 | 35.1 | 528 | 20.3 | 377 | 22.6 | 420 | 31.8 |
| $T_{max}$ (hr) | 1.99 | 25.9 | 2.30 | 40.0 | 3.24 | 31.6 | 2.46 | 40.3 |
| CL/F (L/hr/kg) | 0.0120 | 36.2 | 0.0178 | 25.1 | 0.0158 | 21.7 | 0.0150 | 33.3 |
| V/F (L/kg) | 0.181 | 66.2 | 0.268 | 39.4 | 0.209 | 27.9 | 0.216 | 48.1 |
| Half-life (hr) | 10.41 | 85.7 | 10.43 | 31.1 | 9.15 | 39.3 | 9.98 | 51.1 |

TABLE 6-continued

Geometric Mean and % CV of Total IGF-1 Steady-state Pharmacokinetic Parameters by Dose Group

| Parameter | 40 µg/kg BID | | 80 µg/kg BID | | 80 µg/kg QD | | All | |
|---|---|---|---|---|---|---|---|---|
| | Mean | % CV | Mean | % CV | Mean | % CV | Mean | % CV |
| $AUC_{ss}$ (hr * ng/mL) [a] | 6647 | 36.2 | 8992 | 25.1 | 5055 | 21.7 | 6710 | 39.9 |
| Fluctuation (%) [b] | 68.7 | 27.8 | 77.4 | 38.6 | 136.9 | 11.6 | 89.9 | 47.0 |

[a] $AUC_{ss}$ = Steady-state AUC over a 24-hour period
[b] Fluctuation = $(C_{max} - C_{min})/(AUCss/24) * 100\%$

TABLE 7

Mean and SD of Total IGF-1 at Steady State by Dose Group

| Time (hr) | 40 µg/kg BID | | 80 µg/kg BID | | 80 µg/kg QD | |
|---|---|---|---|---|---|---|
| | Mean | SD | Mean | SD | Mean | SD |
| −99 [a] | 163 | 42 | 128 | 32 | 145 | 46 |
| −1 | 392 | 80 | 365 | 96 | 232 | 66 |
| 0 | 382 | 95 | 348 | 121 | 246 | 69 |
| 0.25 | 413 | 90 | 442 | 119 | 270 | 55 |
| 0.5 | 407 | 97 | 484 | 137 | 307 | 61 |
| 0.75 | 435 | 130 | 505 | 118 | 339 | 59 |
| 1 | 450 | 134 | 552 | 90 | 379 | 55 |
| 1.25 | 483 | 137 | 569 | 109 | 400 | 58 |
| 1.5 | 483 | 121 | 608 | 97 | 441 | 37 |
| 1.75 | 512 | 139 | 607 | 102 | 447 | 51 |
| 2 | 517 | 142 | 640 | 122 | 483 | 64 |
| 3 | 509 | 123 | 622 | 150 | 496 | 92 |
| 4 | 511 | 118 | 587 | 130 | 507 | 88 |
| 6 | 472 | 104 | 527 | 133 | 442 | 80 |
| 8 | 422 | 94 | 469 | 119 | 413 | 49 |
| 10 | 373 | 95 | 431 | 147 | 363 | 55 |
| 12 | 350 | 91 | 394 | 142 | 329 | 55 |
| 14 | 510 | 123 | 581 | 69 | 309 | 50 |
| 16 | 495 | 70 | 625 | 177 | 274 | 54 |
| 18 | 449 | 85 | 553 | 168 | 264 | 58 |
| 20 | 414 | 88 | 510 | 162 | 237 | 44 |
| 22 | 394 | 104 | 457 | 123 | 248 | 28 |
| 24 | 385 | 110 | 437 | 135 | 261 | 58 |

[a] IGF-1 at screening

TABLE 8

Mean and SD of IGF-1 SD Scores at Steady State by Dose Group

| Time (hr) | 40 µg/kg BID | | 80 µg/kg BID | | 80 µg/kg QD | |
|---|---|---|---|---|---|---|
| | Mean | SD | Mean | SD | Mean | SD |
| −99 [a] | −2.1 | 0.59 | −2.29 | 0.57 | −1.86 | 0.33 |
| −1 | 0.97 | 0.82 | 0.59 | 0.73 | −0.65 | 0.83 |
| 0 | 0.84 | 0.96 | 0.41 | 0.91 | −0.42 | 0.61 |
| 0.25 | 1.21 | 0.94 | 1.14 | 0.85 | −0.08 | 0.49 |
| 0.5 | 1.15 | 0.97 | 1.42 | 0.93 | 0.32 | 0.56 |
| 0.75 | 1.4 | 1.25 | 1.57 | 0.8 | 0.61 | 0.5 |
| 1 | 1.54 | 1.32 | 1.85 | 0.62 | 0.94 | 0.4 |
| 1.25 | 1.85 | 1.32 | 1.95 | 0.72 | 1.14 | 0.46 |
| 1.5 | 1.85 | 1.21 | 2.17 | 0.65 | 1.46 | 0.3 |
| 1.75 | 2.08 | 1.28 | 2.17 | 0.68 | 1.52 | 0.43 |
| 2 | 2.11 | 1.26 | 2.35 | 0.77 | 1.81 | 0.64 |
| 3 | 2.07 | 1.19 | 2.24 | 0.92 | 1.93 | 0.88 |
| 4 | 2.05 | 1.07 | 2.21 | 0.87 | 2 | 0.75 |
| 6 | 1.72 | 0.98 | 1.82 | 0.91 | 1.52 | 0.74 |
| 8 | 1.29 | 0.97 | 1.32 | 0.83 | 1.33 | 0.73 |
| 10 | 0.78 | 0.96 | 1.04 | 1.02 | 0.9 | 0.66 |
| 12 | 0.52 | 0.92 | 0.76 | 1.05 | 0.58 | 0.64 |
| 14 | 2.05 | 1.13 | 1.97 | 0.39 | 0.39 | 0.56 |
| 16 | 1.93 | 0.72 | 2.24 | 1.06 | 0 | 0.53 |
| 18 | 1.51 | 0.86 | 1.82 | 1.06 | −0.1 | 0.62 |
| 20 | 1.18 | 0.88 | 1.56 | 1.06 | −0.43 | 0.42 |
| 22 | 0.92 | 1.02 | 1.23 | 0.87 | −0.31 | 0.25 |
| 24 | 0.81 | 1.12 | 1.07 | 0.96 | −0.19 | 0.56 |

[a] IGF-1 SD Score at screening

TABLE 9

Mean and SD of IGFBP-3 at Steady State by Dose Group

| Time (hr) | 40 mcg/kg BID | | 80 mcg/kg BID | | 80 mcg/kg QD | |
|---|---|---|---|---|---|---|
| | Mean | SD | Mean | SD | Mean | SD |
| −99 | 2.82 | 0.35 | 2.52 | 0.63 | 2.62 | 0.51 |
| −1 | 2.33 | 0.40 | 2.10 | 0.41 | 2.27 | 0.59 |
| 0.25 | 2.42 | 0.43 | 2.27 | 0.36 | 2.30 | 0.44 |
| 0.5 | 2.65 | 0.44 | 2.17 | 0.36 | 2.18 | 0.30 |
| 0.75 | 2.40 | 0.61 | 2.22 | 0.35 | 2.17 | 0.50 |
| 1 | 2.48 | 0.41 | 2.33 | 0.36 | 2.20 | 0.21 |
| 1.25 | 2.48 | 0.39 | 2.32 | 0.34 | 2.22 | 0.26 |
| 1.5 | 2.47 | 0.26 | 2.38 | 0.34 | 2.40 | 0.40 |
| 1.75 | 2.50 | 0.43 | 2.53 | 0.37 | 2.53 | 0.60 |
| 2 | 2.45 | 0.30 | 2.30 | 0.50 | 2.50 | 0.46 |
| 3 | 2.52 | 0.44 | 2.55 | 0.68 | 2.60 | 0.64 |
| 6 | 2.58 | 0.25 | 2.43 | 0.44 | 2.47 | 0.47 |
| 8 | 2.57 | 0.52 | 2.42 | 0.36 | 2.62 | 0.71 |
| 10 | 2.37 | 0.27 | 2.32 | 0.50 | 2.30 | 0.37 |
| 14 | 2.53 | 0.37 | 2.38 | 0.37 | 2.03 | 0.25 |
| 16 | 2.55 | 0.59 | 2.35 | 0.61 | 2.08 | 0.42 |
| 20 | 2.33 | 0.38 | 2.28 | 0.53 | 2.10 | 0.25 |

[a] IGF-1 SD Score at screening

TABLE 10

Total IGF-1 Steady-State Pharmacokinetic Parameters by Dose Group [a]

| Cohort | Patient ID | IGF-1 Baseline (ng/mL) | IGFBP-3 Baseline (µg/mL) | $C_{min}$ (ng/mL) | $C_{max}$ (ng/mL) | $T_{max}$ (hr) | $AUC_{ss}$ (hr * ng/mL) | Half-life (hr) | Vz/F (L/kg) | CL/F (L/hr/kg) |
|---|---|---|---|---|---|---|---|---|---|---|
| \multicolumn{11}{c}{40 µg/kg BID} |
| 1 | 4003 | 212 | 2.8 | 125 | 295 | 1.5 | 4573 | 3.64 | 0.683 | 0.0350 |
| 1 | 4005 | 126 | 2.3 | 104 | 265 | 3 | 5125 | 8.71 | 0.121 | 0.0156 |
| 1 | 4011 | 172 | 2.5 | 263 | 444 | 1.75 | 7680 | 9.90 | 0.055 | 0.0104 |
| 2 | 5001 | 112 | 3.2 | 237 | 382 | 2 | 6499 | 13.08 | 0.154 | 0.0123 |
| 2 | 5005 | 110 | 2.9 | 207 | 334 | 2 | 6734 | 23.63 | 0.149 | 0.0119 |
| 2 | 5007 | 153 | 3.4 | 364 | 607 | 2 | 10947 | 13.09 | 0.213 | 0.0146 |
|  | N | 6 | 6 | 6 | 6 | 6 | 6 | 6 | 6 | 6 |
|  | Mean | 148 | 2.8 | 217 | 388 | 2.04 | 6927 | 12.01 | 0.229 | 0.0166 |
|  | SD | 40 | 0.4 | 95 | 125 | 0.51 | 2269 | 6.68 | 0.228 | 0.0092 |
|  | Min | 110 | 2.3 | 104 | 265 | 1.50 | 4573 | 3.64 | 0.055 | 0.0104 |
|  | Max | 212 | 3.4 | 364 | 607 | 3.00 | 10947 | 23.63 | 0.683 | 0.0350 |
|  | % CV | 27.0 | 14.5 | 44.0 | 32.2 | 25.0 | 32.8 | 55.6 | 99.6 | 55.2 |
| \multicolumn{11}{c}{80 µg/kg BID} |
| 1 | 4001 | 124 | 2.3 | 172 | 456 | 2 | 7398 | 13.54 | 0.125 | 0.0108 |
| 1 | 4006 | 110 | 1.7 | 152 | 463 | 1.75 | 7267 | 10.10 | 0.245 | 0.0220 |
| 1 | 4009 | 99 | 1.9 | 246 | 461 | 1.75 | 8236 | 7.70 | 0.139 | 0.0097 |
| 2 | 5003 | 151 | 3.1 | 193 | 591 | 2 | 8650 | 8.32 | 0.175 | 0.0092 |
| 2 | 5004 | 116 | 2.5 | 272 | 518 | 3 | 10805 | 15.34 | 0.124 | 0.0074 |
| 2 | 5009 | 199 | 3.5 | 460 | 725 | 4 | 12778 | 9.60 | 0.150 | 0.0125 |
|  | N | 6 | 6 | 6 | 6 | 6 | 6 | 6 | 6 | 6 |
|  | Mean | 133 | 2.5 | 249 | 536 | 2.42 | 9189 | 10.77 | 0.160 | 0.0120 |
|  | SD | 37 | 0.7 | 113 | 106 | 0.90 | 2173 | 3.02 | 0.046 | 0.0052 |
|  | Min | 99 | 1.7 | 152 | 456 | 1.75 | 7267 | 7.70 | 0.124 | 0.0074 |
|  | Max | 199 | 3.5 | 460 | 725 | 4.00 | 12778 | 15.34 | 0.245 | 0.0220 |
|  | % CV | 27.6 | 27.7 | 45.2 | 19.8 | 37.4 | 23.6 | 28.1 | 28.7 | 43.6 |
| \multicolumn{11}{c}{80 µg/kg QD} |
| 1 | 4002 | 201 | 2.4 | 66 | 325 | 3 | 4531 | 5.37 | 0.781 | 0.0353 |
| 1 | 4004 | 141 | 2.3 | 83 | 355 | 4 | 4919 | 8.66 | 0.554 | 0.0163 |
| 1 | 4007 | 130 | 2 | 57 | 366 | 4 | 4635 | 7.99 | 0.240 | 0.0173 |
| 2 | 5002 | 98 | 2.5 | 75 | 372 | 2 | 4725 | 11.63 | 0.320 | 0.0169 |
| 2 | 5006 | 101 | 2.4 | 94 | 324 | 4 | 4551 | 9.65 | 0.356 | 0.0176 |
| 2 | 5008 | 93 | 3.2 | 174 | 561 | 3 | 7512 | 14.03 | 0.295 | 0.0213 |
|  | N | 6 | 6 | 6 | 6 | 6 | 6 | 6 | 6 | 6 |
|  | Mean | 127 | 2.5 | 92 | 384 | 3.33 | 5145 | 9.56 | 0.424 | 0.0208 |
|  | SD | 41 | 0.4 | 42 | 89 | 0.82 | 1168 | 3.00 | 0.205 | 0.0073 |
|  | Min | 93 | 2.0 | 57 | 324 | 2.00 | 4531 | 5.37 | 0.240 | 0.0163 |
|  | Max | 201 | 3.2 | 174 | 561 | 4.00 | 7512 | 14.03 | 0.781 | 0.0353 |
|  | % CV | 32.1 | 16.1 | 46.4 | 23.2 | 24.5 | 22.7 | 31.4 | 48.4 | 35.3 |

[a] Non-compartmental analysis of baseline-corrected total IGF-1 data

Example 3

Determination of Total IGF-1 Steady-State AUC in Short-Term Treatment with Recombinant Human Insulin-Like Growth Factor-1 (rhIGF-1) in Subjects with IGF-1 Deficiency Total IGF-1 steady-state AUC were determined from 18 subjects in the study described in Example 2 above. Predicted total IGF-1 steady-state AUC and clearance values from the PK model were compared with the observed values.

Methods: The steady-state AUC over a 24-hour period and CL/F were determined by a non-compartmental method based on the baseline corrected total IGF-1 concentrations at steady state from 18 subjects in the MS302a study described in Example 2 above.

The model predicted CL/F and the corresponding steady-state AUC values were calculated based on the population PK model derived from the single dose data in MS302 study. The IGFBP-3 value of each subject was used to predict the CL/F value and steady-state $AUC_{ss}$ over a 24-hour period as shown in equations below.

$$CL/F = 0.0104 * (IGFBP3/3.0)^{-0.82} \quad (1)$$

$$AUC_{ss} = Dose/CL/F \quad (2)$$

The model can only predict the mean CL/F of a subpopulation with a given IGFBP-3 value. It cannot predict the CL/F of individual subjects due to between-subject variability. In order to compare the steady-state total IGF-1 concentration-time course of individual subjects with the model predictions, Monte Carlo simulations of total IGF-1 concentrations over a 24-hour period at steady state were done with sample size of 1000 based on the IGFBP-3 value at the screening and the dosage regimen assigned to each subject. The mean and 90% confidence interval (CI) of the total IGF-1 concentrations over the 24-hour period were calculated.

Results: The steady-state AUC and CL/F of total IGF-1 in 18 subjects from study of Example 2 were compared with the model predicted AUC and CL/F in Table 11 below based on the IGFBP-3 at screening and in Table 12 below based on the IGFBP-3 in Day 21 just prior to dosing. The mean $AUC_{ss}$ is about 21% lower and the mean CL/F is about 30% higher than the model predicted values in Table 11 below when it is based on the IGFBP-3 at screening. The IGFBP-3 decreased from 2.61±0.52 µg/mL at screening to 2.23±0.48 µg/mL in Day 21 just prior to dosing. The mean $AUC_{ss}$ is about 11% lower and the mean CL/F is about 14% higher than the model predicted values in Table 12 below when it is based on the IGFBP-3 in Day 21 just prior to dosing. The decrease in IGFBP-3 in Day 21 can account for some of the improvement in model predicted AUC$_{ss}$ and CL/F.

and 30. All 18 subjects in the three different dosage regimens were identified by different markers in these figures.

TABLE 11

Predicted and Observed Total IGF-1 Steady-State AUC and CL/F Based on IGFBP-3 at Screening

| Cohort | Dose Group (μg/kg) | | Subject ID | IGF-1 $^c$ (ng/mL) | IGFBP-3 $^c$ (μg/mL) | AUC$_{ss}$ $^a$ (hr * ng/mL) | Predicted $^b$ AUC (hr * ng/mL) | CL/F (L/hr/kg) | Predicted CL/F $^b$ (L/hr/kg) |
|---|---|---|---|---|---|---|---|---|---|
| 1 | 40 | BID | 4003 | 212 | 2.8 | 4573 | 7264 | 0.0175 | 0.011 |
| 1 | 40 | BID | 4005 | 126 | 2.3 | 5125 | 6170 | 0.0156 | 0.013 |
| 1 | 40 | BID | 4011 | 172 | 2.5 | 7680 | 6612 | 0.0104 | 0.0121 |
| 2 | 40 | BID | 5001 | 112 | 3.2 | 6499 | 8116 | 0.0123 | 0.0099 |
| 2 | 40 | BID | 5005 | 110 | 2.9 | 6734 | 7479 | 0.0119 | 0.0107 |
| 2 | 40 | BID | 5007 | 153 | 3.4 | 10947 | 8534 | 0.0073 | 0.0094 |
| 1 | 80 | BID | 4001 | 124 | 2.3 | 7398 | 12340 | 0.0216 | 0.013 |
| 1 | 80 | BID | 4006 | 110 | 1.7 | 7267 | 9602 | 0.022 | 0.0167 |
| 1 | 80 | BID | 4009 | 99 | 1.9 | 8236 | 10530 | 0.0194 | 0.0152 |
| 2 | 80 | BID | 5003 | 151 | 3.1 | 8650 | 15809 | 0.0185 | 0.0101 |
| 2 | 80 | BID | 5004 | 116 | 2.5 | 10805 | 13224 | 0.0148 | 0.0121 |
| 2 | 80 | BID | 5009 | 199 | 3.5 | 12778 | 17484 | 0.0125 | 0.0092 |
| 1 | 80 | QD | 4002 | 201 | 2.4 | 4531 | 6392 | 0.0177 | 0.0125 |
| 1 | 80 | QD | 4004 | 141 | 2.3 | 4919 | 6170 | 0.0163 | 0.013 |
| 1 | 80 | QD | 4007 | 130 | 2 | 4635 | 5494 | 0.0173 | 0.0146 |
| 2 | 80 | QD | 5002 | 98 | 2.5 | 4725 | 6612 | 0.0169 | 0.0121 |
| 2 | 80 | QD | 5006 | 101 | 2.4 | 4551 | 6392 | 0.0176 | 0.0125 |
| 2 | 80 | QD | 5008 | 93 | 3.2 | 7512 | 8116 | 0.0106 | 0.0099 |
| | | | Mean | 136.0 | 2.61 | 7087 | 9019 | 0.0156 | 0.0120 |
| | | | SD | 37.8 | 0.52 | 2490 | 3519 | 0.004 | 0.0021 |

$^a$ Steady-state AUC over 24 hour
$^b$ Predicted AUC = Dose/(predicted CL/F) where predicted CL/F = 0.0104 * (IGFBP3/3.0) − 0.82
$^c$ IGF-1 and IGFBP-3 values at screening phase

TABLE 12

Predicted and Observed Total IGF-1 Steady-State AUC and CL/F Based on IGFBP-3 on Day 21 just Prior to Dosing

| Cohort | Dose Group (μg/kg) | | Subject ID | IGF-1 $^c$ (ng/mL) | IGFBP-3 $^d$ (μg/mL) | AUC$_{ss}$ $^a$ (hr * ng/mL) | Predicted $^b$ AUC (hr * ng/mL) | CL/F (L/hr/kg) | Predicted CL/F $^b$ (L/hr/kg) |
|---|---|---|---|---|---|---|---|---|---|
| 1 | 40 | BID | 4003 | 212 | 2.3 | 4573 | 6186 | 0.0175 | 0.0129 |
| 1 | 40 | BID | 4005 | 126 | 2.1 | 5125 | 5742 | 0.0156 | 0.0139 |
| 1 | 40 | BID | 4011 | 172 | 2.7 | 7680 | 7056 | 0.0104 | 0.0113 |
| 2 | 40 | BID | 5001 | 112 | 1.9 | 6499 | 5289 | 0.0123 | 0.0151 |
| 2 | 40 | BID | 5005 | 110 | 2.1 | 6734 | 5742 | 0.0119 | 0.0139 |
| 2 | 40 | BID | 5007 | 153 | 3.1 | 10947 | 7902 | 0.0073 | 0.0101 |
| 1 | 80 | BID | 4001 | 124 | 1.8 | 7398 | 10120 | 0.0216 | 0.0158 |
| 1 | 80 | BID | 4006 | 110 | 1.8 | 7267 | 10120 | 0.0220 | 0.0158 |
| 1 | 80 | BID | 4009 | 99 | 1.8 | 8236 | 10120 | 0.0194 | 0.0158 |
| 2 | 80 | BID | 5003 | 151 | 2.6 | 8650 | 13681 | 0.0185 | 0.0117 |
| 2 | 80 | BID | 5004 | 116 | 2.2 | 10805 | 11930 | 0.0148 | 0.0134 |
| 2 | 80 | BID | 5009 | 199 | 2.8 | 12778 | 14538 | 0.0125 | 0.0110 |
| 1 | 80 | QD | 4002 | 201 | 1.7 | 4531 | 4828 | 0.0177 | 0.0166 |
| 1 | 80 | QD | 4004 | 141 | 2 | 4919 | 5516 | 0.0163 | 0.0145 |
| 1 | 80 | QD | 4007 | 130 | 2.2 | 4635 | 5965 | 0.0173 | 0.0134 |
| 2 | 80 | QD | 5002 | 98 | 1.8 | 4725 | 5060 | 0.0169 | 0.0158 |
| 2 | 80 | QD | 5006 | 101 | 1.9 | 4551 | 5289 | 0.0176 | 0.0151 |
| 2 | 80 | QD | 5008 | 93 | 3.3 | 7512 | 8318 | 0.0106 | 0.0096 |
| | | | Mean | 136.0 | 2.23 | 7087 | 7967 | 0.0156 | 0.0137 |
| | | | SD | 37.8 | 0.48 | 2490 | 3088 | 0.0040 | 0.0021 |

$^a$ Steady-State AUC over 24 hour
$^b$ Predicted AUC = Dose/(predicted CL/F) where predicted CL/F = 0.0104 * (IGFBP3/3.0)$^{-0.82}$
$^c$ IGF-1 values at screening phase
$^d$ IGFBP-3 values just prior to dose on day 21

The model predicted AUC$_{ss}$ vs. observed AUC$_{ss}$ of total IGF-1 are presented in FIG. 27 based on the IGFBP-3 at screening and in FIG. 28 based on the IGFBP-3 in Day 21 just prior to dosing. The corresponding percent difference between the predicted and observed steady-state AUC$_{ss}$ of total IGF-1 vs. total daily dose were presented in FIGS. 29 and 30. All 18 subjects in the three different dosage regimens were identified by different markers in these figures.

Discussion: The steady-state AUC$_{ss}$ of total IGF-1 tends to be lower than the model predicted values by about 20% at 160 μg/kg total daily dose as shown in FIG. 30. The model assumed no change in the formation of endogenous IGF-1 with chronic rhIGF-1 dosing. The lower than predicted IGF-1 at steady state might be explained by a suppression of endogenous IGF-1 and IGFBP-3 production by chronic administration of rhIGF-1. The suppression of endogenous production of IGF-1 seems to be much more pronounced at 160 μg/kg than at 80 μg/kg daily dose. Once daily rhIGF-1, to allow a maintained AUC despite greater fluctuations in IGF-1 levels, can be seen as advantageous to minimize a suppression of GH secretion.

Example 4

Pharmacokinetic and Growth Responses of Normal Rats to Daily Injections of rhIGF-1

Methods: Male and female Crl:CD® (SD)BR VAF/Plus® rats were assigned to 10 groups. Each group received dose preparations containing the vehicle or 0.25, 1.0, 4.0, or 10.0 mg of rhIGF-1/kg body weight/day (mg/kg/day) by subcutaneous injection of a dose volume of 1 mL/kg for 104 weeks.

Results: Body weight and body weight gain data for animals are illustrated in FIGS. 13-16. Administration of the test material caused an increase in body weight gain in males and females at all dose levels. The magnitude of this effect increased with increasing dose, although the effect for animals given 10.0 mg/kg/day was only slightly greater than that of those given 4.0 mg/kg/day. For males the effect on mean body weight was generally statistically significant from Week 6 throughout the majority of the study at the 10.0, 4.0, and 1.0 mg/kg/day dose levels; for males given 0.25 mg/kg/day, statistically significant changes were first apparent at Week 22. For females, the effect on mean body weight was generally statistically significant throughout the majority of the study beginning at Week 3 for animals given 10.0 and 4.0 mg/kg/day and Week 6 for animals given 1.0 mg/kg/day. For females given 0.25 mg/kg/day, statistically significant changes were generally noted from Week 20 to 63. The magnitude of the effect on body weight was marked for animals given 4.0 or 10.0 mg/kg/day. At the beginning of Week 69, a time when survival for males and females given the high dose was at least 50%, mean body weights for males given 0.25, 1.0, 4.0, or 10.0 mg/kg/day were 109%, 116%, 123% and 129% of control values, respectively; for females these data were 104%, 113%, 128% and 131% of control values, respectively. The increased body weight gain for test material-treated animals was consistent with increases in food consumption also noted in these groups.

Figure 12:
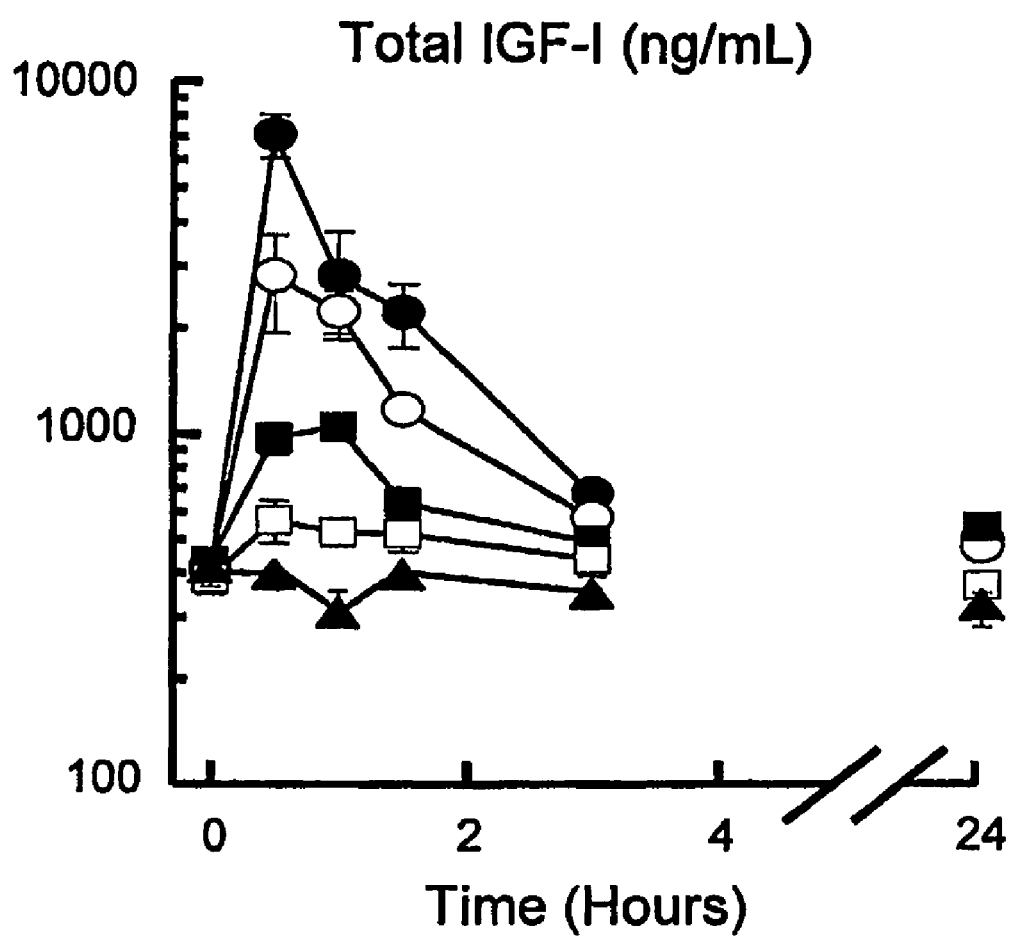
FIG. 12 is a graph depicting the pharmacokinetics of IGF-1 in normal male rats. IGF-1 concentration (ng IGF-1 per ml of blood) is shown at certain time points during 24 hours post-administration. The solid triangles, open squares, solid squares, open circles, and solid circles represent treatment groups that received their first subcutaneous injection of placebo, 0.25 mg IGF-1/kg body weight, 1 mg IGF-1/kg body weight, 4 mg IGF-1/kg body weight, and 10 mg IGF-1/kg body weight, respectively.
Figure 13:
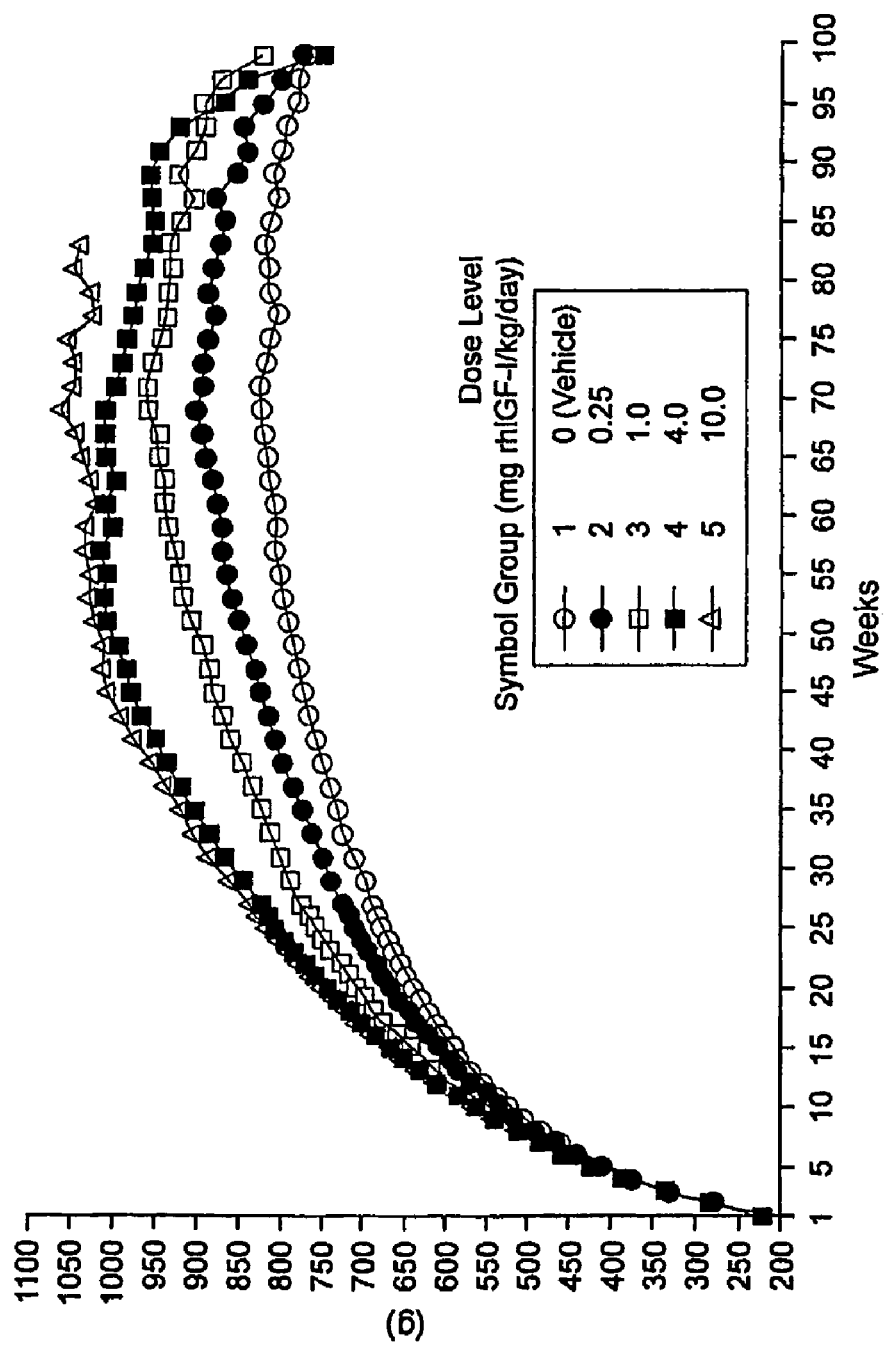
FIG. 13 is a graph depicting the growth response of normal male rats to daily injections of IGF-1 in the form of mean body weights for up to a two year course of treatment. Mean body weight (g) for each dose level cohort is shown at regular intervals over the course of treatment. The open circles, solid circles, open squares, solid squares, and open triangles represent treatment groups that received daily subcutaneous injections of placebo, 0.25 mg IGF-1/kg body weight, 1 mg IGF-1/kg body weight, 4 mg IGF-1/kg body weight, and 10 mg IGF-1/kg body weight, respectively.
Figure 14:
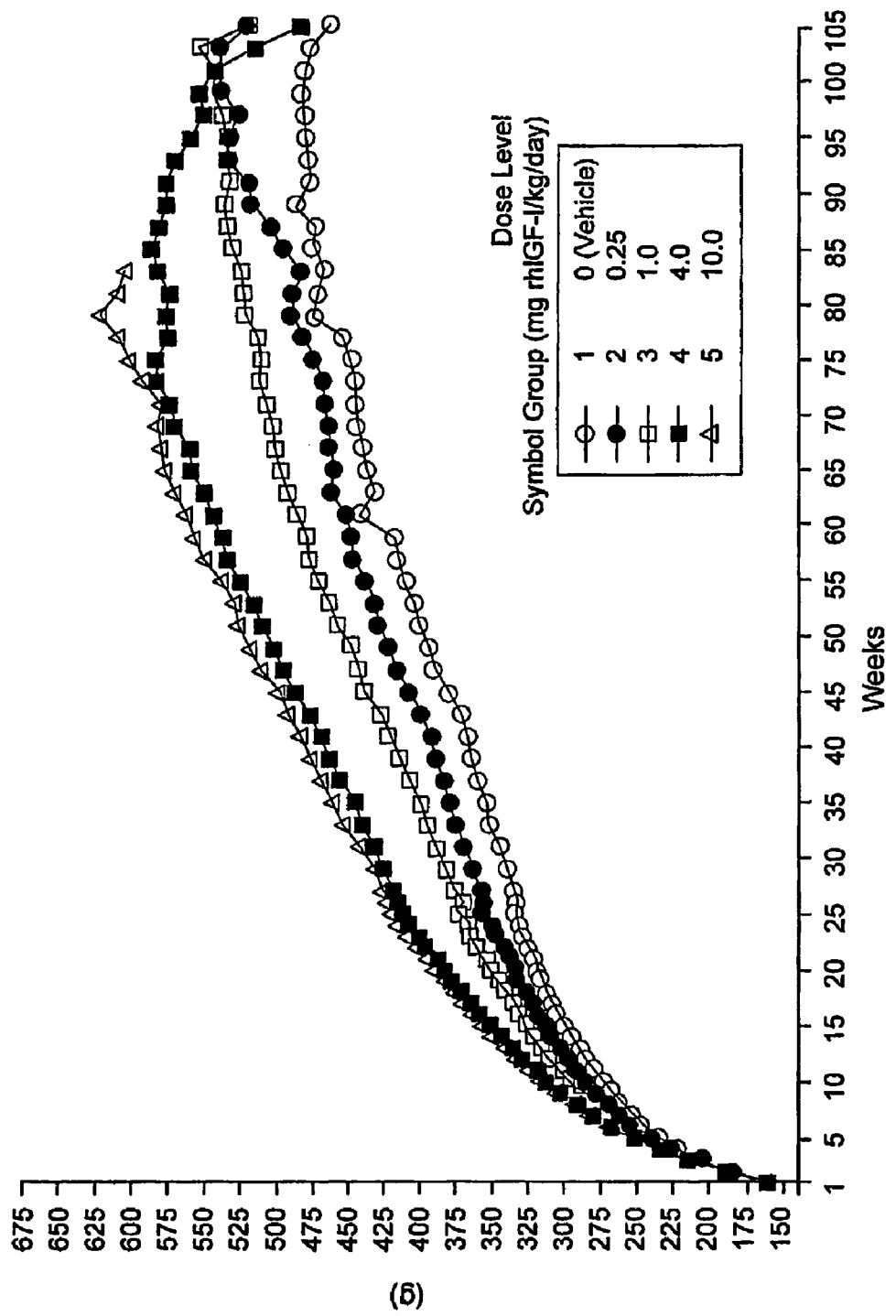
FIG. 14 is a graph depicting the growth response of normal female rats to daily injections of IGF-1 in the form of mean body weights for up to a two year course of treatment. Mean body weight (g) for each dose level cohort is shown at regular intervals over the course of treatment. The open circles, solid circles, open squares, solid squares, and open triangles represent treatment groups that received daily subcutaneous injections of placebo, 0.25 mg IGF-1/kg body weight, 1 mg IGF-1/kg body weight, 4 mg IGF-1/kg body weight, and 10 mg IGF-1/kg body weight, respectively.
Figure 15:
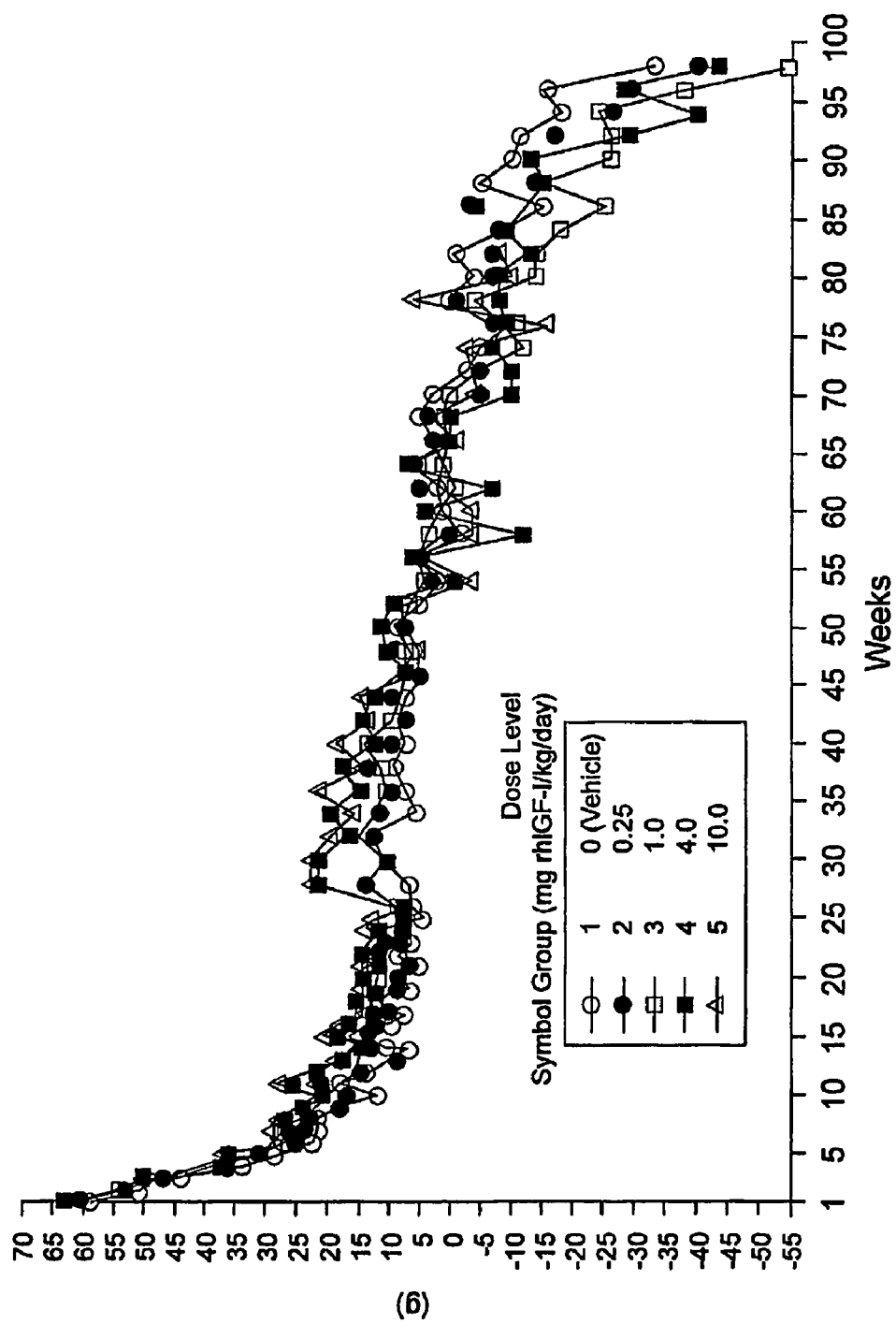
FIG. 15 is a graph depicting the growth response of normal male rats to daily injections of IGF-1 in the form of mean body weight change for up to a two year course of treatment. Mean body weight change (g/week) for each dose level cohort is shown at regular intervals over the course of treatment. The open circles, solid circles, open squares, solid squares, and open triangles represent treatment groups that received daily subcutaneous injections of placebo, 0.25 mg IGF-1/kg body weight, 1 mg IGF-1/kg body weight, 4 mg IGF-1/kg body weight, and 10 mg IGF-1/kg body weight, respectively.
Figure 16:
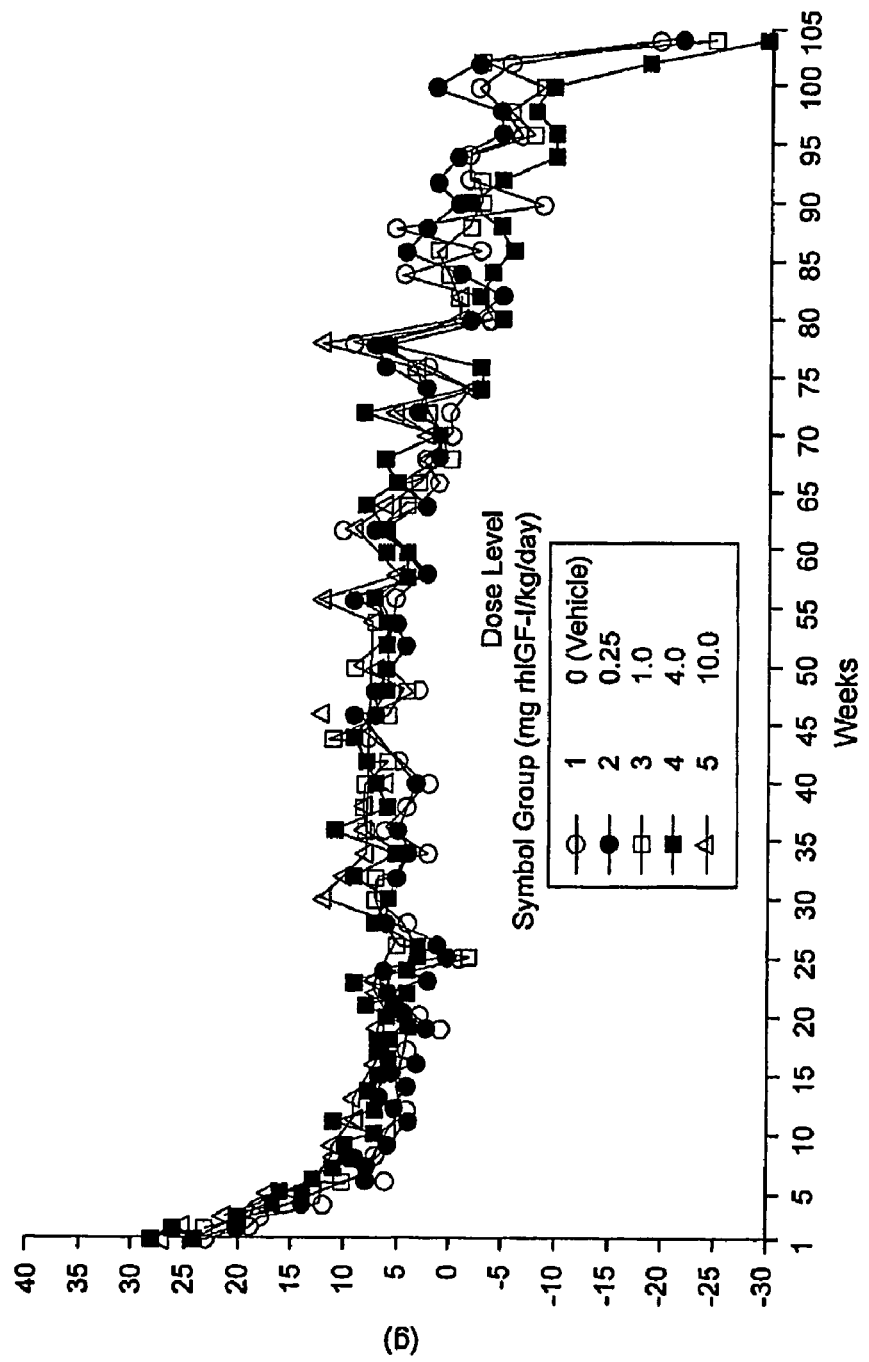
FIG. 16 is a graph depicting the growth response of normal female rats to daily injections of IGF-1 in the form of mean body weight change for up to a two year course of treatment.

The pharmacokinetics of IGF-1, shown in FIG. 12, are dramatic in that blood levels rose to very high levels and then fell almost to baseline levels after 24 hours. The large growth response to IGF-1 indicates that overall the GH/IGF-1 axis is stimulated by therapy with once daily IGF-1 injections.

All references cited herein are specifically incorporated by reference as if fully set forth herein.

Having hereinabove disclosed exemplary embodiments of the present invention, those skilled in the art will recognize that this disclosure is only exemplary such that various alternatives, adaptations, and modifications are within the scope of the invention, and are contemplated by the Applicant. Accordingly, the present invention is not limited to the specific embodiments as illustrated above, but is defined by the following claims.

What is claimed:

1. A method for treating a human pediatric subject having primary insulin-like growth factor-1 deficiency (IGFD) comprising;
administering to a human pediatric subject suffering from a growth disorder characterized by primary IGFD and partial endogenous growth hormone signaling a combination of an amount of insulin-like growth factor-1 (IGF-1) and an amount of growth hormone (GH) effective to promote growth in the subject, wherein the subject is further characterized as follows:
the subject, at the time of treatment or prior to initial treatment with IGF-1, has or had a height at least about 2.0 standard deviations (SD) below a normal mean for a subject of the same age and gender, and
the subject has or had a blood level of IGF-1 below, but not more than about 2 SD below, normal mean levels for a subject of the same age and gender,
wherein the subject receives each of IGF-1 and GH in a single administration per day, and wherein the single administration of IGF-1 and the single administration of GH are administered to the patient substantially contemporaneously each day.

2. The method of claim 1, wherein IGF-1 is administered in a dose of about 25 to 250 μg/kg/day and GH is administered in a dose of about 0.05 to 0.5 mg/kg/week.

3. The method of claim 1, wherein IGF-1 is administered in a dose of about 20 to 240 μg/kg/day.

4. The method of claim 1, wherein the single administration of GH and the single administration of IGF-1 are each administered to the patient by subcutaneous injection.

5. The method of claim 1, wherein the subject is further characterized as having a blood level of growth hormone-binding protein (GHBP) which is at least normal for a subject of the same age and gender.

6. The method of claim 1, wherein the subject does not have partial growth hormone insensitivity syndrome.

7. The method of claim 1, wherein the subject receives the single administration of IGF-1 and the single administration of GH within about 2 hours of awakening from sleep each day.

8. The method of claim 1, wherein the subject receives the single administration of IGF-1 with a meal or snack.

9. The method of claim 1, wherein the subject does not receive treatment with insulin-like growth factor binding protein-3 (IGFBP-3) concomitantly with the IGF-1 therapy of the method.

10. The method of claim 1, wherein the GH and the IGF-1 are in the form of separate solutions that are administered by separate injections.

11. The method of claim 10, wherein IGF-1 is administered in a dose of about 25 to 250 μg/kg/day and GH is administered in a dose of about 0.05 to 0.5 mg/kg/week.

12. The method of claim 10, wherein IGF-1 is administered in a dose of about 20 to 240 μg/kg/day.

13. The method of claim 10, wherein the single administration of GH and the single administration of IGF-1 are each administered to the patient by subcutaneous injection.

14. The method of claim 10, wherein the subject is further characterized as having a blood level of growth hormone binding protein (GHBP) which is at least normal for a subject of the same age and gender.

15. The method of claim 10, wherein the subject does not have partial growth hormone insensitivity syndrome.

16. The method of claim 10, wherein the subject receives the single administration of IGF-1 and the single administration of GH within about 2 hours of awakening from sleep each day.

17. The method of claim 10, wherein the subject receives the single administration of IGF-1 with a meal or snack.

18. The method of claim 10, wherein the subject does not receive treatment with insulin-like growth factor binding protein-3 (IGFBP-3) concomitantly with the IGF-1 therapy of the method.

* * * * *